US011998642B2

(12) United States Patent
Bayley et al.

(10) Patent No.: US 11,998,642 B2
(45) Date of Patent: *Jun. 4, 2024

(54) MULTISOMES: ENCAPSULATED DROPLET NETWORKS

(71) Applicant: Oxford University Innovation Limited, Oxford (GB)

(72) Inventors: John Hagan Pryce Bayley, Oxford (GB); Andrew Heron, Oxford (GB); Gabriel Villar, Oxford (GB)

(73) Assignee: Oxford University Innovation Limited, Oxford (GB)

(*) Notice: Subject to any disclaimer, the term of this patent is extended or adjusted under 35 U.S.C. 154(b) by 30 days.

This patent is subject to a terminal disclaimer.

(21) Appl. No.: 17/853,000

(22) Filed: Jun. 29, 2022

(65) Prior Publication Data
US 2023/0048266 A1    Feb. 16, 2023

Related U.S. Application Data

(63) Continuation of application No. 16/721,302, filed on Dec. 19, 2019, now Pat. No. 11,406,603, which is a continuation of application No. 14/354,706, filed as application No. PCT/GB2012/052736 on Nov. 2, 2012, now Pat. No. 10,548,852.

(60) Provisional application No. 61/592,062, filed on Jan. 30, 2012.

(30) Foreign Application Priority Data

Nov. 3, 2011 (GB) .................................. 1119032

(51) Int. Cl.
| | |
|---|---|
| *A61K 9/50* | (2006.01) |
| *A61K 9/113* | (2006.01) |
| *A61K 31/085* | (2006.01) |
| *A61K 49/00* | (2006.01) |
| *B01J 13/02* | (2006.01) |
| *C09B 67/02* | (2006.01) |
| *A61K 9/107* | (2006.01) |
| *A61K 9/127* | (2006.01) |

(52) U.S. Cl.
CPC ............... *A61K 9/50* (2013.01); *A61K 9/113* (2013.01); *A61K 31/085* (2013.01); *A61K 49/0002* (2013.01); *B01J 13/02* (2013.01); *B01J 13/025* (2013.01); *C09B 67/0097* (2013.01); *A61K 9/1075* (2013.01); *A61K 9/1271* (2013.01); *Y10T 428/2984* (2015.01)

(58) Field of Classification Search
CPC ........ A61K 9/50; A61K 9/113; A61K 31/085; A61K 49/0002; A61K 9/1075; A61K 9/1271; B01J 13/02; B01J 13/025; C09B 67/0097; Y10T 428/2984
See application file for complete search history.

(56) References Cited

U.S. PATENT DOCUMENTS

| | | | |
|---|---|---|---|
| 4,812,856 | A | 3/1989 | Wallace |
| 4,934,564 | A | 6/1990 | Piatt |
| 5,464,629 | A | 11/1995 | Monshipouri et al. |
| 5,858,399 | A | 1/1999 | Lanza |
| 5,925,511 | A | 7/1999 | Fuhr et al. |
| 6,531,156 | B1 | 3/2003 | Clark et al. |
| 6,713,021 | B1 | 3/2004 | Shvets et al. |
| 6,962,747 | B1 | 11/2005 | Sasaki et al. |
| 6,995,024 | B2 | 2/2006 | Smith et al. |
| 7,217,410 | B2 | 5/2007 | Suslick et al. |
| 8,268,627 | B2 | 9/2012 | Bayley et al. |
| 8,562,807 | B2 | 10/2013 | Srinivasan et al. |
| 8,784,929 | B2 | 7/2014 | Wallace et al. |
| 8,992,984 | B1 | 3/2015 | Brinker et al. |
| 9,223,317 | B2 | 12/2015 | Winger |
| 9,831,010 | B2 | 11/2017 | Bayley et al. |
| 10,548,852 | B2 | 2/2020 | Bayley et al. |
| 10,950,376 | B2 | 3/2021 | Bayley et al. |
| 10,978,218 | B2 | 4/2021 | Bayley et al. |
| 11,213,797 | B2 | 1/2022 | Bayley et al. |
| 11,406,603 | B2 | 8/2022 | Bayley et al. |
| 2001/0051334 | A1 | 12/2001 | Barth et al. |
| 2002/0106308 | A1 | 8/2002 | Zweifel et al. |
| 2003/0035842 | A1 | 2/2003 | Kazakov et al. |

(Continued)

FOREIGN PATENT DOCUMENTS

| | | |
|---|---|---|
| CA | 2 564 120 A1 | 8/1998 |
| EP | 1 707 965 A1 | 10/2006 |

(Continued)

OTHER PUBLICATIONS

U.S. Appl. No. 61/592,062, Multisomes: Encapsulated Droplet Networks, filed Jan. 30, 2012.
International Search Report and Written Opinion from International Application No. PCT/GB2013/052794; Filing Date: Oct. 25, 2013; Entitled: "Hydrogel Network"; dated Jul. 1, 2014.
International Preliminary Report on Patentability from International Application No. PCT/GB2013/052794; Filing Date: Oct. 25, 2013; Entitled: "Hydrogel Network", Date of Issuance of report: Apr. 28, 2015.
International Search Report and Written Opinion from International Application No. PCT/GB2013/052796; Filing Date: Oct. 25, 2013; Entitled: "Droplet Assembly Method", dated Jan. 28, 2014.

(Continued)

*Primary Examiner* — Robert S Cabral
(74) *Attorney, Agent, or Firm* — Hamilton, Brook, Smith & Reynolds, P.C.

(57) ABSTRACT

The invention provides a droplet encapsulate comprising: a drop of a hydrophobic medium; a peripheral layer of non-polymeric amphipathic molecules around the surface of the drop; and an aqueous droplet within the peripheral layer, the aqueous droplet comprising: (a) an aqueous medium and (b) an outer layer of non-polymeric amphipathic molecules around the surface of the aqueous medium. The invention also provides processes for preparing the droplet encapsulates. Various uses of the droplet encapsulates are also described, including their use as drug delivery vehicles, in synthetic biology, and in the study of membrane proteins.

20 Claims, 8 Drawing Sheets

(56) References Cited

U.S. PATENT DOCUMENTS

| | | |
|---|---|---|
| 2003/0048341 A1 | 3/2003 | Mutz et al. |
| 2003/0119193 A1 | 6/2003 | Hess et al. |
| 2003/0128267 A1 | 7/2003 | Teung et al. |
| 2004/0191518 A1 | 9/2004 | Naito et al. |
| 2004/0237822 A1 | 12/2004 | Boland et al. |
| 2005/0056713 A1 | 3/2005 | Tisone et al. |
| 2006/0210443 A1 | 9/2006 | Stearns et al. |
| 2007/0120280 A1 | 5/2007 | Anchordoquy et al. |
| 2007/0148697 A1 | 6/2007 | Delaney, Jr. et al. |
| 2007/0243634 A1 | 10/2007 | Pamula et al. |
| 2007/0248541 A1 | 10/2007 | Tagawa et al. |
| 2007/0275415 A1 | 11/2007 | Srinivasan et al. |
| 2007/0293449 A1 | 12/2007 | Cui et al. |
| 2008/0017736 A1 | 1/2008 | Lee et al. |
| 2008/0053205 A1 | 3/2008 | Pollack et al. |
| 2008/0063794 A1 | 3/2008 | Krotz |
| 2008/0153150 A1 | 6/2008 | Holden et al. |
| 2009/0012187 A1 | 1/2009 | Chu et al. |
| 2009/0074988 A1 | 3/2009 | Faris et al. |
| 2009/0131543 A1 | 5/2009 | Weitz et al. |
| 2009/0208466 A1 | 8/2009 | Yoo et al. |
| 2009/0289213 A1 | 11/2009 | Pipper et al. |
| 2010/0032627 A1 | 2/2010 | Bayley et al. |
| 2010/0147450 A1 | 6/2010 | Takeuchi et al. |
| 2010/0173394 A1 | 7/2010 | Colston, Jr. et al. |
| 2010/0316696 A1 | 12/2010 | Wiggenhorn et al. |
| 2011/0041978 A1 | 2/2011 | Wallace |
| 2011/0076734 A1 | 3/2011 | Zhou et al. |
| 2011/0250688 A1 | 10/2011 | Hasan |
| 2011/0305761 A1 | 12/2011 | Shum et al. |
| 2011/0306539 A1 | 12/2011 | Shen et al. |
| 2011/0311408 A1 | 12/2011 | Azimi et al. |
| 2012/0006681 A1 | 1/2012 | Kaler et al. |
| 2012/0116568 A1 | 5/2012 | Murphy et al. |
| 2012/0220481 A1 | 8/2012 | Wallace et al. |
| 2012/0322162 A1 | 12/2012 | Collier et al. |
| 2013/0017564 A1 | 1/2013 | Guillemot et al. |
| 2013/0319861 A1 | 12/2013 | Khandros et al. |
| 2014/0023697 A1 | 1/2014 | Dimauro |
| 2014/0356289 A1 | 12/2014 | Bayley et al. |
| 2015/0248949 A1 | 9/2015 | Bayley et al. |
| 2015/0270043 A1 | 9/2015 | Bayley et al. |
| 2015/0285781 A1 | 10/2015 | Heron et al. |
| 2016/0136888 A1 | 5/2016 | Bayley et al. |
| 2018/0096751 A1 | 4/2018 | Bayley et al. |
| 2020/0214988 A1 | 7/2020 | Bayley et al. |
| 2021/0296033 A1 | 9/2021 | Bayley et al. |
| 2022/0072497 A1 | 3/2022 | Bayley et al. |

FOREIGN PATENT DOCUMENTS

| | | |
|---|---|---|
| EP | 2 253 378 | 11/2010 |
| GB | 1119032.9 | 7/1968 |
| JP | 2001-505224 | 4/2001 |
| JP | 2001-515853 | 9/2001 |
| JP | 2010536551 | 2/2010 |
| JP | 2010-503417 | 4/2010 |
| JP | 2010222282 | 10/2010 |
| JP | 2012/166159 | 9/2012 |
| KR | 1020120038662 | 4/2012 |
| WO | WO 1991/000084 A1 | 1/1991 |
| WO | WO 98/33483 | 8/1998 |
| WO | WO 99/12523 | 3/1999 |
| WO | WO 2005/053643 A1 | 6/2005 |
| WO | WO 2006/096571 A2 | 3/2006 |
| WO | WO 2006/096571 A1 | 9/2006 |
| WO | WO 2007/010668 A1 | 1/2007 |
| WO | WO 2007/094739 A1 | 8/2007 |
| WO | WO 2007/0101174 A2 | 9/2007 |
| WO | WO 2008/012552 A1 | 1/2008 |
| WO | WO 2008/034180 A1 | 3/2008 |
| WO | WO 2009/024775 A1 | 2/2009 |
| WO | WO 2009/049089 A1 | 4/2009 |
| WO | WO 2009/148598 A1 | 12/2009 |
| WO | WO 2010/110471 A1 | 9/2010 |
| WO | WO 2011/015870 A1 | 2/2011 |
| WO | WO 2012/050359 A2 | 4/2012 |
| WO | WO 2013/041983 A1 | 3/2013 |
| WO | WO 2013/064837 A1 | 5/2013 |
| WO | WO 2014/064459 A2 | 5/2014 |
| WO | WO 2014/064461 A1 | 5/2014 |
| WO | WO 2014/087175 A2 | 6/2014 |

OTHER PUBLICATIONS

International Preliminary Report on Patentability from International Application No. PCT/GB2013/052796; Filing Date: Oct. 25, 2013; Entitled: "Droplet Assembly Method", Date of Issuance of report: Apr. 28, 2015.

International Search Report and Written Opinion from International Application No. PCT/GB2013/053229; Filing Date: Dec. 6, 2013; Entitled: "Droplet Assembly by 3D Printing," dated Jun. 17, 2014.

International Preliminary Report on Patentability from International Application No. PCT/GB2013/053229; Filing Date: Dec. 6, 2013; Entitled: "Droplet Assembly by 3D Printing"; Date of Issuance of report: Jun. 9, 2015.

Notification of Transmittal of The International Search Report and the Written Opinion of the International Searching Authority, or the Declaration from International Application No. PCT/GB2012/052736, "Multisomes: Encapsulated Droplet Networks", dated Apr. 25, 2013.

International Preliminary Report on Patentability from International Application No. PCT/GB2012/052736, entitled: "Multisomes: Encapsulated Droplet Networks", Date of issuance of report: May 6, 2014.

Abbott, A., "Biology's new dimension", *Nature*, 424: 870-872 (Aug. 21, 2003).

Abramoff, M. D., et al., "Image processing with Image J", *Biophotonics International*, 11: 36-42 (2004).

Aghdaei, S., et al., "Formation of artificial lipid bilayers using droplet dielectrophoresis", *Lab Chip*, 8: 1617-1620 (2008).

Akashi, K., et al., "Preparation of Giant Liposomes in Physiological Conditions and Their Characterization Under an Optical Microscope", *Biophysical Journal*, 71: 3242-3250 (Dec. 1996).

Aronson, M. P. and Princen, H. M., "Contact angles associated with thin liquid-films in emulsions", *Nature*, 286: 370-372 (Jul. 24, 1980).

Astier, Y., et al, "Protein components for nanodevices", *Current Opinion in Chemical Biology* 9: 576-584 (2005).

Bai, Y. et al., "A double droplet trap system for studying mass transport across a droplet-droplet interface", Lab Chip, 10: 1281-1285 (2010).

Bayley, H et al., "Droplet interface bilayers", *Molecular BioSystems*, 4(12): 1191-1208 (Dec. 2008).

Bodor, N. and Buchwald, P., "Soft Drug Design: General Principles and Recent Applications", *Med. Res. Rev.*, 20:58-101 (2000).

Boland, Thomas et al., "Application of inkjet printing to tissue engineering", *Biotechnology Journal*, 1: 910-917 (2006).

Bolinger, P.- Y. et al., "Integrated Nanoreactor Systems: Triggering the Release and Mixing of Compounds Inside Single Vesicles", *J. Am. Chem. Soc.*, 126(28): 8594-8595 (2004).

Boroske, E., and Elwenspoek, M., "Osmotic Shrinkage of Gian Egg-Lecithin Vesicles", *Biophys. .J.*, 34: 95-109 (Apr. 1981).

Bowden, N., et al., "Molecule-Mimetic Chemistry and Mesoscale Self-Assembly", Acc. Chem. Res. 34(3): 231-238 (2001).

Bowden, N., et al., "Self-Assembly of Mesoscale Objects into Ordered Two-Dimensional Arrays", *Science*, 276: 233-235 (Apr. 11, 1997).

Channon, K., et al., "Synthetic biology through biomolecular design and engineering", *Current Opinion in Structural Biology*, 18: 491-498 (2008).

Cheley, S. et al., "Spontaneous oligomerization of a staphylococcal alpha-hemolysin conformationally constrained by removal of residues that form the transmembrane beta-barrel", *Protein Engineering*, 10: 1433-1443 (1997).

Chiarabelli, C. et al., "Chemical approaches to synthetic biology", *Current Opinion in Biotechnology*, 20: 492-497 (2009).

Choi, I. S. et al., "Macroscopic Hierarchial, Two-Dimensional Self-Assembly", *Angew. Chem. Int. Ed*, 38(20): 3078-3081 (1999).

(56) References Cited

OTHER PUBLICATIONS

Chu, C.-J. et al., "Efficiency of Cytoplasmic Delivery by pH-Sensitive Liposomes to Cells in Culture", *Pharmaceutical Research*, 7(8): 824-834 (1990).
Chu, L.-Y. et al., "Controllable Monodisperse Multiple Emulsions", *Angew. Chem. Int. Edit.*, 46: 8970-8974 (2007).
Clancy, K. and Voigt, C. A., Programming cells: towards an automated 'Genetic Compiler', *Current Opinion in Biotechnology*, 21: 572-581 (2010).
Clavel, F. and Hance, A. J., "Medical Progress HIV Drug Resistance", *New England Journal of Medicine*, 350(10): 1023-1035 (Mar. 4, 2004).
Cukierman, E. et al., "Cell interactions with three-dimensional matrices", *Current Opinion in Cell Biology*, 14: 633-639 (2002).
Cukierman, E. et al., "Taking Cell-Matrix Adhesions to the Third Dimension", *Science*, 294: 1708-1712 (Nov. 23, 2001).
Devine, D. V., et al., "Liposome-complement interactions in rat serum: implications for liposome survival studies", *Biochim. Biophys. Acta*, 1191: 43-51 (1994).
Dixit, S. S., et al., "Droplet Shape Analysis and Permeability Studies in Droplet Lipid Bilayers", Langmuir, 28: 7442-7451 (2012).
Dixit, S. S., et al., "Light-Driven Formation and Rupture of Droplet Bilayers", Langmuir 26(9): 6193-6200 (2010).
Drummond, D. C. et al., "Current status of pH- sensitive liposomes in drug delivery", *Progress in Lipid Research*, 39: 409-460 (2000).
Du, Y., et al., "Directed assembly of Cell-laden microgels for fabrication of 3D tissue constructs", *Proc. Natl. Acad. Sci. (PNAS)*, 105(28): 9522-9527 (2008).
Evans, E., "Probing the Relation Between Force-Lifetime—and Chemistry in Single Modecular Bonds," *Annu. Rev. Biophys. Biomol. Struct.*, 30:105-128 (2001).
Forterre, Y., et al., "How the Venus Flytrap Snaps," *Nature*, 43:421-425 (2005).
Funakoshi, et al., "Lipid Bilayer Formation by Contacting Monolayers in a Microfluidic Device for Membrane Protein Analysis," *Anal. Chem.*, 78(24): 8169-8174 (2006).
Gibson, D. G. et al., "Creation of a Bacterial Cell Controlled by a Chemically Synthesized Genome," *Science*, 329:52-56 (2010).
Gijs, M. A., et al., "Microfluidic Applications of Magnetic Particles for Biological Analysis and Catalysis," *Chem. Rev.*, 110:1518-1563 (2010).
Gross, L.C., et al., "Determining Membrane Capacitance by Dynamic Control of Droplet Interface Bilayer Area," *Langmuir*, 27:14335-14342 (2011).
Gu, L. Q., et al., "Interaction of the noncovalent molecular adapter, betacyclodextrin, with the staphylococcal alpha-hemolysin pore," *Biophys. J.*, 79:1967-1975 (2000).
Gu, L. Q., et al., "Stochastic Sensing of Organic Analytes by a Pore-Forming Protein Containing a Molecular Adapter," *Nature*, 398:686-690 (1999).
Hamer, W. J., et al., "Osmotic Coefficients and Mean Activity Coefficients of Uni-Univalent Electrolytes in Water at 25° C.," *J. Phys. Chem. Ref. Data*, 1:1047-1100 (1972).
Hamilton, J. A., et al., "Transfer of Oleic Acid Between Albumin and Phosphholipid Vesicles," *Proc. Natl Acad. Sci. USA*, 83:82-86 (1986).
Harada, et al., "Bubble wrap of cell-like aggregates", *Nature*, 471:172-175 (2011).
Harada, A., et al., "Macroscopic Self-Assembly Through Molecular Recognition," *Nat. Chem.* 3:34-37 (2011).
Harriss, L. M., et al., "Imaging Multiple Conductance States in an Alamethicin Pore," *J. Am. Chem. Soc.*, 133:14507-14509 (2011).
Heron, A .J., et al., "Direct detection of membrane channels from gels using water-in-oil droplet bilayers," *J. Am. Chem. Soc.*, 129:16042-16047 (2007).
Heron, A. J., et al., "Simultaneous measurement of ionic current and fluorescence from single protein pores," *J. Am. Chem. Soc.*, 131:1652-1653 (2009).
Holden, M. A., et al., "Functional bionetworks from nanoliter water drops," *J. Am. Chem. Soc.*, 129:8650-8655 (2007).

Hu, Z. B., et al., "Synthesis and Application of Modulated Polymer Gels," *Science*, 269: 525-527 (1995).
Huang, J., et al., "Direct Quantitation of Peptide-Mediated Protein Transport across a Droplet-Interface Bilayer," *JACS*, 133:15818-15821 (2011).
Humphrey, W., et al., "VMD: Visual Molecular Dynamics," *J. Molec. Graphics*, 14:33-38 (1996).
Hwang, W. L., et al., "Electrical Behavior of Droplet Interface Bilayer Networks: Experimental Analysis and Modeling," *JACS*, 129:11854-11864 (2007).
Jeong, B., et al., "Lessons from Nature: Stim uli-Responsive Polymers and their Biomedical Applications," *Trends Biotechnol.*, 20:305-311 (2002).
Johnson, J. D., "Intracellular EDTA mimics parvalbumin in the promotion of skeletal muscle relaxation", *Biophys. J.* 76:1514-1522 (1999).
Kankare, J. et al., "Kinetics of Langmuirian Adsorption onto Planar, Spherical, and Cylindrical Surfaces," *Langmuir*, 15:5591-5599 (1999).
Kim, J., et al., "Designing Responsive Buckled Surfaces by Halftone Gel Lithography," *Science*, 335:1201-1205 (2012).
Kim, S., et al., "Preparation of Multivesicular Liposomes", *Biochimica et Biophysica Acta.*, 728(1983): 339-348. (Cited in counterpart EP OA from 1001-001).
Klein, Y., et al., "Shaping of Elastic Sheets by Prescription of Non-Euclidean Metrics," *Science*, 315:1116-1120 (2007).
Korlach, J. et al., "Characterization of lipid bilayer phases by confocal microscopy and fluorescence correlation spectroscopy", *Proc. Natl. Acad. Sci. USA*, 96, 8461-8466 (1999).
Lahann, J., et al., "A Reversibly Switching Surface," *Science*, 299:371-374 (2003).
Lehmann, et al., "Two-dimensional magnetic manipulation of microdroplets on a chip as a platform for bioanalytical application," *Sensors and Actuators B*, 2(117):457-463 (2006).
Leptihn, S., et al., "In Vitro Reconstitution of Eukaryotic Ion Channels Using Droplet Interface Bilayers," *J. Am. Chem. Soc.*, 133:9370-9375 (2011).
Leunissen, M. E. et al., "Switchable Self-Protected Attractions in DNA-Functionalized Colloids," *Nat. Mater*, 8:590-595 (2009).
Levental, I., et al., "Soft Biological Materials and Their Impact on Cell Function," *Soft Matter*, 3:299-306 (2007).
Liang, H. Y., et al., "Growth, Geometry, and Mechanics of a Blooming Lily," *Proc. Natl. Acad. Sci. USA*, 108:5516-5521 (2011).
Lichtenberg, D. et al., "Effect of surface curvature on stability, thermodynamic behavior, and osmotic activity of dipalmitoylphosphatidylcholine single lamellarvesicles," *Biochemistry (Mosc.)*, 20:3462-3467 (1981).
Lindsey, H., et al., "Physicochemical characterization of 1,2-diphytanoyl-sn-glycero-3-phosphocholine in model membrane systems," *Biochim. Biophys. Acta*, 555:147-167 (1979).
Maglia, G. et al., "Analysis of single nucleic acid molecules with protein nanopores," *Method. Enzymol.* 475:591-623 (2010).
Maglia, G. et al., "Droplet networks with incorporated protein diodes show collective properties," *Nat. Nanotechn*,1(4):437-440 (2009).
Maglia, M. et al., "DNA strands from denatured duplexes are translocated through engineered protein nanopores at alkaline pH.," *Nano Lett.*, 9:3831-3836 (2009).
Mills, J. K., et al., "Lysolipid incorporation in dipalmitoylphosphatidylcholine bilayer membranes enhances the ion permeability and drug release rates at the membrane phase transition," *BBA-Biomembranes*, 1716:77-96 (2005).
Morisaku, T., et al., "Development of a new experimental system for monitoring biomembrane reactions: combinatin of laser spectroscopic techniques and biomembrane models formed at an oil/water interfacez," *Anal. Sci.*,20:1605-1608 (2004).
Nakagawa, S., et al., "Structural and functional studies of gap junction channels," *Curr. Opin. Struc. Biol.*, 20:423-430 (2010).
Naraghi, M., "T-jump study of calcium binding kinetics of calcium chelators," *Cell Calcium*, 22:255-268 (1997).
Nath, U., et al., "Genetic Control of Surface Curvature," *Science*, 299:1404-1407 (2003).

(56) References Cited

OTHER PUBLICATIONS

Needham, D., et al., "The development and testing of a new temperature-sensitive drug delivery system for the treatment of solid tumors," *Adv. Drug Deliver. Rev.*, 53:285-305 (2001).
Niculescu-Duvaz, I., et al., "Antibody-directed enzyme prodrug therapy (ADEPT): a review," *Adv. Drug Deliver. Rev.*, 26:151-172 (1997).
Noireaux, V., et al., "A Vesicle Bioreactor as a sStep Toward an Artificial Cell Assembly," *Proc. Natl. Acad. Sci. USA*, 101:17669-17674 (2004).
Noireaux, V., et al., "Development of an Artificial Cell, from Self-Organization to Computation and Self-Reproduction," *Proc. Natl. Acad. Sci., USA*, 108:3473-3480 (2011).
Okushima, S., et al., "Controlled production of monodisperse double emulsions by two-step droplet breakup in microfluidic devices," *Langmuir*, 20:9905-9908 (2004).
Payne, G. F., "Biopolymer-Based Materials: The Nanoscale Components and their Hierarchical Assembly," *Curr. Opin. Chem. Biol.*, 11:214-219 (2007).
Pays, K., et al., "Coalescence in Surfactant-Stabilized Double Emulsions", *Langmuir*, 17: 7758-7769 (2001).
Poulin et al., "Influence of the Alkyl Surfactant Tail on the Adhesion Between Emulsion Drops," *J. Phys. Chem. B*, 103(25)5157-5159 (1999).
Poulin, P., et al., "Adhesion of Water Droplets in Organic Solvent," *Langmuir*, 14: 6341-6343 (1998).
Poulos, J. L., et al., "Electrowetting on Dielectric-Based Microfluids for Integrated Lipid Bilayer Formation and Measurement," *Appl. Phys. Lett.*, 95:013706 (2009).
Pouponneau, P., et al., "Co-encapsulation of magnetic nanoparticles and doxorubicin into biodegradable microcarriers for deep tissue targeting by vascular MRI navigation," *Biomaterials*, 32:3481-3486 (2011).
Rautio, J et al., "Prodrugs: design and clinical applications," *Nat. Rev. Drug Discov.*, 7: 255-270 (2008).
Raychaudhuri, P., et al., "Fluorinated Amphiphiles Control the Insertion of α-Hemolysin Pores into Lipid Bilayers," *Biochemistry* 50:1599-1606 (2011).
Ringeisen, B. R., et al., "Jet-based methods to print living cells", *Biotechnology Journal*, 1:930-948 (2006).
Rojas, E., et al., "Temperature-Induced Protein Release from Water-in-Oil-in-Water", *Langmuir*, 24: 7154-7160 (2008).
Russew, M.-M., et al., "Photoswitches: From Molecules to Materials," *Adv. Mater*, 22: 3348-3360 (2010).
Sacanna, S., et al., Lock and Key Colloids, *Nature*, 464:575-578 (2010).
Sanjana, N. E., et al., "A fast flexible ink-jet printing method for patterning dissociated neurons in culture," *Journal of Neuroscience Methods*, 136(2):151-163 (2004).
Sapra, K. T., et al., "Lipid-coated hydrogel shapes as components of electrical circuits and mechanical devices," *Scientific Reports*, 2(848):1-9 (2012).
Sapra, K. T., et al., "Three dimensional construction of bilayer networks using shape encoded hydrogel," *Biophysical Journal*, 100(3):502a (2011).
Sarles, S. A., et al., "Bilayer Formation between Lipid-Encased Hydrogels Contained in Solid Substrates," *ACS Applied Materials & Interfaces*, 2(12):3654-3663 (2010).
Sarles, S. A., et al., "Biomolecular material systems with encapsulated interface bilayers," *MRS Proceedings*, 1301, (2011).
Sarles, S. A., et al., "Cell-inspired electroactive polymer materials incorporating biomolecular materials" *Proceedings of SPIE*, 7976:797626-1-797626-9 (2011).
Schrum, J. P., et al., "The Origins of Cellular Life," *Cold Spring Harb Perspect Biol 2*, pp. 1-16 (2010).
Schwille, P., "Bottom-Up Synthetic Biology:Engineering ina Tinkerer's World," *Science*, 333:1252-1254 (2011).
Seo, M. et al., "Microfluidic consecutive flow-focusing droplet generators," *Soft Matter* 3:986-992 (2007).

Sharon, E., et al., "Buckling Cascades in Free Sheets," *Nature*, 419: 579-579 (Oct. 10, 2002).
Sharon, E., et al., "Geometrically Driven Wrinkling Observed in Free Plastic Sheets and Leaves," *Phys. Rev. E*, 75, 7 pages (2007).
Shum, H. C. et al., "Multicompartment Polymersomes from Double Emulsions" *Angew. Chem. Int. Edit.*, 50: 1648-1651 (2011).
Sidorenko, A., et al., Reversible Switching of Hydrogel-Acutated Nanostructures into Complex Micropatterns, *Science*, 315: 487-490 (Jan. 26, 2007).
Skotheim, J. M. & Mahadevan, L., "Physical Limits and Design Principles for Plant and Fungal Movements," *Science*, 308: 1308-1310 (May 27, 2005).
Small, D. M., et al., "The Ionization Behavior of Fatty Acids and Bile Acids in Micelles and Membranes," *Hepatology*, 4: 77S-79S (1984).
Solé, R. V. et al., "Synthetic Protocell Biology: From Reproduction to Computation", *Philos. T. R. Soc. B*, 362: 1727-1739 (2007).
Stanley, C.E. et al., "A Microfluidic Approach for High-Throughput Droplet Interface Bilayer (DIB) Formation," *Chem Commun*, 46: 1620-1622 (2010).
Stoddart, D. et al., "Single-Nucleotide Discrimination in Immobilized DNA Oligonucleotides with a Biological Nanopore," *Proc. Natl. Acad. Sci. USA*, 106: 7702-7707 (May 12, 2009).
Strambio-De-Castillia, C. et al., "The Nuclear Pore Complex: Bridging Nuclear Transport and Gene Regulation," *Nat. Rev. Mol. Cell Bio.*, 11: 490-501 (Jul. 2010).
Lee, S., et al., Sensitivity of cationic surfactant templates to specific anions in liquid interface crystallization, Journal of Colloid and Interface Science, vol. 376, pp. 152-159 Mar. 11, 2012.
Syeda, R. et al., "Screening Blockers Against a Potassium Channel with a Droplet Interface Bilayer Array", *J. Am. Chem. Soc.*, 130: 15543-15548 (2008).
Synytska, A. et al., "Simple and Fast Method for the Fabrication of Switchable Bicomponent Micropatterned Polymer Surfaces," *Langmuir*, 23: 5205-5209 (2007).
Szostak, J.W., et al., "Synthesizing Life," *Nature*, 409: 387-390 (Jan. 18, 2001).
Tamaddoni, N. J. et al., "Fabricating Neuromast-Inspired Gel Structures for Membrane-Based Hair Cell Sensing," *Proceedings of SPIE*, vol. 8339: 833908-1-833908-11 (Apr. 3, 2012).
Theberge, A.B. et al., "Microdroplets in Microfluidics: an Evolving Platform for Discoveries in Chemistry and Biology," *Angew Chem. Int. Ed.*, 49: 5846-5868 (2010).
Tokarev, I. & Minko, S., "Stimuli-Responsive Porous Hydrogels at Interfaces for Molecular Filtration, Separation, Controlled Release, and Gating in Capsules and Membranes," *Adv. Mater*, 22: 3446-3462 (2010).
Torchilin, V. P., "Recent Advances with Liposomes as Pharmaceutical Carriers," *Nat. Rev. Drug Discov.*, 4: 145-160 (Feb. 2005).
Tsuchiya et al., "On-Chip Polymerase Chain Reaction Microdevice Employing a Magnetic Droplet-Manipulation System," *Sensors and Actuators B*, 130(2): 583-588 (2008).
Tuteja, A. et al., "Robust Omniphobic Surfaces," *Proc. Natl. Acad. Sci.*, 105: 18200-18205 (Nov. 25, 2008).
Ueno, M., et al., "Characteristics of the Membrane Permeability of Temperature-Sensitive Liposome," *Bull. Chem. Soc. Jpn.*, 64: 1588-1593 (1991).
Velev, O. D., et al., "On-Chip Manipulation of Free Droplets," *Nature*, 426: 515-516 (2003).
Villar, G., et al., "Formation of Droplet Networks that Function in Aqueous Environments," *Nat. Nanotechnol.*, 6: 803-808 (2011).
Walsh, C., "Molecular Mechanisms that Confer Antibacterial Drug Resistance," *Nature*, 406: 775-781 (Aug. 17, 2000).
Wang et al., "Controllable Microfluidic Production of Multicomponent Multiple Emulsions," RSC, *Lab Chip*, 11, 7 pages (2011).
Wang et al., "Liposomes in Double-Emulsion Glogules," *Langmuir*, 26(5): 3225-3231 (2010).
Weibel, D. B. & Whitesides, G.M., "Applications of Microfluidics in Chemical Biology," *Curr. Opin. Chem. Biol.*, 10: 584-591 (2006).
Wheeldon, I., et al., "Nanoscale Tissue Engineering: Spatial Control over Cell-Materials Interactions," *Nanotechnology*, 22: 212001, 16 pages (2011).

(56) References Cited

OTHER PUBLICATIONS

White, N. "Antimalarial Drug Resistance and Combination Chemotherapy," *Phil. Trans. R. Soc. Lond. B*, 354: 739-749 (1999).
Whitesides, G. M., "The Origins and the Future of Microfluidics," *Nature*, 442: 368-373 (Jul. 27, 2006).
Williamson, A. J., et al., "Templated Self-Assembly of Patchy Particles," *Soft Matter*, 7: 3423-3431 (2011).
Woolfson, D. N. & Bromley, E. H. C., "Synthetic Biology: a Bit of Rebranding, or Something New and Inspiring?" *Biochemist e-volution*, 33(1): 19-25 (Feb. 2011).
Wu, L.- Q. & Payne, G.F., *Biofabrication: Using Biological Materials and Biocatalysts to Construct Nanostructured Assemblies, Trends Biotechnol.*, 22(11): 593-599 (Nov. 2004).
Xu, G. & McLeod, H. L., "Strategies for Enzyme/Prodrug Cancer Therapy," *Clin. Cancer Res.*, 7: 3314-3324 (Nov. 2001).
Xu, J., et al., "Synthetic Protocells to Mimic and Test Cell Function," *Adv. Mater.* 22: 120-127 (2010).
Yamada, K. M. & Cukierman, E., "Modeling Tissue Morphogenesis and Cancer in 3D," *Cell*, 130: 601-610 (2007).
Yoo, J.-W. & Mitragotri, S., "Polymer Particles that Switch Shape in Response to a Stimulus," *Proc. Natl. Acad. Sci.*, 107(25): 11205-11210 (Jun. 22, 2010).
Yue, B. Y. et al., "Phospholipid Monolayers at Non-Polar Oil/Water Interfaces. Part 1—Phase Transitions in Distearoyl-lecithin Films at the n-Heptane Aqueous Sodium Chloride Interface," *J. Chem. Soc. Farad. T.*, 1(72): 2685-2693 (1976).
Zagnoni, M. et al., "A Microdroplet-Based Shift Register," *Lab Chip*, 10: 3069-3073 (2010).
Zelikin, A. N. et al., "Poly(Methacrylic Acid) Polymer Hydrogel Capsules: Drug Carriers, Sub-Compartmentalized Microreactors, Artificial Organelles," *Small*, 6(20): 2201-2207 (2010).
Zhu, J. & Marchant, R.E., "Design Properties of Hydrogel Tissue-Engineering Scaffolds," *Expert Rev. Med. Devices*, 8: 607-626 (2011).
Zimmerberg, J. & Kozlov, M. M., How Proteins Produce Cellular Membrane Curvature,: *Nat. Rev. Mol. Cell Bio*, 7: 9-19 (Jan. 2006).
European Search Report for European Patent Application No. 13 805 487.9, "Droplet Assembly by 3D Printing", Date of Completion: Jun. 21, 2016.
Non-Final Office Action for U.S. Appl. No. 14/354,706, "Multisomes: Encapsulated Droplet Networks" dated Sep. 9, 2016.
Non-Final Office Action for U.S. Appl. No. 14/438,345, "Hydrogel Network" dated Nov. 30, 2016.
Non-Final Office Action for U.S. Appl. No. 14/437,340, "Droplet Assembly Method" dated Nov. 4, 2016.
Non-Final Office Action for U.S. Appl. No. 14/649,394, "Droplet Assembly by 3D Printing" dated Nov. 8, 2017.
Final Office Action for U.S. Appl. No. 14/437,340, "Droplet Assembly Method" dated Dec. 6, 2017.
Office Action for U.S. Appl. No. 14/354,706, "Multisomes: Encapsulated Droplet Networks" dated Jul. 12, 2018.
Final Office Action for U.S. Appl. No. 14/649,394, "Droplet Assembly by 3D Printing" dated Jun. 29, 2018.
Office Action for U.S. Appl. No. 14/437,340, "Droplet Assembly Method" dated Sep. 10, 2018.
Final Office Action for U.S. Appl. No. 14/437,340, "Droplet Assembly Method" dated Apr. 5, 2019.
Office Action for U.S. Appl. No. 14/354,706, "Multisomes: Encapsulated Droplet Networks" dated May 1, 2019.
Office Action for U.S. Appl. No. 14/649,394, "Droplet Assembly by 3D Printing", dated May 6, 2019.
Office Action for U.S. Appl. No. 15/788,441, "Hydrogel Network", dated May 14, 2019.
Notice of Allowance for U.S. Appl. No. 14/354,706, "Multisomes: Encapsulated Droplet Networks", dated Sep. 18, 2019.
Office Action for U.S. Appl. No. 14/437,340, "Droplet Assembly Method" dated Oct. 22, 2019.
Final Office Action for U.S. Appl. No. 15/788,441, "Hydrogel Network", dated Nov. 15, 2019.
Final Office Action for U.S. Appl. No. 14/649,394, "Droplet Assembly by 3D Printing", dated Nov. 21, 2019.
Final Office Action for U.S. Appl. No. 14/437,340 "Droplet Assembly Method" dated Apr. 30, 2020.
Office Action for U.S. Appl. No. 15/788,441, "Hydrogel Network", dated May 27, 2020.
Ex Parte Quayle Office Action for U.S. Appl. No. 14437340, "Droplet Assembly Method", dated Oct. 14, 2020.
Notice of Allowance for U.S. Appl. No. 14437340, "Droplet Assembly Method", dated Nov. 3, 2020.
Notice of Allowance for U.S. Appl. No. 15/788,441, "Hydrogel Network" dated Dec. 9, 2020.
Supplemental Notice of Allowability for U.S. Appl. No. 15/788,441, "Hydrogel Network" dated Jan. 13, 2021.
Office Action for U.S. Appl. No. 14/649,394 "Droplet Assembly by 3D Printing" dated Dec. 10, 2020.
Office Action for U.S. Appl. No. 16/721,302 "Multisomes: Encapsulated Droplet Networks" dated Mar. 3, 2021.
Final Office Action U.S. Appl. No. 16/721,302 "Multisomes: Encapsulated Droplet Networks" dated Oct. 28, 2021.
Notice of Allowance for U.S. Appl. No. 14/649,394, "Droplet Assembly by 3D Printing" dated Aug. 17, 2021.
Notice of Allowance for U.S. Appl. No. 16/721,302 "Multisomes: Encapsulated Droplet Networks" dated Mar. 30, 2022.
Non-Final Office Action for U.S. Appl. No. 17/165,252, "Droplet Assembly Method" dated Jul. 21, 2023.

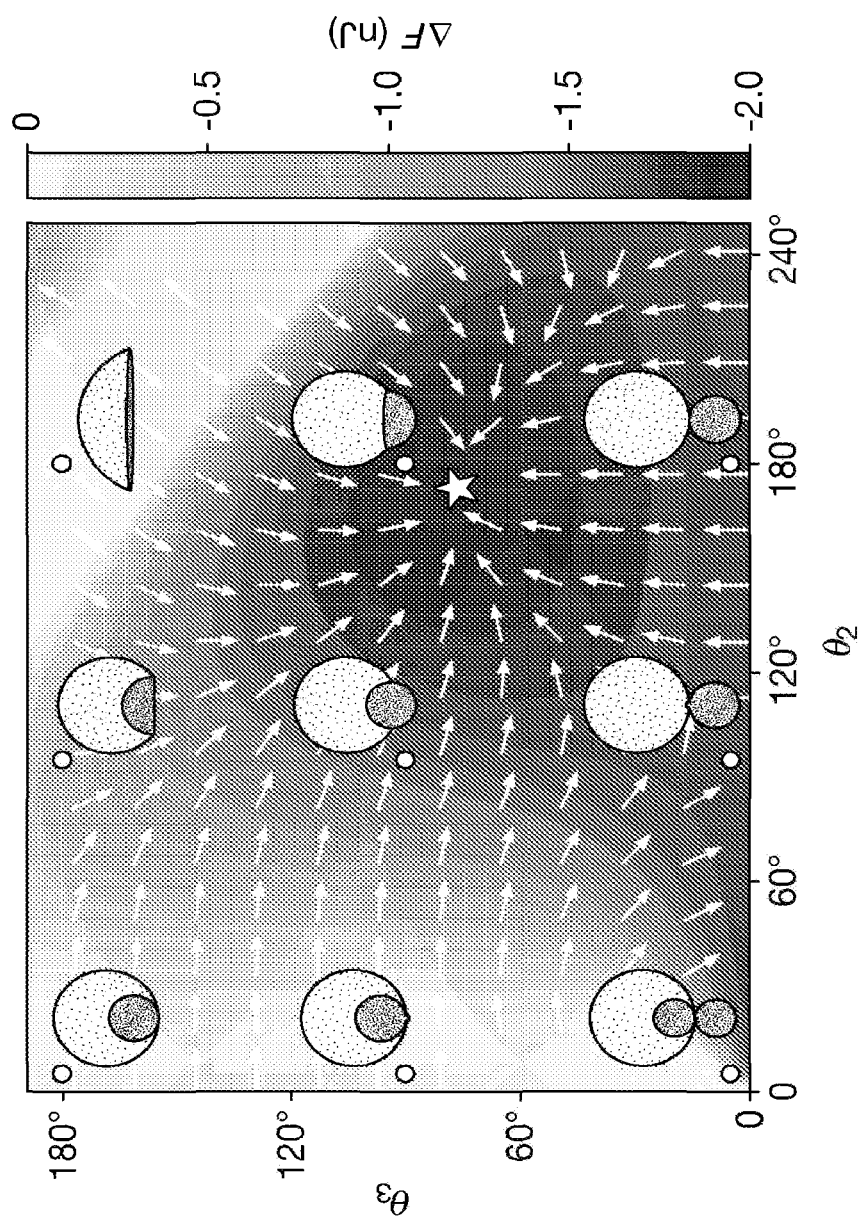
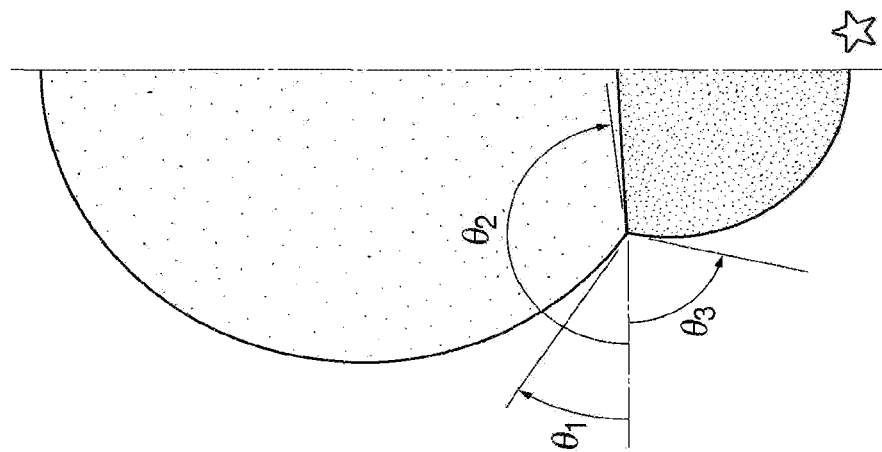
FIG. 2A
FIG. 2B

MULTISOMES: ENCAPSULATED DROPLET NETWORKS

RELATED APPLICATIONS

This application is a continuation of U.S. application Ser. No. 16/721,302, filed on Dec. 19, 2019, which is a continuation of U.S. application Ser. No. 14/354,706, filed on Apr. 28, 2014, now U.S. Pat. No. 10,548,852, issued on Feb. 4, 2020 which is the U.S. National Stage of International Application No. PCT/GB2012/052736, filed on Nov. 2, 2012, published in English, which claims priority under 35 U.S.C. § 119 or 365 to Great Britain, Application No. 1119032.9, filed on Nov. 3, 2011, and which claims the benefit of U.S. Provisional Application No. 61/592,062, filed on Jan. 30, 2012. The entire teachings of the above applications are incorporated herein by reference.

GOVERNMENT SUPPORT

This invention was made with government support under Grant No. HG003709 from the National Institutes of Health (NIH). The government has certain rights in the invention.

FIELD OF THE INVENTION

The invention relates to droplet encapsulates, which are also referred to herein as "multisomes", and to compositions comprising the droplet encapsulates. The invention also provides processes for preparing the droplet encapsulates. Various uses of the droplet encapsulates are also described, including their use as drug delivery vehicles, in synthetic biology, and in the study of membrane proteins.

BACKGROUND TO THE INVENTION

An aqueous droplet made in a solution of lipids in oil acquires a lipid monolayer coat, and two such droplets brought into contact form a lipid bilayer at their interface, called a droplet interface bilayer (DIB) (Funakoshi, K. et al. Anal. Chem. 78, 8169-8174 (2006); Holden, M. A. et al. J. Am. Chem. Soc. 129, 8650-8655 (2007)). Similarly, a flat hydrogel support may be used in place of one of the droplets to form a droplet-on-hydrogel bilayer (DHB) (Heron, A. J. et al. J. Am. Chem. Soc. 129, 16042-16047 (2007)). DIBs and DHBs have proved remarkably stable platforms for electrical or optical measurements on single membrane proteins (Holden, M. A. et al., J. Am. Chem. Soc. 129, 8650-8655 (2007); Heron, A. J. et al. J. Am. Chem. Soc. 129, 16042-16047 (2007); Syeda, R. et al., J. Am. Chem. Soc. 130, 15543-15548 (2008); Heron, A. J. et al. J. Am. Chem. Soc. 131, 1652-1653 (2009)). Besides the utility of individual interface bilayers in biophysical measurements, functional networks of droplets joined by DIBs can be constructed that exploit a variety of membrane pumps, channels and pores to act as light sensors, batteries, and electrical devices (Holden, M. A. et al., J. Am. Chem. Soc. 129, 8650-8655 (2007); Maglia, G. et al. Nat. Nanotechnol. 4, 437-440 (2009)). While droplet networks provide a means to build functional devices, they have suffered from an important constraint: the droplets must be surrounded by a bulk oil phase, precluding their use in physiological and other aqueous environments.

SUMMARY OF THE INVENTION

The inventors have now provided encapsulated aqueous droplet networks which do not require a bulk oil phase and are stable in aqueous and other hydrophilic environments. Aqueous droplets and droplet networks, which are bounded by amphiphilic molecules, have been stabilised by encapsulating them within small drops of a hydrophobic medium. The resulting droplet encapsulates, which are also referred to herein as "multisomes", can communicate with the external environment through membrane proteins. In addition, membrane proteins allow multiple droplets within the same multisome to communicate with each other. This in principle allows multisomes to sense their environment, process information, and contingently deliver materials to the surroundings. Multiple droplets within the same droplet encapsulate can also release their contents into the environment simultaneously, e.g. after a decrease in pH or an increase in temperature, which provides a useful method for the combinatorial delivery of drugs. Further applications of multisomes range from providing a novel platform for the fundamental study of membrane proteins, to acting as multicompartment protocellular chassis for "bottom-up" synthetic biology.

Accordingly, in a first aspect, the invention provides a droplet encapsulate comprising:
  a drop of a hydrophobic medium;
  a peripheral layer of non-polymeric amphipathic molecules around the surface of the drop; and
  an aqueous droplet within the peripheral layer, the aqueous droplet comprising: (a) an aqueous medium and (b) an outer layer of non-polymeric amphipathic molecules around the surface of the aqueous medium.

The peripheral and outer layers may together form a bilayer of said non-polymeric amphipathic molecules at an interface between the aqueous droplet and the peripheral layer.

In a second aspect, the invention provides a process for producing a droplet encapsulate, which droplet encapsulate comprises:
  a drop of a hydrophobic medium;
  a peripheral layer of non-polymeric amphipathic molecules around the surface of the drop; and
  an aqueous droplet within the peripheral layer, the aqueous droplet comprising: (a) an aqueous medium and (b) an outer layer of non-polymeric amphipathic molecules around the surface of the aqueous medium;
  which process comprises:
  transferring an aqueous droplet, which aqueous droplet comprises (a) an aqueous medium and (b) an outer layer of non-polymeric amphipathic molecules around the surface of the aqueous medium, into a drop of a hydrophobic medium, which drop has a peripheral layer of non-polymeric amphipathic molecules around its surface.

The invention further provides a droplet encapsulate which is obtainable by a process of the second aspect of the invention as defined above.

In a third aspect, the invention provides a process for producing a droplet encapsulate, which droplet encapsulate comprises:
  a drop of a hydrophobic medium;
  a peripheral layer of non-polymeric amphipathic molecules around the surface of the drop; and
  an aqueous droplet within the peripheral layer, the aqueous droplet comprising: (a) an aqueous medium and (b) an outer layer of non-polymeric amphipathic molecules around the surface of the aqueous medium;
  which process comprises:
  (i) introducing a drop of a hydrophobic medium into a hydrophilic carrier, in the presence of non-polymeric amphipathic molecules, thereby producing a drop of a hydrophobic medium and a peripheral layer of the non-polymeric amphipathic molecules around the surface of the drop;

(ii) introducing a droplet of an aqueous medium into a hydrophobic medium in the presence of non-polymeric amphipathic molecules, thereby producing an aqueous droplet within the hydrophobic medium, said aqueous droplet comprising: (a) said aqueous medium and (b) an outer layer of said non-polymeric amphipathic molecules around the surface of the aqueous medium;

wherein steps (i) and (ii) can be performed in either order or at the same time; and (iii) transferring the aqueous droplet produced in step (ii) into the drop of hydrophobic medium produced in step (i), thereby producing said droplet encapsulate.

The invention further provides a droplet encapsulate which is obtainable by a process of the third aspect of the invention as defined above.

The droplet encapsulates of the invention can also be produced using microfluidic techniques, which may for instance employ consecutive shearing or flow focusing microfluidic devices.

Thus, in a further aspect, the invention provides a process for producing a droplet encapsulate, which process comprises:

(i) introducing a droplet of aqueous medium from a first channel of a microfluidic device, which first channel contains said aqueous medium, into a second channel of the microfluidic device, which second channel contains a hydrophobic medium, wherein the aqueous medium in the first channel, or the hydrophobic medium in the second channel, or both, further comprise non-polymeric amphipathic molecules, thereby producing in the second channel an aqueous droplet within the hydrophobic medium, said aqueous droplet comprising: (a) said aqueous medium and (b) an outer layer of said non-polymeric amphipathic molecules around the surface of the aqueous medium; and (ii) introducing a drop of said hydrophobic medium from the second channel, which drop of hydrophobic medium comprises the aqueous droplet, into a third channel of the microfluidic device, wherein the third channel contains a hydrophilic carrier, wherein the hydrophobic medium in the second channel, or the hydrophilic carrier in the third channel or both, further comprise non-polymeric amphipathic molecules, thereby producing in the third channel a droplet encapsulate within the hydrophilic carrier, the droplet encapsulate comprising:

the drop of said hydrophobic medium;
a peripheral layer of non-polymeric amphipathic molecules around the surface of the drop; and
said aqueous droplet within said peripheral layer.

The invention further provides a droplet encapsulate which is obtainable by a process of the further aspect of the invention as defined above.

In yet another aspect, the invention provides a composition comprising: a droplet encapsulate of the invention as defined above, and a hydrophilic carrier. The composition may comprise a plurality of droplet encapsulates of the invention and said hydrophilic carrier.

The droplet encapsulates of the invention may comprise one or more bioactive agents, for instance therapeutic and/or diagnostic agents, and, as mentioned above, are useful as drug delivery vehicles.

Accordingly, in another aspect, the invention provides a droplet encapsulate of the invention as defined above, which further comprises a therapeutic agent, for use in a method for treatment of the human or animal body by therapy.

In yet another aspect, the invention provides a droplet encapsulate of the invention as defined above, which further comprises a diagnostic agent, for use in a diagnostic method practised on the human or animal body.

In yet another aspect, the invention provides a composition of the invention as defined above, wherein the droplet encapsulate further comprises a therapeutic agent, for use in a method for treatment of the human or animal body by therapy.

Also provided is a composition of the invention as defined above, wherein the droplet encapsulate further comprises a diagnostic agent, for use in a diagnostic method practised on the human or animal body.

Further applications of multisomes include providing a platform for the fundamental study of membrane proteins. As will be explained further below, the droplet encapsulate of the invention may comprise a bilayer of non-polymeric amphipathic molecules. In particular, part of the outer layer of the aqueous droplet in the encapsulate may contact the peripheral layer to form a bilayer of non-polymeric amphipathic molecules at an interface between the aqueous droplet and the peripheral layer. Additionally or alternatively, more than one aqueous droplet may be present in the encapsulate, and part of the outer layer of one aqueous droplet may contact part of the outer layer of another aqueous droplet to form a bilayer of non-polymeric amphipathic molecules at an interface between the two droplets. Also, more than one aqueous droplet may form a bilayer with the peripheral layer. In this way, the droplet encapsulate of the invention may comprise one or more bilayers of non-polymeric amphipathic molecules. In some embodiments, the droplet encapsulate comprises multiple bilayers of non-polymeric amphipathic molecules. The or each bilayer in the droplet encapsulate of the invention is capable of accommodating one or more membrane proteins, thus the droplet encapsulate of the invention can provide a useful platform for the fundamental study of membrane proteins, including for instance protein pores, protein channels or protein pumps, receptors, and proteins which effect cell recognition or a cell-to-cell interaction. The or each bilayer in the encapsulate may comprise a plurality of membrane proteins, for instance multiple copies of the same membrane protein or two or more different classes of membrane protein. Accordingly, the invention provides the use of a droplet encapsulate of the invention as defined above as a research tool for the study of membrane proteins.

The invention further provides the use of a droplet encapsulate of the invention as defined herein in a method of investigating and/or screening a membrane protein.

In another aspect, the invention provides the use of a droplet encapsulate of the invention as defined herein in a method of investigating and/or screening an analyte which interacts with a membrane protein.

In another aspect the invention provides the use of a droplet encapsulate of the invention as defined herein in a method of investigating and/or screening a bilayer of non-polymeric amphipathic molecules.

In another aspect the invention provides the use of a first droplet encapsulate of the invention as defined above and a second droplet encapsulate of the invention as defined above, for investigating and/or screening a membrane protein complex which spans two bilayers of said non-polymeric amphipathic molecules, wherein in each of said first and second droplet encapsulates, a said aqueous droplet is situated at the edge of the drop, wherein part of the outer layer of the aqueous droplet contacts said peripheral layer, thereby forming a bilayer of said non-polymeric amphipathic molecules at an interface between the aqueous droplet and the peripheral layer, and wherein said first and second droplet encapsulates are positioned such that the bilayer of the first droplet encapsulate and the bilayer of the second droplet encapsulate are apposed, wherein a membrane protein complex spans said two apposed bilayers.

By using membrane proteins and multiple droplets, multisomes can sense their environment, process information, and contingently deliver materials to the surroundings, as illustrated in FIG. 1A hereinbelow.

Thus, in a further aspect, the invention provides the use of a droplet encapsulate of the invention as defined above for trafficking a molecule between droplets in the encapsulate.

The invention also provides the use of a droplet encapsulate of the invention as defined above for delivering a molecule from a droplet in the encapsulate to the external environment.

The invention also provides the use of a droplet encapsulate of the invention as defined above for exchanging materials between encapsulated droplets and the environment.

In yet another aspect, the invention provides the use of a droplet encapsulate of the invention as defined above as a sensor. For instance the droplet encapsulate may be used as a light sensor or a sensor for the presence of a target analyte.

Networks of droplets can be constructed within multisomes to exploit a variety of membrane pumps, channels and pores to act as light sensors, batteries, and electrical devices.

Accordingly, the invention also provides the use of droplet encapsulate of the invention as defined above as a sensor, battery, or electrical device.

Further provided is a sensor, a battery, or an electrical device, comprising a droplet encapsulate of the invention as defined above.

The droplet encapsulate of the invention can also act as a multi-compartment protocellular chassis for "bottom-up" synthetic biology.

Accordingly, in another aspect, the invention provides the use of a droplet encapsulate of the invention as defined above in synthetic biology.

The invention also provides the use of a composition of the invention as defined above in synthetic biology.

In yet another aspect, the invention provides the use of a droplet encapsulate of the invention as defined above to prepare a protocell.

The invention also provides the use of a droplet encapsulate of the invention as defined above to prepare an aggregate of protocells. An aggregate of protocells may also be referred to as prototissue.

Further provided is the use of a composition of the invention as defined above to prepare a protocell.

In another aspect, the invention provides the use of a composition of the invention as defined above to prepare an aggregate of protocells.

In another aspect, the invention provides a method of preparing a protocell, the method comprising:

providing a droplet encapsulate of the invention as defined above; and allowing the outer layer of the aqueous droplet to come into contact with said peripheral layer of non-polymeric amphipathic molecules, or bringing the outer layer of the aqueous droplet into contact with said peripheral layer of non-polymeric amphipathic molecules, and thereby forming a bilayer of non-polymeric amphipathic molecules around at least part of the surface of the aqueous droplet.

Bilayer formation may optionally be aided by removing some or all of the hydrophobic medium from the droplet encapsulate of the invention. Thus, in one embodiment, the method of preparing a protocell comprises: removing some or all of the hydrophobic medium from a droplet encapsulate of the invention as defined above, so that said peripheral layer of non-polymeric amphipathic molecules sticks to the outer layer of said aqueous droplet, thereby forming a bilayer of non-polymeric amphipathic molecules around at least part of the surface of the aqueous droplet.

In another aspect, the invention provides a protocell which is obtainable by the method of the invention as defined above for preparing a protocell.

In another aspect, the invention provides a protocell comprising a droplet encapsulate of the invention as defined above, wherein said peripheral layer of non-polymeric amphipathic molecules contacts the outer layer of said aqueous droplet and thereby forms a bilayer of non-polymeric amphipathic molecules around part of the aqueous droplet.

In another aspect, the invention provides a method of preparing a prototissue, which prototissue comprises an aggregate of protocells, which method comprises:

providing a droplet encapsulate of the invention as defined above which comprises a plurality of said aqueous droplets; and allowing the outer layers of the aqueous droplets to come into contact with said peripheral layer of non-polymeric amphipathic molecules, or bringing the outer layers of the aqueous droplets into contact with the peripheral layer of non-polymeric amphipathic molecules, and thereby forming a bilayer of non-polymeric amphipathic molecules around at least part of the surface of the plurality of aqueous droplets.

Bilayer formation may optionally be aided by removing some or all of the hydrophobic medium from the droplet encapsulate of the invention. Thus, in one embodiment, the method of preparing a prototissue comprises: removing some or all of the hydrophobic medium from a droplet encapsulate of the invention as defined above which comprises a plurality of said aqueous droplets, so that the peripheral layer of non-polymeric amphipathic molecules sticks to the outer layers of said aqueous droplets, thereby forming a bilayer of non-polymeric amphipathic molecules around at least part of the surface of the plurality of aqueous droplets.

In another aspect, the invention provides a prototissue which is obtainable by the method of the invention as defined above for preparing a prototissue.

In another aspect, the invention provides a prototissue comprising a droplet encapsulate of the invention as defined above, which droplet encapsulate comprises a plurality of said aqueous droplets, wherein the peripheral layer of non-polymeric amphipathic molecules contacts the outer layers of said aqueous droplets, thereby forming a bilayer of said non-polymeric amphipathic molecules around at least part of the surface of the plurality of aqueous droplets.

In another aspect, the invention provides a prototissue comprising a plurality of protocells of the invention as defined above.

BRIEF DESCRIPTION OF THE FIGURES

FIG. 1A is a schematic illustration showing aqueous droplets encapsulated in an oil droplet; the aqueous droplets are separated from each other by lipid bilayers, allowing communication within the network through membrane proteins, for instance protein pores, channels or pumps; bilayers are also present at the surfaces of the aqueous droplets that protrude from the oil droplet enabling the network to communicate with the bulk solution. The multisome shown is capable of sensing its environment, processing the information, and then contingently delivering materials to the environment. The sensing and delivery capabilities are demonstrated in the Examples herein.

FIG. 1B is a schematic illustration of an encapsulated two-droplet network, illustrating the lipid monolayers and bilayers in the multisomes of the invention.

FIGS. 1C, 1D and 1E are photographs of multisomes containing one, two and three inner droplets, respectively. The oil droplets were suspended on wire loops to allow extended study. The aqueous droplets were dyed with 25 μM sulforhodamine 101 (red) or fluorescein (green). Scale bars represent 400 μm.

FIG. 2A shows a definition of the contact angles $\theta_1$, $\theta_2$ and $\theta_3$ for an encapsulated droplet, relative to the horizontal, whose geometry has been calculated computationally as described in Example 1.

FIG. 2B shows the calculated free energy of bilayer formation as a function of the contact angles $\theta_2$ and $\theta_3$, for the parameter values given in Example 1. Arrows indicate the direction of steepest descent. The geometry of the encapsulated droplet at the nine points on the landscape marked by red circles is illustrated adjacent to each point. The most stable state as determined by the calculation, marked on the landscape by a star, is depicted in FIG. 2A.

FIG. 3A is a schematic illustration of measurement of ionic current flowing between an encapsulated droplet and the bulk aqueous solution, through an αHL pore inserted in the bilayer.

FIG. 3B shows stepwise increases in current indicating consecutive insertions of wild-type (WT) αHL pores into the bilayer separating the encapsulated droplet from the bulk aqueous solution. The current levels (corresponding to peaks in the current histogram) were separated by 18.6±0.8 pA (mean±s.d., n=16), which is the expected current for a single αHL pore. Only a sample of the data is shown. Measurements were taken at +50 mV in 500 mM KCl.

FIG. 3C shows current blockades of a single WT αHL pore after adding ~10 μM γ-cyclodextrin (γCD) to the bulk solution. Indicated are the current levels of the unoccupied pore, the pore with γCD bound, and the zero current level. The γCD current blockades had an amplitude of 63.7±2.0% (mean±s.d., n=673), and a dissociation rate of 4.0±0.6 s$^{-1}$ (mean±s.d.) consistent with previous studies. Only a sample of the data is shown. Measurements were taken at −50 mV in 1 M KCl.

FIG. 4A shows the results of fluorescence measurements of two multisomes, each with a single inner droplet, in the same bulk solution. Both inner droplets contained dextran-conjugated fluo-4, and one contained αHL. The oil and inner droplets are outlined where they are invisible in the photographs, and are respectively labelled 'Oil' and 'Dye'. Following the addition of $Ca^{2+}$ to the external solution, an increase in fluorescence was observed in the droplet containing αHL, while fluorescence remained negligible for the droplet without protein. The scale bar represents 300 μm.

FIG. 4B shows the results of fluorescence measurements of an encapsulated two-droplet network, in which one droplet contained $Ca^{2+}$ and the other contained dextran-conjugated fluo-4 and αHL; these droplets are respectively labelled '$Ca^{2+}$' and 'Dye'. An increase in fluorescence was observed only in the dye-containing droplet. The scale bar represents 300 μm.

FIG. 5A is a schematic illustration of an experiment demonstrating the pH sensitivity of an encapsulated two-droplet network made with a mixture of 1,2-dioleoyl-sn-glycero-3-phosphoethanolamine (DOPE) and oleic acid (OA). One droplet contained $Ca^{2+}$ and the other contained dextran-conjugated fluo-4. Upon lowering the pH of the external aqueous buffer from 8.0 to 5.5, both droplets burst, releasing their contents into the bulk aqueous solution, where they mixed to produce a fluorescent signal.

FIG. 5B shows the results of the fluorescence measurements from the experiment illustrated in FIG. 5A. The oil and the inner droplets, containing $Ca^{2+}$ or fluo-4 are outlined, and respectively labelled 'Oil', '$Ca^{2+}$' and 'Dye'. After lowering the pH of the external solution, both droplets burst simultaneously. This first caused a slight decrease in fluorescence intensity as the contents of the dye droplet were diluted, then a sharp increase in intensity as the fluo-4 solution mixed with the $Ca^{2+}$ solution. Finally, the intensity decreased as the mixture became diluted into the bulk aqueous phase. Scale bar represents 500 μm.

FIG. 6A shows the bursting temperatures of multisomes with a single inner droplet subjected to a temperature ramp (top: the temperature was increased from room temperature at a rate of ~1° C. mint bottom: histogram of bursting temperatures). The bursting temperature was 43.6±3.5° C. (mean±s.d., n=93), excluding the three multisomes that burst below 35° C.

FIG. 6B shows the bursting times of multisomes with a single inner droplet held at a constant temperature of 37.2±0.4° C. The top schematic provides the temperature profile. The bottom graph shows the proportion of multisomes that burst within 30 min of reaching 37° C., showing that 93% of multisomes survived for at least 30 min at this temperature (n=46).

DETAILED DESCRIPTION OF THE INVENTION

Figure 1A:
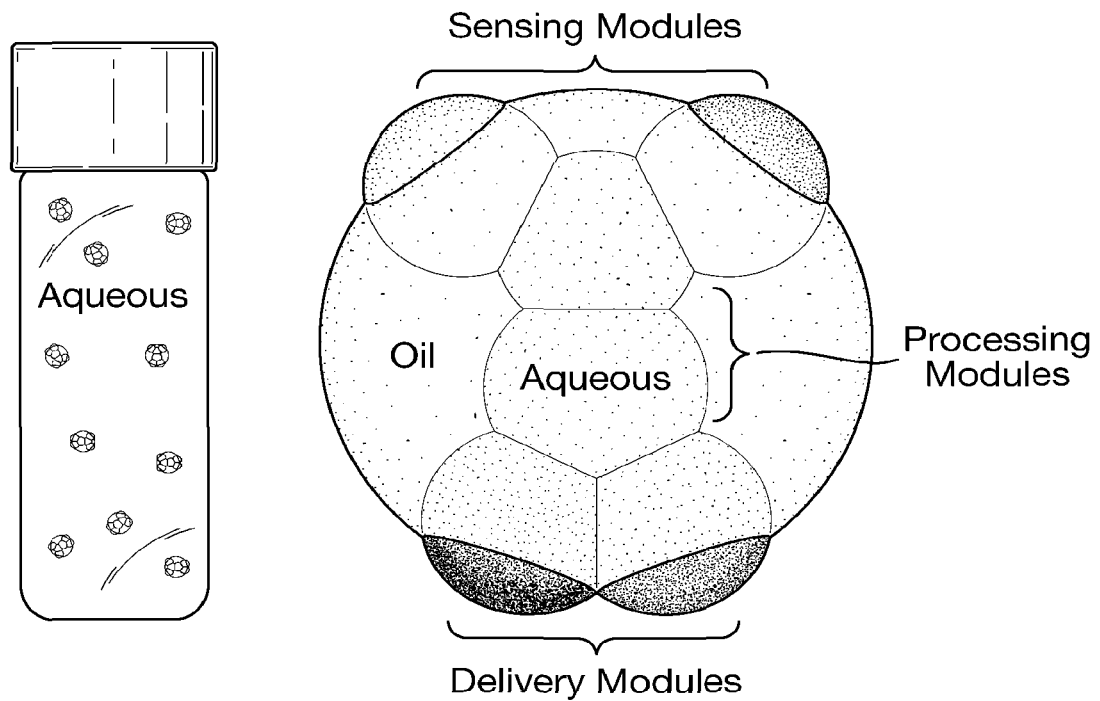
FIGS. 1A-E contain schematic illustrations and photographs of multisomes of the invention. Thus.
Figure 1B:
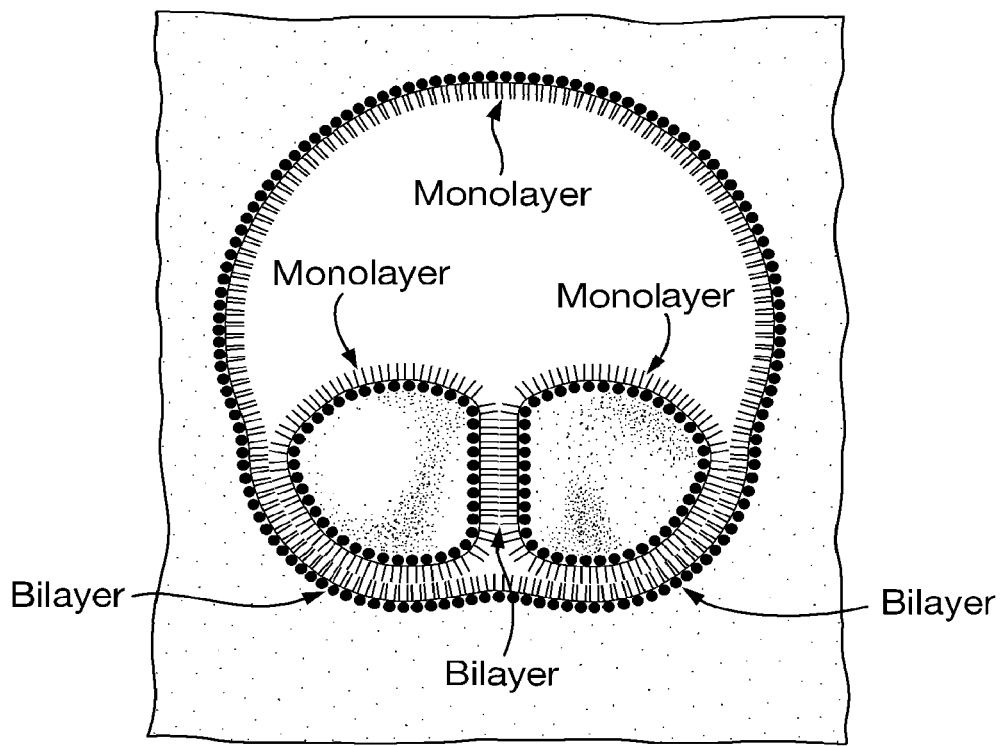

The droplet encapsulate of the invention is also referred to herein as a "multisome", irrespective of whether only one or a plurality of aqueous droplets are encapsulated within the peripheral layer. Thus, the terms "droplet encapsulate" and "multisome", as used herein, both refer to synthetic structures which contain one or more encapsulated droplets. In the present invention, one or more aqueous droplets are encapsulated within a peripheral layer of non-polymeric amphipathic molecules, which layer is located around the surface of a hydrophobic drop. The or each aqueous droplet comprises (a) an aqueous medium and (b) an outer layer of non-polymeric amphipathic molecules around the surface of the aqueous medium. The one or more aqueous droplets are also fully or partially within the hydrophobic drop itself. Thus, an aqueous droplet may be fully within the hydrophobic drop, completely surrounded by the hydrophobic medium. Alternatively, it may be at or near the edge of the drop, in contact with the peripheral layer, so that the outer and peripheral layers adhere to form a bilayer as shown in FIGS. 1b to 1e. The latter arrangement, where the aqueous droplet is at or near the edge of the drop so that the outer layer forms a bilayer with the peripheral layer, is thought to be thermodynamically more stable.

The droplet encapsulate of the invention is synthetic. Thus, the droplet encapsulate of the invention may be referred to as a synthetic droplet encapsulate.

The droplet encapsulate of the invention comprises a drop of a hydrophobic medium; a peripheral layer of non-polymeric amphipathic molecules around the surface of the drop; and an aqueous droplet within the peripheral layer. The aqueous droplet comprises an aqueous medium and an outer layer of non-polymeric amphipathic molecules around the surface of the aqueous medium.

The non-polymeric amphipathic molecules are typically arranged around the surface of the hydrophobic drop in a monolayer, and the outer layer of the or each aqueous droplet in the multisome typically comprises a monolayer of the non-polymeric amphipathic molecules. However, bilayers of the non-polymeric amphipathic molecules may be formed at the interfaces when the or each aqueous droplet adheres to the surface of the hydrophobic drop, and indeed when aqueous droplets adhere to each other (see FIGS. 1C-1E).

Thus, the peripheral layer typically comprises a monolayer of the non-polymeric amphipathic molecules.

Usually, the outer layer of non-polymeric amphipathic molecules around the surface of the aqueous medium comprises a monolayer of the non-polymeric amphipathic molecules.

Typically, the peripheral layer comprises a monolayer of the non-polymeric amphipathic molecules and said outer layer comprises a monolayer of the non-polymeric amphipathic molecules.

In some embodiments of the droplet encapsulate of the invention, particularly when the encapsulate is first synthesised and the aqueous droplet has not yet had time to adhere to the peripheral layer to form a thermodynamically more stable structure, the aqueous droplet will be located fully within the hydrophobic drop; the outer layer of non-polymeric amphipathic molecules will not in such cases be in contact with the peripheral layer, but will usually only be in contact with the hydrophobic medium.

In one embodiment, therefore, the aqueous droplet is situated inside the drop and said outer layer of non-polymeric amphipathic molecules is not in contact with the peripheral layer. Generally, in this embodiment, the outer layer of non-polymeric amphipathic molecules contacts the hydrophobic medium.

Typically, however, the droplet encapsulate of the invention comprises at least one bilayer of non-polymeric amphipathic molecules. Usually, for instance, the peripheral layer of the droplet encapsulate and the outer layer of the aqueous droplet are capable of together forming a bilayer of the non-polymeric amphipathic molecules at an interface between the aqueous droplet and the peripheral layer. Additionally or alternatively, the outer layer of the aqueous droplet may form a bilayer with the outer layer of a further aqueous droplet in the droplet encapsulate.

Thus, in some embodiments, the aqueous droplet is situated at the edge of the drop, wherein part of the outer layer of the aqueous droplet contacts said peripheral layer, thereby forming a bilayer of said non-polymeric amphipathic molecules at an interface between the aqueous droplet and the peripheral layer. Typically in such embodiments, a different part of the outer layer contacts the hydrophobic medium. A photograph of an example of such an arrangement is shown in FIG. 1C. Such an arrangement is also illustrated schematically in FIG. 1B, in a case where two aqueous droplets are present. Such arrangements are found to be kinetically stable.

The bilayer at the interface between the aqueous droplet and the peripheral layer may further comprise a membrane protein. The membrane protein may be of any type. The use of integral membrane proteins has been demonstrated, but it is equally expected that peripheral membrane proteins could be used. The membrane protein may for instance be a membrane pump, channel and/or pore, to allow for precise control over the exchange of material, and electrical communication, between the droplet and the external solution. The membrane protein could for instance be an αHL pore. However, any suitable membrane protein can be used including the two major classes that is β-barrels or α-helical bundles. An important application is a membrane protein which is a pore or a channel. Besides a protein pore or channel, further possible membrane proteins include, but not exclusively, a receptor, a transporter or a protein which effects cell recognition or a cell-to-cell interaction. The bilayer at the interface between the aqueous droplet and the peripheral layer, and indeed any other bilayer in the droplet encapsulate, may comprise more than one membrane protein. For instance, a particular bilayer may contain multiple copies of the same membrane protein, or two or more different classes of membrane proteins. Where more than one class is present, the bilayer may contain multiple copies of each different class.

Suitable membrane proteins which allow for exchange of materials and electrical communication are known and readily available to the skilled person; many such proteins are either commercially available or can be prepared by known methods. For instance, WT αHL monomers can be prepared by in vitro transcription-translation (IVTT), and heptamerised by incubation with rabbit red blood cell membranes. The heptamers are typically purified by sodium dodecyl sulphate polyacrylamide gel electrophoresis (SDS-PAGE) (Maglia, G. et al. Method. Enzymol. 475, 591-623, 2010). Also, Bayley, H. et al. Droplet interface bilayers. *Mol. BioSyst.* 4, 1191-1208 (2008) lists several proteins that were tested for insertion into droplet interface bilayers made in bulk oil.

The droplet encapsulate of the invention may comprise a plurality of the aqueous droplets within the peripheral layer. Each aqueous droplet comprises: (a) a said aqueous medium, and (b) a said outer layer of non-polymeric amphipathic molecules around the surface of the aqueous medium. The outer layer of each aqueous droplet typically comprises a monolayer of the non-polymeric amphipathic molecule. However, bilayers of the non-polymeric amphipathic molecules may be formed at the interfaces when the or each aqueous droplet adheres to the inside of the peripheral layer around the hydrophobic drop, or indeed when aqueous droplets adhere to each other.

The number of said aqueous droplets in the droplet encapsulate which comprises a plurality of the droplets may be denoted n, where n is equal to or greater than 2. An embodiment in which n is 2 is illustrated schematically in FIG. 1B and a photograph of such an embodiment is shown in FIG. 1D. In some embodiments, n is an integer equal to or greater than 3. A photograph of an embodiment in which n is 3 is shown in FIG. 1E, and an embodiment in which n is 6 is illustrated schematically in FIG. 1A.

The integer n can in principle be very high, for instance in the order of millions. This is because the aqueous droplets may be very small and there is no upper limit on the size of the hydrophobic drop. Also, as explained further below, the droplet encapsulates of the invention may include large networks of aqueous droplets. Such networks, which can in principle comprise millions of droplets, are useful for preparing prototissue (i.e. an aggregate of protocells). In some embodiments, therefore, the integer n may be as high as several million, for instance up to about 10,000,000, or for instance up to about 5,000,000.

In other embodiments, n may be several hundred, for instance up to about 500, or for instance up to about 400. Indeed, multisomes made by the manual pipetting method used in the present Examples typically have an external diameter of about ~1 mm, and aqueous droplets can easily be made manually down to ~100-μm diameter. Thus, about 500 such aqueous droplets could fit in a 1 mm sphere, or perhaps up to ~25% less than this due to packing constraints (although this depends on the droplets' compositions). Thus, in some embodiments the integer n may be up to about 500, or for instance up to about 400.

The integer n may for instance be an integer of from 2 to 500, or an integer of from 3 to 500. n may be an integer of from 2 to 400. In other embodiments, n may be an integer of from 2 to 300, or an integer of from 3 to 200. More typically n is from 2 to 200. In other embodiments, however, n is an integer of from 2 to 50, or an integer of from 3 to 50. n may for instance be from 2 to 20, or from 2 to 10.

Typically, where the droplet encapsulate comprises a plurality of the aqueous droplets, part of the outer layer of a first of said aqueous droplets contacts part of the outer layer of a second of said aqueous droplets, thereby forming a bilayer of the non-polymeric amphipathic molecules at an interface between said first and second droplets.

Thus, more generally, the droplet encapsulate of the invention typically comprises a bilayer of said non-polymeric amphipathic molecules, which bilayer is formed at an interface between the aqueous droplet and the peripheral layer or between the aqueous droplet and a second aqueous droplet.

The bilayer at the interface between said first and second droplets may further comprise one or more membrane proteins. Encapsulated droplets can exchange chemical species with each other through membrane proteins incorporated in the bilayer between the droplets. Suitable membrane proteins include, but are not limited to, pumps, channels and/or pores, for instance an αHL pore.

Usually, at least one of said first and second droplets is situated at the edge of the drop, wherein part of the outer layer of the aqueous droplet contacts the peripheral layer, thereby forming a bilayer of said non-polymeric amphipathic molecules at an interface between the aqueous droplet and the peripheral layer.

The bilayer at the interface between said aqueous droplet and the peripheral layer may further comprise one or more membrane proteins. The membrane protein may be of any type, including for instance a pump, channel and/or pore, for example an αHL pore. Encapsulated droplets can exchange material between the droplet and an external solution via such proteins. Also, as explained above, encapsulated droplets within the multisome can also exchange material between each other, via membrane proteins in the bilayers between droplets. Thus, droplet encapsulates having a chain or network of droplets are capable of trafficking materials such as chemical compounds through the chain or network, from droplet to droplet, as well as to and from the external environment. Complex transport systems can be built up in this way and an example of such a system is shown schematically in FIG. 1A.

The first and second droplets in the above-defined droplet encapsulate which comprises a plurality of droplets may both be situated at the edge of the drop, wherein part of the outer layer of the first aqueous droplet contacts the peripheral layer, thereby forming a first bilayer of said non-polymeric amphipathic molecules at an interface between the first aqueous droplet and the peripheral layer, and part of the outer layer of the second aqueous droplet contacts the peripheral layer, thereby forming a second bilayer of said non-polymeric amphipathic molecules at an interface between the second aqueous droplet and the peripheral layer. Such an embodiment is illustrated schematically in FIG. 1B and a photograph of such an embodiment is shown in FIG. 1D. The first or second bilayer may further comprise a membrane protein, or both the first and second bilayers may comprise a membrane protein. Any suitable membrane protein or proteins may be employed. The membrane protein or proteins may for instance be selected from pumps, channels and/or pores, and may for example be an α-hemolysin (αHL) pore. Further possible membrane proteins include, but are not limited to, a receptor, a transporter or a protein which effects cell recognition or a cell-to-cell interaction. Thus, through membrane proteins, both the first and second droplets may be capable of electrical communication or exchange of materials with the external environment, as well as between each other.

As mentioned above, the droplet encapsulate of the invention preferably comprises a bilayer of said non-polymeric amphipathic molecules.

Accordingly, in a preferred embodiment, the droplet encapsulate of the invention as defined herein comprises an aqueous droplet, or a plurality of aqueous droplets, within the peripheral layer, wherein the or each aqueous droplet comprises: (a) an aqueous medium and (b) an outer layer of non-polymeric amphipathic molecules around the surface of the aqueous medium, and the droplet encapsulate further comprises a bilayer of said non-polymeric amphipathic molecules, wherein (i) a said aqueous droplet is situated at the edge of the drop, wherein part of the outer layer of the aqueous droplet contacts said peripheral layer, thereby forming a bilayer of said non-polymeric amphipathic molecules at an interface between the aqueous droplet and the peripheral layer; or (ii) part of the outer layer of a first of said aqueous droplets contacts part of the outer layer of a second of said aqueous droplets, thereby forming a bilayer of the non-polymeric amphipathic molecules at an interface between said first and second droplets.

In one embodiment of the droplet encapsulate of the invention, n is equal to or greater than 3, and part of the outer layer of a first of said aqueous droplets contacts part of the outer layer of a second of said aqueous droplets, thereby forming a bilayer of the non-polymeric amphipathic molecules at an interface between said first and second droplets, and wherein part of the outer layer of the second droplet contacts part of the outer layer of a third of said aqueous droplets, thereby forming a bilayer of the non-polymeric amphipathic molecules at an interface between said second and third droplets.

The bilayer at the interface between the first and second droplets may further comprise a membrane protein.

The bilayer at the interface between the second and third droplets may further comprise a membrane protein.

In one embodiment, the bilayer at the interface between the first and second droplets further comprises a membrane protein, and the bilayer at the interface between the second and third droplets further comprises a membrane protein. The three droplets then form a chain of droplets in communication with each other.

Typically, at least one of said first, second and third droplets is also situated at the edge of the drop, wherein part of the outer layer of the at least one aqueous droplet contacts the peripheral layer, thereby forming a bilayer of said non-polymeric amphipathic molecules at an interface between said aqueous droplet and the peripheral layer.

The bilayer at the interface between the aqueous droplet and the peripheral layer may further comprise a membrane protein, such as a pump, channel or pore. The droplets may then be in communication with the external environment also.

Typically, all three of said first, second and third droplets are situated at the edge of the drop, wherein a part of the outer layer of each of said first, second and third aqueous droplets contacts the peripheral layer, thereby forming bilayers of said non-polymeric amphipathic molecules at interfaces between said first, second and third aqueous droplets and the peripheral layer. A photograph of an example of such an embodiment is shown in FIG. 1E.

At least one of the bilayers of non-polymeric amphipathic molecules at the interfaces between said first, second and third aqueous droplets and the peripheral layer may further comprise a membrane protein. Any suitable membrane protein or proteins may be employed. The membrane protein or proteins may for instance be selected from pumps, channels and/or pores, and may for example be an αHL pore. Further possible membrane proteins include, but are not limited to, receptors, transporters or proteins which effect cell recognition or a cell-to-cell interaction.

The droplet encapsulates of the invention may include chains or networks of the aqueous droplets within the hydrophobic drop. The aqueous droplets in a chain or network are separated from each other by bilayers of non-polymeric amphipathic molecules, typically lipid bilayers, optionally allowing communication within the chain or network through protein pores, when protein pores are present in the bilayers. If a "chain" of droplets is regarded as a "one-dimensional" structure, wherein each droplet contacts a maximum of two other droplets to form a line of droplets, then a network can be regarded as a two- or three-dimensional structure in which at least one droplet is in contact with more than two other droplets. Usually, in a network, more than one droplet in the network is in contact with more than two other droplets. In some networks, each and every droplet in the network is in contact with more than two other droplets. The network can for instance be a "two-dimensional" monolayer of droplets or a "three-dimensional" mass of droplets. Bilayers may also be present at the surfaces of the aqueous droplets that contact the peripheral layer of the hydrophobic drop, enabling the chain or network to communicate with the bulk solution via membrane proteins where present. Thus, multisomes can be prepared that are capable of sensing their environment, processing the information, and then contingently delivering materials to, or receiving materials from, the environment. The sensing and delivery capabilities are demonstrated in the present Examples.

Accordingly, in one embodiment, the droplet encapsulate of the invention may comprise a plurality of said aqueous droplets within the peripheral layer, wherein said plurality of aqueous droplets comprises more than two aqueous droplets which are in contact with one another in a chain or network, wherein a part of the outer layer of each droplet in the chain or network contacts a part of the outer layer of another droplet in the chain or network, thereby forming bilayers of the non-polymeric amphipathic molecules at interfaces between the droplets in the chain or network.

In some embodiments, each of said bilayers at the interfaces between the droplets in the chain or network further comprises a membrane protein. The membrane protein or proteins may be selected from pumps, channels and pores, for instance αHL. In principle, however, any membrane protein may be used. As explained above, further possible membrane proteins include, but are not limited to, a receptor, a transporter or a protein which effects cell recognition or a cell-to-cell interaction.

The number of aqueous droplets in said chain or network may be denoted m, wherein m is an integer equal to or greater than 3. In some embodiments m is equal to or greater than 4. The integer m may for instance be at least 5, or at least 6. In some embodiments, m is equal to or greater than 6.

The integer m can in principle be very high, for instance in the order of millions. As explained above, the aqueous droplets may be very small and all of the aqueous droplets may be present in the same network. Accordingly, the integer m may as high as several million. Such large networks of droplets are useful for preparing prototissue. Thus, in some embodiments, m is an integer of up to about 10,000,000, or for instance up to about 5,000,000.

In other embodiments, m may be as high as 400 or 500. Thus, in one embodiment, m is an integer of up to 500, or for instance up to 400. For instance, m may be an integer of from 3 to 500, or an integer of from 3 to 400. In other embodiments, m may be an integer of from 4 to 500, or an integer of from 4 to 400. Thus, for instance, m may be an integer of from 6 to 500, or an integer of from 10 to 400. More typically m is from 3 to 300, or an integer of from 3 to 200. Thus, m may be from 5 to 200. In some embodiments, n may be an integer of from 3 to 50, or an integer of from 4 to 50. n may for instance be from 3 to 20, or from 3 to 10. In some embodiments, m is from 4 to 10.

Typically, at least one of the aqueous droplets in the chain or network is situated at the edge of the drop, wherein part of the outer layer of the aqueous droplet situated at the edge of the drop contacts the peripheral layer, thereby forming a bilayer of said non-polymeric amphipathic molecules at an interface between said aqueous droplet and the peripheral layer. This bilayer may further comprise one or more membrane proteins, to allow for communication between the chain or network of droplets and the external environment. The membrane protein or proteins may be any suitable membrane protein, for instance a pump, channel or pore. The membrane protein may for instance be αHL. The bilayer may contain multiple copies of the same membrane protein, or two or more different classes of membrane proteins. Where more than one class is present, the bilayer may contain multiple copies of each different class. The bilayer may for example comprise different kinds of ion channel membrane proteins, for instance at least one sodium channel protein and at least one potassium channel protein.

Further possible membrane proteins include, but are not limited to, receptors, transporters or proteins which effect cell recognition or a cell-to-cell interaction.

Typically, at least one of the aqueous droplets in the chain or network is not in contact with the peripheral layer. Thus, at least one of the aqueous droplets in the chain or network may be in the middle of the chain or network, and may therefore be held in a position which is away from the edge of the multisome. In some embodiments, at least two of the aqueous droplets in the chain or network are not in contact with the peripheral layer. An embodiment in which two of the aqueous droplets in the chain or network are not in contact with the peripheral layer is illustrated schematically in FIG. 1A, in which the two aqueous droplets that act as processing modules are present in the middle of the network, away from the peripheral layer.

In one embodiment of the droplet encapsulate of the invention which comprises a said chain or network, a first aqueous droplet, at one end of the chain or network, is situated at the edge of the drop, wherein part of the outer layer of said first aqueous droplet contacts a first part of the peripheral layer, thereby forming a bilayer of said non-polymeric amphipathic molecules at an interface between said first aqueous droplet and said first part of the peripheral layer; and a second aqueous droplet, at another end of the chain or network, is also situated at the edge of the drop (typically at the opposite end of the drop), wherein part of the outer layer of said second aqueous droplet contacts a second part of the peripheral layer, thereby forming a bilayer of said non-polymeric amphipathic molecules at an interface between said second aqueous droplet and said second part of the peripheral layer; and the chain or network further comprises at least one other aqueous droplet, situated between the first and second aqueous droplets. This at least one other aqueous droplet is not usually in contact with the peripheral layer.

Usually, in this embodiment, the chain or network further comprises at least two other aqueous droplets, situated between said first and second aqueous droplets. Typically said at least two other aqueous droplets are not in contact with the peripheral layer.

Figure 1E:
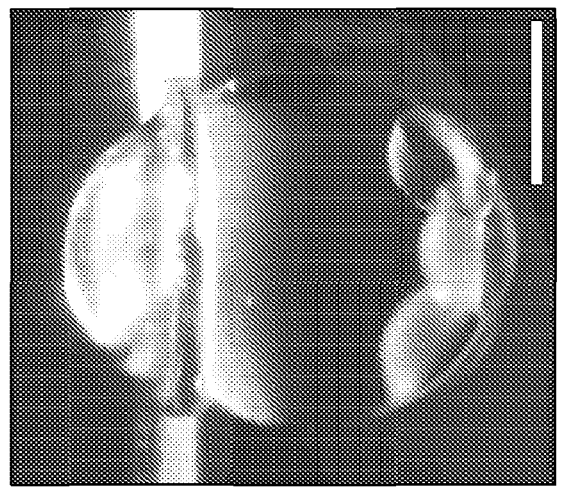
Figure 1D:
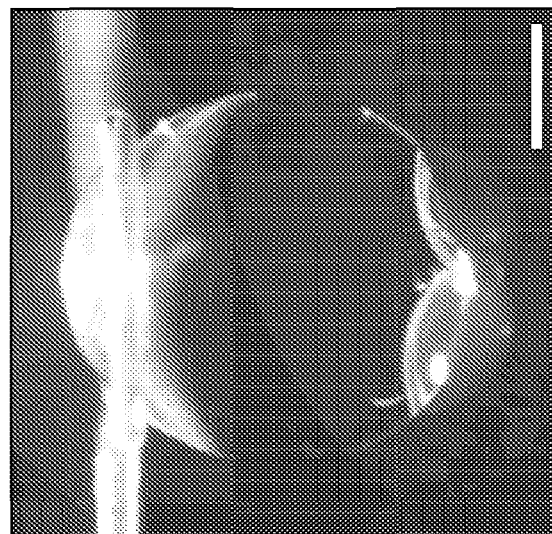
Figure 1C:
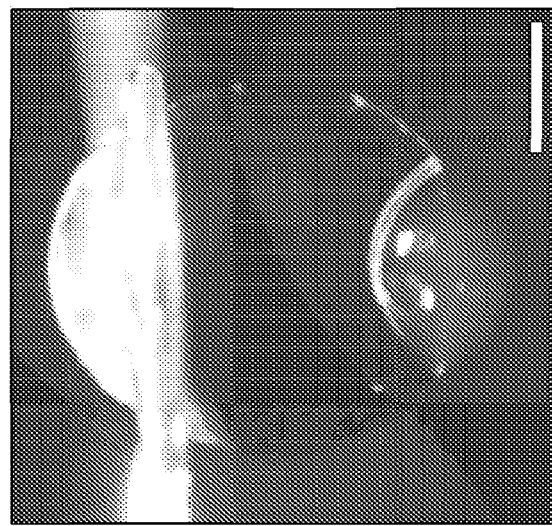

Such an embodiment is illustrated schematically in FIG. 1A. In the embodiment of FIG. 1A, two first aqueous droplets, situated at one end, act as a sensing modules, and two second aqueous droplets, situated at another end of the network, act as a delivery modules, and two further aqueous droplets, which act as processing modules, are situated between the first (sensing) and second (delivery) droplets.

Typically, the bilayer at the interface between the first aqueous droplet and the first part of the peripheral layer further comprises a membrane protein, such as a pump, channel or pore (as described hereinbefore). The chain or network of droplets in the multisome will then be able to communicate with the external environment via the first aqueous droplet and said membrane protein. Said first droplet in the network may for instance act as a sensor module, capable of sensing the presence of a particular chemical in the external environment, for instance, or capable of sensing light. Thus, the first droplet may in some embodiments comprise a sensor molecule. The sensor molecule can be present in the aqueous medium of the droplet or in the bilayer. The sensor molecule may be a molecule which is sensitive to the presence of a particular chemical (for instance a target analyte), or it may be a light-sensitive molecule.

Usually, the bilayer at the interface between the second aqueous droplet and the second part of the peripheral layer further comprises a membrane protein. The chain or network of droplets in the multisome will then also be able to communicate with the external environment via the second aqueous droplet and said membrane protein. Said second droplet in the network may for instance act as a delivery module, capable of delivering a particular chemical to the external environment. Such delivery may for instance be contingent on the first droplet sensing the presence or absence of a chemical or, for instance, the presence or absence of light.

The aqueous droplets in the droplet encapsulates of the invention may therefore be used as sensor modules and accordingly, in one embodiment, the aqueous droplet, or at least one of the aqueous droplets in the droplet encapsulates of the invention as defined herein may further comprise a sensor molecule. The sensor molecule can be present in the aqueous medium of the droplet or in a bilayer formed at an interface between the aqueous droplet and the peripheral layer or between the aqueous droplet and a further aqueous droplet. Any suitable sensor molecule may be employed. The sensor molecule may for instance be a molecule which is sensitive to the presence of a particular chemical, for instance a target analyte, or for instance a light-sensitive molecule. An example of a suitable light-sensitive sensor molecule is bacteriorhodopsin. Bacteriorhodopsin is a membrane protein that captures light energy and uses it to move protons across the membrane. Other suitable examples of sensor molecules include gated ion channels and receptor proteins.

The aqueous droplet, or at least one of the aqueous droplets in the droplet encapsulate of the invention may further comprise a molecule for delivery. Delivery of the molecule from the droplet encapsulate to the external environment may for instance be contingent on activation of a sensor molecule in the or in another droplet in the encapsulate.

The hydrophobic medium in the droplet encapsulates of the invention may be selected from a wide range of materials. The hydrophobic medium may comprise a single hydrophobic compound. Alternatively, it may comprise a mixture of two or more different hydrophobic compounds. The medium is hydrophobic so that the aqueous droplet or droplets in the multisome remain encapsulated in droplet form, rather than mixing with the hydrophobic medium, but otherwise the hydrophobic medium can be freely chosen. The hydrophobic medium can be selected to affect the buoyancy of the aqueous droplet or droplets in the multisome and the speed of formation of the outer layer of non-polymeric amphipathic molecules around the aqueous droplet or droplets when preparing the multisome.

The hydrophobic medium in the droplet encapsulates of the invention is typically an oil. The oil may be a single, pure, compound, or the oil may comprise a mixture of two or more compounds. Any type of oil is suitable, as long as its interfacial tension with the hydrophilic media of the aqueous droplets and the external bulk phase is high enough to prevent the spontaneous disintegration of the oil and aqueous droplets, and as long as it does not destabilize the formed bilayers.

The oil may for instance comprise silicone oil (for instance poly phenyl methyl siloxane). The oil may consist of a single silicone oil, for instance poly phenyl methyl siloxane. Alternatively, the oil may comprise a mixture of two or more different silicone oils.

Additionally or alternatively, the oil may comprise a hydrocarbon. When the oil comprises a hydrocarbon it may comprise a single hydrocarbon compound, or a mixture of two or more hydrocarbons.

In some embodiments, the oil is a mixture comprising: (a) one or more hydrocarbons, and (b) one or more silicone oils.

When the oil comprises a hydrocarbon, the hydrocarbon may be branched or unbranched, for example a hydrocarbon having from 5 to 30 carbon atoms, or from 5 to 20 carbon atoms (although hydrocarbons of lower molecular weight would require control of evaporation). Preferably, the hydrocarbon is a liquid at the operating temperature of the droplet encapsulate of the invention. Suitable examples include alkanes or alkenes, such as hexadecane, decane, pentane or squalene. Usually, the oil comprises a hydrocarbon.

Typically the hydrocarbon is an unsubstituted $C_{10}$-$C_{20}$ alkane, for instance hexadecane. Although it was found that the low density of pure hexadecane made the assembly of multisomes by the method described in the present Examples difficult, hexadecane and shorter alkanes should nonetheless be suitable for other multisomes for which buoyancy effects are less important and whose monolayers may form more quickly, including for instance "miniaturised" multisomes that are smaller than those prepared in the present Examples.

In some embodiments the hydrocarbon is a longer-chain hydrocarbon, such as unsubstituted $C_{17}$-$C_{20}$ alkane.

Other types of oil are possible. For example the oil may be a fluorocarbon. This might be useful for the study of some systems, for example to minimise loss of a particular membrane protein or analyte from the droplet or to control gas content such as oxygen. Because fluorocarbons can be both hydrophobic and lipophobic, an oil phase that comprises fluorocarbons can usefully prevent the adhesion of multisomes to surfaces.

In another embodiment, the hydrocarbon is a bromo-substituted $C_{10}$-$C_{30}$ alkane, or for instance a bromo-substituted $C_{10}$-$C_{20}$ alkane, e.g. bromododecane. Although bromododecane was found to require long incubation times for monolayer formation, this oil should be more suitable for other multisomes whose monolayers may incubate more quickly, for instance "miniaturised" multisomes, which are smaller than those prepared in the present Examples.

Typically, the oil comprises silicone oil or a hydrocarbon. Any suitable silicone oil may be employed.

Silicone oil is advantageous on account of its density being close to that of water, which ensures that the droplet encapsulates are approximately neutrally buoyant in water. The silicone oil may for instance be poly phenyl methyl siloxane, which has a density of about 1 g·cm$^{-3}$.

The hydrocarbon typically has from 5 to 20 carbon atoms (a $C_5$-$C_{20}$ hydrocarbon), more typically from 10 to 20 carbon atoms (a $C_{10}$-$C_{20}$ hydrocarbon). Typically, it is an alkane or an alkene. Thus, the hydrocarbon may be a $C_5$-$C_{20}$ alkane, or a $C_{10}$-$C_{20}$ alkane. In another embodiment, the hydrocarbon may be a $C_5$-$C_{20}$ alkene, or a $C_{10}$-$C_{20}$ alkene. The hydrocarbon is typically unsubstituted. In a preferred embodiment, the hydrocarbon is an unsubstituted $C_5$-$C_{20}$ alkane, preferably an unsubstituted $C_{10}$-$C_{20}$ alkane. The hydrocarbon may for instance be squalene, hexadecane or decane. In one embodiment it is squalene. However, in some embodiments the hydrocarbon may be substituted with a halogen atom, for instance bromine.

In some embodiments, the hydrophobic medium comprises a mixture of silicone oil and a hydrocarbon. Such mixtures have been found to provide advantageously low incubation times for stable multisomes to be formed. The silicone oil and hydrocarbon in the mixture may be as further defined above. Typically, the hydrocarbon is an unsubstituted $C_{10}$-$C_{20}$ alkane, preferably hexadecane. The silicone oil typically has a density close to that of water, to ensure the multisome has approximately neutral buoyancy in aqueous media; it may for instance be poly phenyl methyl siloxane. Usually, the volume ratio of the silicone oil to the hydrocarbon is equal or greater than 5:1. The volume ratio of the silicone oil to the hydrocarbon may for instance be from 5:1 to 15:1, for instance about 9:1 or about 10:1.

Typically, the hydrophobic medium employed in the droplet encapsulates of the invention has a density close to that of water, for instance a density of about 1 g·cm$^{-3}$, such that the droplet encapsulates of the invention are approximately neutrally buoyant in water.

In one embodiment, the hydrophobic medium comprises both silicone oil and hexadecane. Typically the silicone oil is poly phenyl methyl siloxane. The volume ratio of the silicone oil to the hexadecane is typically equal or greater than 5:1, for instance from 5:1 to 15:1. It may for instance be about 9:1, or about 10:1.

The aqueous medium within the aqueous droplet or droplets in the droplet encapsulates of the invention may be pure water. Alternatively, the aqueous medium may be an aqueous solution, for instance an aqueous buffer solution. The aqueous solution may be freely chosen for the purpose or use of the multisome, or for the experiment to be performed using the multisome. The aqueous solution of each droplet in the droplet encapsulates may be the same or different. One important property is pH and this can be varied over a wide range. In some embodiments, for instance, the pH of the aqueous medium within the aqueous droplet or droplets may be in the range of from 5 to 9 (or for instance in the range of from 6 to 8) although higher and lower pHs are also possible. The aqueous medium may therefore be an aqueous buffer solution. Any suitable buffer can be employed, depending on the desired pH. The buffer solution may for instance comprise Tris HCl, with KCl, and EDTA. In some embodiments the pH of the aqueous buffer solution is from 5 to 9, or for instance from 6 to 8. The nature and concentration of the solutes can be varied to vary the properties of the solution.

The droplet encapsulate of the invention comprises amphipathic molecules which are not polymers and which do not comprise polymers. Such amphipathic molecules, which are present in both the peripheral layer of the droplet encapsulate, and in the outer layer of the or each aqueous droplet, are referred to herein as "non-polymeric amphipathic molecules".

In general, the non-polymeric amphipathic molecules can be of any type which is capable of forming a bilayer within the hydrophobic medium in the multisome. This is dependent on the nature of the hydrophobic medium and the aqueous medium of the droplets, but a wide range of non-polymeric amphipathic molecules are possible. Amphipathic molecules are molecules which have both hydrophobic and hydrophilic groups. As mentioned above, the outer layer formed around the aqueous droplet usually comprises a monolayer of non-polymeric amphipathic molecules which is formed and maintained naturally by the interaction of the hydrophobic and hydrophilic groups with the aqueous medium so that the molecules align on the surface of the droplet with the hydrophilic groups facing inwards towards the aqueous medium and the hydrophobic groups facing outwards towards the hydrophobic medium. Likewise, the peripheral layer formed around the hydrophobic drop usually comprises a monolayer of non-polymeric amphipathic molecules which is formed and maintained naturally by the interaction of the hydrophobic and hydrophilic groups with: (a) the hydrophobic medium of the drop and, when the droplet encapsulate is suspended within a hydrophilic carrier such as an aqueous medium or an ionic liquid, (b) the hydrophilic carrier.

An important class of non-polymeric amphipathic molecules which can be used in the droplet encapsulates of the invention is lipid molecules. The lipid molecules may be any of the major classes of lipid, including phospholipids, fatty acids, fatty acyls, glycerolipids, glycerophospholipids, sphingolipids, sterol lipids, prenol lipids, saccharolipids and polyketides. Some important examples include phospholipids and fatty acids. The lipid molecules may be naturally occurring or synthetic. Whilst the formation of a bilayer from lipid molecules has been demonstrated the method is expected to be appropriate for any non-polymeric amphipathic molecules capable of forming a bilayer.

A common class of hydrophobic group that may be present in a non-polymeric amphipathic molecule is a hydrocarbon group, as for instance in most lipids. However, another suitable kind of hydrophobic group that may be employed is a fluorocarbon group. Thus, a further important class of non-polymeric amphipathic molecule is a non-polymeric amphipathic molecule that comprises at least one fluorocarbon group. An example of such a molecule would be a lipid-like molecule which comprises a hydrophobic fluorocarbon tail and a hydrophilic head group. Fluoroamphiphiles can be used to prevent the insertion of membrane proteins into lipid bilayers, possibly by sequestering the proteins in aggregates of the fluoroamphiphile (Raychaudhuri et al. Biochemistry 50, 1599-1606 (2011)).

The non-polymeric amphipathic molecules in the droplet encapsulate need not be all of the same type. Rather, the non-polymeric amphipathic molecules may in some embodiments be a mixture of two or more different kinds of non-polymeric amphipathic molecule. Another important example is that the non-polymeric amphipathic molecules in the respective outer layers of different aqueous droplets in the multisome may be of different types so that the bilayer(s) formed between the different aqueous droplets may be asymmetric.

Typically, therefore, the non-polymeric amphipathic molecules in the droplet encapsulate of the invention comprise lipid molecules. The lipid molecules need not be all of the same type. Thus, the non-polymeric amphipathic molecules in the droplet encapsulate of the invention may comprise a single type of lipid or a mixture of two or more different lipid molecules. Also, the lipid composition of the peripheral layer of the droplet encapsulate may be the same as or different from that of the outer layer of the aqueous droplet. When more than one aqueous droplet is present in the encapsulate, the lipid compositions of the outer layers of the aqueous droplets may be the same as or different from one another, and the same as or different from the lipid composition of the peripheral layer. Lipid molecules are particularly advantageous because lipid bilayers, or more generally bilayers of non-polymeric amphipathic molecules, are models of cell membranes and the droplet encapsulates of the invention therefore serve as excellent platforms for a range of experimental studies, including for instance as novel platforms for the fundamental study of membrane proteins, or as multi-compartment protocellular chassis for "bottom-up" synthetic biology.

Phospholipids are particularly preferred for reasons outlined above and also because they are a major component of all cell membranes, making droplet encapsulates comprising phospholipids particularly suitable for synthetic biology applications, as well as for drug delivery.

Accordingly, the non-polymeric amphipathic molecules in the droplet encapsulates of the invention typically comprise phospholipid molecules. The phospholipid molecules may be the same or different, i.e. the non-polymeric amphipathic molecules in the droplet encapsulate may comprise a single kind of phospholipid, or a mixture of two or more different phospholipids. Phospholipids are well known to the skilled person and many are commercially available, from suppliers such as Avanti Polar Lipids. The phospholipid molecules may be glycerophospholipids or phosphosphingolipids or a mixture of the two. The phospholipid molecules may comprise anionic phospholipids, phospholipids comprising primary amines, choline-containing phospholipids and/or glycosphingolipids. Usually, the non-polymeric amphipathic molecules comprise one or more glycerophospholipids. As the skilled person will appreciate, glycerophospholipids include, but are not limited to glycerophospholipids having a structure as defined in the following formula (I):

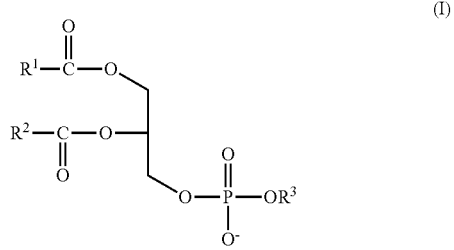

wherein:
R$^1$ and R$^2$, which are the same or different, are selected from C$_{10}$-C$_{25}$ alkyl groups and C$_{10}$-C$_{25}$ alkylene groups;
either R$^3$ is absent such that OR$^3$ is O$^-$, or R$^3$ is present and is H, CH$_2$CH$_2$N(R$^4$)$_3$$^+$, a sugar group, or an amino acid group; and
each R$^4$, which is the same or different, is independently selected from H and unsubstituted C$_1$-C$_4$ alkyl.

Typically, when R$^3$ is CH$_2$CH$_2$N(R$^4$)$_3$+, each R$^4$, which is the same or different, is selected from H and methyl. As the skilled person will appreciate, when each and every R$^4$ is methyl, the R$^3$ group is a choline group, and when each and every R$^4$ is H, the R$^3$ group is an ethanolamine group.

When R$^3$ is an amino acid group it may for instance be a serine group, i.e. —CH$_2$CH(NH$_2$)(COOH). When R$^3$ is a sugar group, it may for instance be glycerol, i.e. —CH$_2$CHOHCH$_2$OH, or for instance inositol, i.e. —CH(CHOH)$_5$.

Typical examples of R$^1$ and R$^2$ groups are C$_{10}$-C$_{25}$ alkyl groups, including, but not limited to linear C$_{10}$-C$_{25}$ alkyl groups such as, for instance, CH$_3$(CH$_2$)$_{10}$—, CH$_3$(CH$_2$)$_{12}$—, CH$_3$(CH$_2$)$_{14}$—, CH$_3$(CH$_2$)$_{16}$—, CH$_3$(CH$_2$)$_{18}$—, CH$_3$(CH$_2$)$_{22}$— and branched C$_{10}$-C$_{25}$ alkyl groups such as for instance —CH$_2$—CH(CH$_3$)—(CH$_2$)$_3$—CH(CH$_3$)—(CH$_2$)$_3$—CH(CH$_3$)—(CH$_2$)$_3$—CH(CH$_3$)$_2$.

Further typical examples of R$^1$ and R$^2$ groups are unsubstituted C$_{10}$-C$_{25}$ alkylene groups, including, but not limited to, CH$_3$(CH$_2$)$_5$CH=CH(CH$_2$)$_7$—, CH$_3$(CH$_2$)$_7$CH=CH(CH$_2$)$_7$—, CH$_3$(CH$_2$)$_4$CH=CHCH$_2$CH=CH(CH$_2$)$_7$—, CH$_3$(CH$_2$)$_4$(CH=CHCH$_2$)$_3$CH=CH(CH$_2$)$_3$—, and CH$_3$CH$_2$CH=CHCH$_2$CH=CHCH$_2$CH=CH(CH$_2$)$_7$—.

As the skilled person will appreciate, the O⁻ group in the phosphate group adjacent the OR³ group may in some embodiments be protonated, or associated with a suitable cation, for instance a metal cation such as Na⁺.

Thus, the non-polymeric amphipathic molecules may comprise one or more glycerophospholipids having the structure of formula (I) as defined above.

For instance, the non-polymeric amphipathic molecules may comprise any one or more of the following glycerophospholipids: 1,2-diphytanoyl-sn-glycero-3-phosphocholine (DPhPC), 1,2-distearoyl-sn-glycero-3-phosphocholine (DSPC) 1,2-dipalmitoyl-sn-glycero-3-phosphocholine (DPPC), or 1,2-dipalmitoyl-sn-glycero-3-[phospho-rac-(1-glycerol)] (DPPG) can be employed as the amphiphilic molecules in the droplet encapsulates of the invention, or a mixture of one or more thereof. The glycerophospholipid 1,2-dioleoyl-sn-glycero-3-phosphoethanolamine (DOPE) may also be used, and is typically used in combination with a pH-sensitive lipid, for instance a fatty acid (see further below).

The non-polymeric amphipathic molecules in the droplet encapsulates of the invention may comprise one or more fatty acids, e.g. oleic acid. Fatty acids are of course well known to the skilled person and a wide range of these are commercially available.

The non-polymeric amphipathic molecules may for instance comprise a mixture comprising: (a) one or more phospholipids, and (b) one or more fatty acids.

In addition to the non-polymeric amphipathic molecules, the peripheral layer of the droplet encapsulate of the invention may further comprise a PEGylated lipid. The term "PEGylated lipid", as used herein, refers to a lipid which has been derivatised with poly(ethylene glycol).

The inclusion of one or more PEGylated lipids in the peripheral layer of the multisome has the useful effect of stabilising the multisome in vivo, and in particular prolongs the plasma half-life of the multisome. This means that, when the multisome contains one or more therapeutic or diagnostic agents, the inclusion of one or more PEGylated lipids in the peripheral layer also has the useful effect of prolonging the plasma half-life of the agent within the multisome. Such effects have been observed previously when PEGylated lipids are used in liposomal drug formulations. PEGylated lipids are known in the art and are commercially available from suppliers such as NOF Corporation, Japan (see http://www.phospholipid.jp/phospholipid_2-3.html). Any suitable PEGylated lipid may be employed in the present invention, including, but not limited to, PEG-phospholipids, diacylglycerol-PEG, cholesterol-PEG derivatives, and mixtures thereof.

Thus, in one embodiment, the peripheral layer of the droplet encapsulate of the invention further comprises a PEGylated lipid. The peripheral layer may include one or more PEGylated lipids in addition to the non-polymeric amphipathic molecules, for instance multiple copies of the same PEGylated lipid, or a mixture of two or more different classes of PEGylated lipids. Suitable PEGylated lipids include, but are not limited to PEG-phospholipids, diacylglycerol-PEG, cholesterol-PEG derivatives and mixtures thereof. The poly(ethylene glycol) (PEG) component of the PEGylated lipid may have any one of several different geometries. Thus, it could be substantially linear PEG or branched PEG. The branched PEG may for instance have from three to ten PEG chains emanating from a central core group. Alternatively, the branched PEG could be a star PEG, having from 10 to 100 PEG chains emanating from a central core group. Alternatively, the PEG may be a comb PEG, having multiple PEG chains grafted to a polymer backbone.

The one or more PEGylated lipids employed in the peripheral layer may for instance comprise a PEG-phospholipid of the following formula (II)

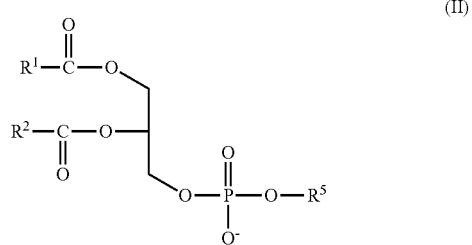

(II)

wherein R¹ and R² are as defined above for the glycerophospholipids of formula (I), and R⁵ is a group which comprises poly(ethylene glycol).

The group which comprises poly(ethylene glycol) may for instance have the formula —CH₂CH₂NHC(O)—X, or for instance —CH₂CH₂NHC(O)(CH₂)₃C(O)—X wherein X comprises said poly(ethylene glycol). The group X may for instance comprise substantially linear PEG, or for instance a branched PEG, having, for instance, from three to ten PEG chains emanating from a central core group. Alternatively, it can be a star PEG, having, for instance, from 10 to 100 PEG chains emanating from a central core group. Or for instance it may be a comb PEG, having multiple PEG chains grafted to a polymer backbone.

Thus, R⁵ may for instance be —CH₂CH₂NHC(O)—(OCH₂CH₂)$_q$OCH₃, —CH₂CH₂NHC(O)(CH₂)₃C(O)—(OCH₂CH₂)$_q$OCH₃, —CH₂CH₂NHC(O)—(OCH₂CH₂)$_q$OH, or —CH₂CH₂NHC(O)(CH₂)₃C(O)—(OCH₂CH₂)$_q$OH, wherein q is a positive integer. The integer q may for instance be from 5 to 10,000, or for instance from 10 to 1,000.

Alternatively, R⁵ may be —(CH₂CH₂O)$_q$CH₃ or —(CH₂CH₂O)$_q$H, wherein q is a positive integer. The integer q may for instance be from 5 to 10,000, or for instance from 10 to 1,000.

Additionally or alternatively, the one or more PEGylated lipids may comprise a diacylglycerol-PEG of formula (III)

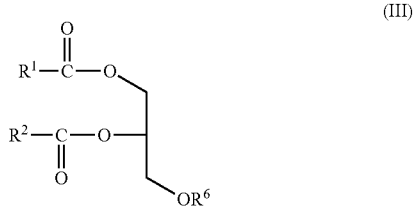

(III)

wherein R¹ and R² are as defined above for the glycerophospholipids of formula (I), and R⁶ is a group which comprises poly(ethylene glycol).

The poly(ethylene glycol) may for instance comprise substantially linear PEG, or for instance a branched PEG, having, for instance, from three to ten PEG chains emanating from a central core group. Alternatively, it can be a star PEG, having, for instance, from 10 to 100 PEG chains emanating from a central core group. Or for instance it may be a comb PEG, having multiple PEG chains grafted to a polymer backbone.

R⁶ may for instance be —(CH₂CH₂O)$_q$CH₃, —(CH₂CH₂O)$_q$H, —CH₂CH₂NHC(O)—(OCH₂CH₂)$_q$OCH₃, —CH₂CH₂NHC(O)—(OCH₂CH₂)$_q$OH, —CH₂CH₂NHC(O)(CH₂)₃C(O)—(OCH₂CH₂)$_q$OCH₃ or —CH₂CH₂NHC(O)(CH₂)₃C(O)—(OCH₂CH₂)$_q$OH wherein q is a positive integer. The integer q may for instance be from 5 to 10,000, or for instance from 10 to 1,000.

Additionally or alternatively, the one or more PEGylated lipids may comprise a cholesterol-PEG derivative of formula (IV)

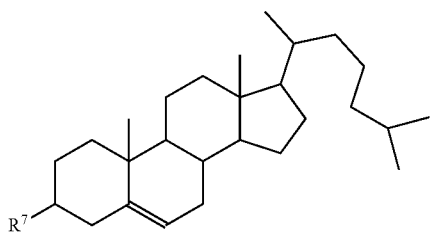

(IV)

wherein R⁷ is a group which comprises poly(ethylene glycol).

Again, the poly(ethylene glycol) may comprise substantially linear PEG, or for instance a branched PEG, having, for instance, from three to ten PEG chains emanating from a central core group. Alternatively, it can be a star PEG, having, for instance, from 10 to 100 PEG chains emanating from a central core group. Or for instance it may be a comb PEG, having multiple PEG chains grafted to a polymer backbone.

R⁷ may for instance be —(OCH₂CH₂)$_q$OH or —(OCH₂CH₂)$_q$OCH₃ wherein q is a positive integer. The integer q may for instance be from 5 to 10,000, or for instance from 10 to 1,000.

Polyglycerine may be used instead of poly(ethylene glycol), and so in one embodiment the peripheral layer of the droplet encapsulate of the invention may further comprise a lipid which comprises a polyglycerine moiety.

Droplet encapsulates of the invention having diameters in the range 500 μm to 2000 μm, typically about 800 μm have been produced experimentally. It is however expected that larger droplet encapsulates and droplet encapsulates of smaller diameter could be produced. Accordingly, in one embodiment, the droplet encapsulates of the invention have a diameter which is equal to or less than 2 mm, preferably equal to or less than 1 mm.

The volumes of the droplet encapsulates of the invention which have been produced experimentally typically range from 0.2 μL to 2 μL, but again it is expected that larger droplet encapsulates and droplet encapsulates of smaller volume could be produced. Thus, in one embodiment, the droplet encapsulate of the invention has a volume which is equal to or less than 4 μL, preferably equal to or less than 2 μL. The droplet encapsulate may for instance have a volume in the range of from 0.2 μL to 2 μL.

Typically, the or each aqueous droplet within the droplet encapsulate of the invention has a diameter which is equal to or less than 500 μm, preferably equal to or less than 300 μm.

The volume of the or each aqueous droplet in the droplet encapsulate of the invention is usually equal to or less than 80 nL, for instance equal to or less than 20 nL. In one embodiment, the or each aqueous droplet has a volume of from 0.5 nL to 70 nL.

As mentioned above, it is expected that the droplet encapsulates of smaller volume and diameter could be produced. Smaller droplet encapsulates are particularly desirable for administration in vivo, for instance in drug delivery applications. Indeed, it would be preferable in applications which require multisomes to interact with living cells that the droplet encapsulates were no larger than a few microns, and ideally <200 nm.

Thus, the droplet encapsulate of the invention may in some embodiments have a diameter which is equal to or less than 10 μm, or, for instance, equal to or less than 200 nm.

The droplet encapsulate of the invention may in some embodiments have a volume which is equal to or less than 0.5 picolitres, or for instance equal to or less than 5 attolitres.

The effect of increased curvature on the monolayers and bilayers is likely to be significant in encapsulates of these sizes. It may therefore be preferable to use lipids with high intrinsic curvatures in such droplet encapsulates, in order to tailor the curvature-dependent properties of the monolayers and bilayers, such as phase transitions. Lipids having high intrinsic curvatures are well known to the skilled person. Zimmerberg, J. & Kozlov, M. M. *Nat. Rev. Mol. Cell Bio.* 7, 9-19 (2006) presents several strategies for producing bilayer curvature, and Table 1 in that paper lists some lipids with high intrinsic curvatures, such as DOPE (with negative curvature) and various lysolipids (with positive curvature). Thus, examples of lipids with high intrinsic curvatures include the following lysophospholipids, all of which have positive curvatures: L-lyso phosphatidylcholine (L-lyso PC), O-lyso phosphatidylcholine (O-lyso PC), P-lyso phosphatidylcholine (P-lyso PC), lysophosphatidic acid (LPA), L-lyso phosphatidylethanolamine (L-lyso PE), O-lyso phosphatidylethanolamine (O-lyso PE) and S-lyso phosphatidylethanolamine (S-lyso PE). Dioleoylphosphatidylserine (DOPS) also has positive curvature. Further examples of lipids with high intrinsic curvatures include the following, which have negative curvatures: dioleoylphosphatidylcholine (DOPC), phosphatidic acid (PA), 1,2-dioleoyl-sn-glycero-3-phosphoethanolamine (DOPE), cholesterol, dicaprylglycerol (DCG) and diacylglycerol (DAG) (Zimmerberg, J. & Kozlov, M. M. *Nat. Rev. Mol. Cell Bio.* 7, 9-19 (2006)).

Thus, the non-polymeric amphipathic molecules in the droplet encapsulates of the invention may in some embodiments be selected from L-lyso PC, O-lyso PC, P-lyso PC, LPA, L-lyso PE, O-lyso PE, S-lyso PE, DOPS, DOPC, PA, DOPE, cholesterol, DCG and DAG.

It would be preferable in droplet encapsulates of less than 10 μm in diameter to coat the encapsulated aqueous droplets, and the drop of hydrophobic medium, with lipids of opposite curvature respectively. This might be achieved by incubating the aqueous droplets in oil containing lipids with negative curvature, then transferring the droplets into an oil droplet coated with a monolayer of lipid with positive curvature.

Thus, typically the non-polymeric amphipathic molecules in the peripheral layer comprise lipids having a first curvature and the non-polymeric amphipathic molecules in the outer layer of the or each aqueous droplet comprise lipids having a second curvature, wherein either the first curvature is positive and the second curvature is negative, or the second curvature is positive and the first curvature is negative.

Examples of lipids having negative curvature include DOPC, PA, DOPE, cholesterol, DCG and DAG. Examples of lipids having positive curvature include lysophospholipids (for instance L-lyso PC, O-lyso PC, P-lyso PC, LPA, L-lyso PE, O-lyso PE and S-lyso PE) and DOPS.

As mentioned above, the peripheral layer may further comprise one or more PEGylated lipids (which may be the same or different when more than one is present) in order to increase the lifetime of the multisome in the bloodstream.

Droplet encapsulates of the invention may be used as drug delivery vehicles, for instance as vehicles for delivering therapeutic agents, diagnostic agents, or contrast agents in vivo, or for delivering any other type of compound or composition in vivo as desired.

Accordingly, in one embodiment, the droplet encapsulate of the invention further comprises a therapeutic agent.

The therapeutic agent may be in prodrug form. Thus in one embodiment, the droplet encapsulate of the invention further comprises a prodrug.

The droplet encapsulate of the invention may alternatively comprise a diagnostic agent, or for instance a contrast agent.

The therapeutic agent, prodrug, diagnostic agent, or contrast agent may be present in the hydrophilic medium of an aqueous droplet within the droplet encapsulate of the invention. Alternatively, it may be present in the hydrophobic medium of the drop. Typically, it is present in the hydrophilic medium of the or an aqueous droplet in the encapsulate.

Multiple droplets within the same droplet encapsulate can release their contents into the environment simultaneously or at different times, e.g. upon exposure to an external stimulus such as a change in pH or temperature; this provides a useful method for the combinatorial delivery of drugs. Indeed, delivering multiple pharmacological species to a cell by encapsulation in conventional liposomes requires that these species be encapsulated either together, allowing potentially undesirable reactions between them; or separately, in which case each cell will receive a poorly controlled proportion of each species. By contrast, the delivery of several drugs encapsulated in different compartments of a single multisome (including in the hydrophobic phase) would allow precise control over dosage proportions. This may be beneficial for the delivery of drugs with independent mechanisms of action; their uptake by cells in fixed proportions could be expected to increase their overall efficacy, and decrease the probability of resistance developing to any one of the drugs.

Accordingly, in one embodiment, the droplet encapsulate of the invention further comprises a first agent and a second agent. Typically, these are present in separate parts of the encapsulate. The parts of the encapsulate referred to here include the hydrophobic medium of the drop, and the aqueous medium of any of the aqueous droplets.

Thus, in one embodiment the first agent is within the, or at least one of the, aqueous droplets in the encapsulate, and the second agent is within the hydrophobic medium.

In another embodiment, the droplet encapsulate of the invention is a droplet encapsulate which comprises a plurality of said aqueous droplets, and the first agent and the second agent are within different aqueous droplets of the encapsulate.

Typically, the first and second agents are selected from therapeutic agents, diagnostic agents, drugs for use together in combination therapies, prodrugs and their corresponding activators, drugs and their corresponding deactivator compounds, and contrast agents for monitoring the biodistribution of a drug.

Alternatively, the first and second agents may be reactant compounds for reacting together in a chemical reaction.

Typically, the first and second agents are present in the droplet encapsulate in a predetermined proportion, for instance in a predetermined dosage proportion, or for instance in a stoichiometric proportion suitable for a particular chemical reaction to take place between the agents.

The delivery of multiple drugs with independent mechanisms of action can be more effective than the sum of the effects of each drug separately. A common use of drug combinations is to prevent the emergence of drug resistance in a wide range of diseases. If the various drugs are delivered in solution, the proportion of each drug taken up by a particular cell is poorly controlled. By contrast, encapsulation of these drugs in a single carrier, such as a droplet encapsulate of the invention, enables precise control over dosage proportions. Encapsulating multiple drugs in separate compartments of each multisome prevents any undesirable interactions between the drugs, and allows the conditions in each aqueous compartment to be optimized for the drug in that compartment.

Thus, in one embodiment, the first and second agents referred to above are two different drugs. Typically, the first and second agents are drugs which are suitable for use together in a combination therapy. The drugs may be present in the droplet encapsulate in a predetermined dosage proportion. Many drug combinations which are suitable for use together in a combination therapy, and which are therefore suitable for use together in a droplet encapsulate of the invention, are known in the art.

For instance, the use of combinations of antimalarials that do not share the same resistance mechanism may reduce the chances of drug resistance (White, N. "Antimalarial drug resistance and combination chemotherapy." *Phil. Trans. R. Soc. Lond. B* 354, 739-749 (1999)). Thus, the first and second agents may be two different antimalarial drugs having different drug resistance mechanisms. In particular, the first and second antimalarial drugs may be pyrimethamine in combination with sulphadoxine or sulphalene, which combination is used to treat malaria caused by chloroquine-resistant *P. falciparum*. The two compounds inhibit sequential steps in folate biosynthesis. The same mechanism is employed by the combination of chlorproguanil and dapsone. Other antimalarial drug combinations with different mechanisms of action include: atovaquone and proguanil, artemisin and mefloquine, artemether and lumefantrine, artesunate with atovaquone and proguanil, quinine and tetracycline, and quinine and clindamycin. Thus, the first and second agents may be any of the abovementioned combinations.

A further example is cancer, for which a great number of combination chemotherapy regimens exist (see, for instance, http://www.macmillan.org.uk). Some examples are ABVD (doxorubicin, bleomycin, vinblastine and dacarbazine) for Hodgkin's lymphoma, CHOP (cyclophosphamide, doxorubicin, vincristine and prednisone) for non-Hodgkin's lymphoma, and CMF (cyclophosphamide, methotrexate and 5-fluorouracil) for breast cancer. Thus, the droplet encapsulate of the invention may comprise any of the abovementioned combinations and the different drugs may be contained within the same or different compartments of the encapsulate.

Yet further examples of drugs which can be included within the droplet encapsulate of the invention are drug combinations used to treat viral infection (see Clavel, F. & Hance, A. J. HIV drug resistance. N. Engl. J. Med. 350, 1023-1035 (2004)). Typical combinations include nucleoside reverse-transcriptase inhibitors (which inhibit reverse transcription of the viral genome) and a non-nucleoside reverse-transcriptase inhibitor (which inhibits reverse transcription of the viral genome by a different mechanism) or a protease inhibitor (which inhibits viral particle assembly). Some current recommended regimens are (see http://aidsinfo.nih.gov): emtricitabine, tenofovir and efavirenz; emtricitabine, tenofovir, tazanavir and ritonavir; emtricitabine, tenofovir, darunavir and ritonavir; and emtricitabine, tenofovir, and raltegravir. The droplet encapsulate of the invention may therefore comprise any of the abovementioned combinations and the different drugs may be contained within different compartments of the encapsulate.

The droplet encapsulates of the invention also allow the delivery of compounds that independently have little or no effect, and are only effective in combination with other compounds. These synergistic combinations are used in some treatments for bacterial infection, and in the delivery of prodrugs (inactive precursors of active drugs). In some cases, as in the treatment of bacterial infections discussed below, the various compounds may be encapsulated together, in which case the advantages of multisomes are as discussed above. In other cases, such as the delivery and activation of prodrugs as discussed below, the components react when brought together. Thus, when a multisome is triggered to release its contents, an active species can be created in situ with different properties to its parent compounds. Some examples are as follows:

Bacterial infection [Walsh, C. Molecular mechanisms that confer antibacterial drug resistance. Nature 406, 775-781 (2000)]: Amoxicillin is used in combination with clavulanate, which inactivates an enzyme that in certain strains would otherwise deactivate amoxicillin. The combination of ampicillin and sulbactam employs a similar principle, where sulbactam is the enzyme deactivator. Another synergistic combination is that of quinupristin and dalfopristin.

Accordingly, the first and second drugs in the droplet encapsulate of the invention may for instance be amoxicillin and clavulanate respectively, ampicillin and sulbactam respectively, or quinupristin and dalfopristin respectively.

Another possibility is enzyme-prodrug therapy [Xu, G. & McLeod, H. L. Clin. Cancer Res. 7, 3314-3324 (2001)]: HMR 1826, an inactive derivative of the anti-cancer drug doxorubicin, is converted by human beta-glucuronidase to doxorubicin. In a study that employed this combination, the human beta-glucuronidase gene was first transfected into tumour cells, which then produced the enzyme and secreted it. The prodrug HMR 1826 was added to the extracellular space, where it was converted to the active drug doxorubicin. Whereas HMR 1826 is not permeable to the cell membrane, doxorubicin is able to access the cytosol. Accordingly, the first and second agents in the droplet encapsulate of the invention may be HMR 1826 and human beta-glucuronidase.

In another embodiment, the droplet encapsulate of the invention is used as a vehicle for the simultaneous delivery of a prodrug and its activator. In this application, one inner droplet of a multisome contains a prodrug, and another inner droplet of the same multisome contains its corresponding activator. Jointly releasing the contents upon some external stimulus would allow the prodrug and activator to combine, producing the active species in situ. This would allow the administration of drugs that are, for example, too unstable or insoluble to be delivered in the active state. This approach could also be used to encapsulate a prodrug impermeant to the multisomal bilayer, which is converted to an active drug that is permeant to cell membranes.

Thus, in one embodiment, the first agent is an inactive form of a drug which is capable of being activated by an activator, and the second agent is said activator. The activator may for instance be an enzyme. The inactive form of said drug may be referred to as a prodrug.

Typically, the prodrug is of a drug which is too unstable or insoluble to be delivered in the active state. Thus, in one embodiment the prodrug is miproxifene phosphate and the activator is an alkaline phosphatase. Miproxifene phosphate is the inactive phosphate ester of the anticancer agent miproxifene, and has 1,000-fold greater aqueous solubility than miproxifene. It is converted to the active species by alkaline phosphatases.

Prodrugs particularly suited to delivery in multisomes are those whose activators are not found endogenously. Some prodrug strategies rely on the delivery of an exogenous activator following the systemic, targeted delivery of a prodrug. Xu, G. & McLeod, H. L. "Strategies for enzyme/prodrug cancer therapy" Clin. Cancer Res. 7, 3314-3324 (2001) presents examples of the prodrug/activator combinations used in these strategies, which could be used as the first and second agents in the droplet encapsulates of the invention. The prodrug may for instance be HMR 1826, in which case the activator is human beta-glucuronidase.

Conversely, the droplet encapsulate of the invention could be used to deliver active drugs that are deactivated by another species, giving precise control over the lifetime of the active drug. Bodor, N. & Buchwald, P. "Soft drug design: general principles and recent applications" Med. Res. Rev. 20, 58-101 (2000) presents several examples of soft drugs, which are typically deactivated by endogenous species. Multisomes can allow the use of exogenous deactivators, or higher concentrations of endogenous deactivators than would otherwise be found in the body.

Thus, in another embodiment, the first agent is a drug that is capable of being deactivated by a deactivator compound, and the second agent is said deactivator compound. For instance, the first agent may be the drug mivacurium chloride and the second agent may be the corresponding enzyme deactivator human plasma cholinesterase.

In addition to drugs, multisomes can also be used to carry a contrast agent for some medical imaging modality. This will allow the precise determination of the distribution of the drugs contained in the multisome, while keeping the marker separate from the drugs until the moment of delivery. It should be possible to encapsulate contrast agents for various medical imaging modalities, which would allow the visualization of how drug-carrying multisomes are distributed within the body. The use of separate compartments for the drug and the tracer would prevent any chemical reaction between the two. Contrast agents could be included for radiography (e.g. diatrizoate, iopamidol, iodixanol), MRI (e.g. gadodiamide, gadopentetic acid), ultrasound (e.g. air bubbles), or radionuclides may be encapsulated for positron emission tomography (e.g. fludeoxyglucose ($^{18}$F)), scintigraphy (e.g. iobenguane) or single-photon emission computed tomography (e.g. Na$^{123}$I).

Accordingly, in another embodiment, the first agent is a drug and the second agent is a contrast agent suitable for monitoring the biodistribution of the drug. The contrast agent may for instance be a contrast agent for radiography (e.g. diatrizoate, iopamidol, iodixanol), magnetic resonance imaging (MM) (e.g. gadodiamide, gadopentetic acid), or ultrasound (e.g. air bubbles), or radionuclides may be encapsulated for positron emission tomography (e.g. fludeoxyglucose ($^{18}$F)), scintigraphy (e.g. iobenguane) or single-photon emission computed tomography (e.g. Na$^{123}$I).

A multisome might be made to contain non-drug compounds and drugs in separate compartments (including the oil phase). One possibility for the non-drug compound is a contrast agent suitable for monitoring the biodistribution of the drug, as discussed above. Other possibilities are as follows:

Targeting agents [Pouponneau, P., Leroux, J. C., Soulez, G., Gaboury, L. & Martel, S. Co-encapsulation of magnetic nanoparticles and doxorubicin into biodegradable microcarriers for deep tissue targeting by vascular MRI navigation. *Biomaterials* 32, 3481-3486 (2011)]: A recent study encapsulated doxorubicin and magnetic nanoparticles (FeCo) in poly(lactic-co-glycolic acid) microspheres, and used a modified MRI scanner to simultaneously image and steer the microparticles through blood vessels in vivo. A similar principle could be applied to the droplet encapsulates of the invention, in which case the magnetic particles and drug could be encapsulated in separate compartments.

Triggers: In addition to encapsulating a drug, a multisome could contain a substance that responds to an external trigger in such a way as to induce release of the drug. This substance might for instance be ferromagnetic particles, which could be heated by externally applied alternating magnetic fields as used for MRI.

Cells: It might be possible to encapsulate living cells in multisomes, and release them into the environment, together with compounds encapsulated separately in the same multisomes, to trigger a particular behaviour.

Accordingly, in another embodiment, the first agent is a drug and the second agent is a targeting agent, a trigger or a living cell. The targeting agent or trigger may be selected from any of those listed above.

The droplet encapsulates of the invention may contain three or more different agents, in different parts of the encapsulate.

Accordingly, in another embodiment, the droplet encapsulate is a droplet encapsulate as defined above which comprises a plurality of said aqueous droplets within the peripheral layer, and which further comprises a first agent, a second agent, and a third agent in separate parts of the encapsulate. The parts of the encapsulate referred to here include the hydrophobic medium of the drop, and the different aqueous droplets.

For instance, in one embodiment the first agent is present in one of the aqueous droplets in the encapsulate, the second agent is present within the hydrophobic medium, and the third agent is present in another of the aqueous droplets. In another embodiment, the droplet encapsulate of the invention is a droplet encapsulate which comprises more than two of said aqueous droplets, and the first, second and third agents are within different aqueous droplets of the encapsulate.

The third agent may for instance be a therapeutic agent, a diagnostic agent, a drug for use together in a combination therapy with the first or second agent, a prodrug, an activator compound for a prodrug, a deactivator compound for an active drug, or a contrast agent for monitoring the biodistribution of the first or second agent. Alternatively, the first, second and third agents may be reactant compounds for reacting together in a chemical reaction.

Typically the first, second and third agents are present in the droplet encapsulate in a predetermined proportion. As mentioned above, the delivery of several drugs encapsulated in different compartments of a single multisome (including in the hydrophobic phase) would allow precise control over dosage proportions. This may be beneficial for the delivery of drugs with independent mechanisms of action. Also, their uptake by cells in fixed proportions could be expected to increase their overall efficacy, and decrease the probability of resistance developing to any one of the drugs.

Some non-limiting examples of combinations of three or more drugs which can be employed in the droplet encapsulate of the invention (for instance each drug in a separate compartment) include the following cancer therapies: ABVD (doxorubicin, bleomycin, vinblastine and dacarbazine) for Hodgkin's lymphoma, CHOP (cyclophosphamide, doxorubicin, vincristine and prednisone) for non-Hodgkin's lymphoma, and CMF (cyclophosphamide, methotrexate and 5-fluorouracil) for breast cancer.

It is also reasonable to expect that multisomes might be used to encapsulate substances not presently delivered in combination. The ideal combination of compounds would consist of parent compounds that are stable separately, and following triggered release from the multisome, react to form an active, unstable compound. The instability of the active compound would ensure that areas far from the triggered region are not affected.

The stabilities of one or more of the bilayers in the droplet encapsulate of the invention may in some embodiments be sensitive to a stimulus, for instance an external stimulus, such that when the bilayer in question is exposed to that stimulus it may release its contents into the surrounding environment. The bilayer which is sensitive to the stimulus may be a bilayer formed at an interface between an aqueous droplet and the peripheral layer, i.e. an "external bilayer". In that case, exposing the droplet encapsulate to the stimulus in question can cause the external bilayer to leak or rupture and the contents of the aqueous droplet may be released from the droplet encapsulate. Alternatively, the bilayer which is sensitive to the stimulus may be a bilayer which is formed at an interface between two aqueous droplets in the encapsulate, i.e. an "internal bilayer". In that case, exposing the bilayer to the stimulus can cause the internal bilayer to leak or rupture, allowing the contents of the two aqueous droplets to combine.

The external bilayers of two or more droplets within the same droplet encapsulate may for instance be sensitive to the same stimulus and the droplets may therefore be capable of releasing their contents simultaneously upon exposure to that stimulus. In other embodiments, the external bilayers of two or more droplets within the same droplet encapsulate may have different stabilities, and the droplets may therefore be capable of releasing their contents into the environment at different times, in response to different stimuli, or for instance in response to different levels or magnitudes of the same stimulus. For example, a first droplet in the droplet encapsulate may be capable of releasing its contents in response to a change in pH, whereas a second droplet in the encapsulate may be capable of releasing its contents in response to a change in temperature. Alternatively, two or more droplets within the same droplet encapsulate may release their contents in response to different levels of the same stimulus. Thus, for example, a first droplet may be capable of releasing its contents in response to a relatively small change in pH or temperature, whereas a second droplet may only release its contents in response to a larger change in pH or temperature. Additionally or alternatively, one or more of the internal bilayers in the encapsulate may be sensitive to a stimulus such that the contents of two or more aqueous droplets within the encapsulate may be combined.

Thus, in some embodiments, multiple droplets within the same droplet encapsulate are capable of releasing their contents into the environment simultaneously, e.g. upon exposure to an external stimulus such as a change in pH or temperature. The contents referred to here may be first, second and/or third agents as defined above, or any other compound or composition for delivery from within the droplet encapsulate.

Accordingly, in embodiments of the droplet encapsulate of the invention described herein in which the droplet encapsulate comprises a bilayer of said non-polymeric amphipathic molecules, the stability of said bilayer may be sensitive to a stimulus. The stimulus is typically an external stimulus.

Also, in embodiments of the droplet encapsulate of the invention which are described herein, in which the droplet encapsulate comprises a plurality of bilayers of said non-polymeric amphipathic molecules, the stabilities of one or more of said bilayers may be sensitive to a stimulus. In some embodiments, the stability of at least one of said bilayers is sensitive to a stimulus. The stimulus is typically an external stimulus. In other embodiments, the stability of more than one of said bilayers is sensitive to a stimulus. In other embodiments, the stabilities of each and every one of said bilayers is sensitive to a stimulus. The stimuli to which the bilayers are sensitive may be the same or different.

In embodiments of the droplet encapsulate of the invention described herein in which part of the outer layer of an aqueous droplet contacts the peripheral layer, thereby forming a bilayer of said non-polymeric amphipathic molecules at an interface between the aqueous droplet and the peripheral layer (i.e. an "external bilayer"), the stability of said bilayer may be sensitive to a stimulus. The stimulus is typically an external stimulus.

Also, in embodiments of the droplet encapsulate of the invention described herein in which the droplet encapsulate comprises a plurality of aqueous droplets within the peripheral layer, wherein the outer layer of more than one of said aqueous droplets contacts the peripheral layer to form a plurality of external bilayers, the stability of one or more of said bilayers may be sensitive to a stimulus. The stimulus is typically an external stimulus. In some embodiments, the stability of at least one of said bilayers is sensitive to a stimulus. In other embodiments, the stability of more than one of said bilayers is sensitive to a stimulus. In other embodiments, the stabilities of each and every one of said bilayers is sensitive to a stimulus. The stimuli to which the external bilayers are sensitive may be the same or different.

In embodiments of the droplet encapsulate of the invention described herein in which the droplet encapsulate comprises a plurality of aqueous droplets within the peripheral layer, wherein part of the outer layer of a first of said aqueous droplets contacts part of the outer layer of a second of said aqueous droplets, thereby forming a bilayer of the non-polymeric amphipathic molecules at an interface between said first and second aqueous droplets (an "internal bilayer"), the stability of said bilayer may or may not be sensitive to a stimulus. In some embodiments, the stability of said internal bilayer is sensitive to an external stimulus.

Furthermore, in embodiments of the droplet encapsulate of the invention described herein in which the droplet encapsulate comprises a plurality of said internal bilayers of non-polymeric amphipathic molecules, the stability of one or more of said bilayers may be sensitive to a stimulus. The stimulus may be an external stimulus. In some embodiments, the stability of at least one of said internal bilayers is sensitive to a stimulus. In other embodiments, the stabilities of each and every one of said internal bilayers is sensitive to a stimulus. The stimuli to which the internal bilayers are sensitive may be the same or different.

Typically, in these embodiments, the droplet encapsulate of the invention is one which further comprises an agent for delivery, such as a therapeutic agent, prodrug, diagnostic agent, or contrast agent, as described above. Alternatively, it may be one which comprises two or more such agents for delivery. The two or more agents may be in separate parts of the encapsulate, as defined above, or in the same part. For instance, the droplet encapsulate of the invention may be one which comprises a first agent and a second agent in separate parts of the encapsulate, as defined above, or one which comprises first, second and third agents in separate parts of the encapsulate, as defined above.

As mentioned above, the stimulus may be a change in pH (such as an increase or decrease in pH), a change in temperature (such as heating or cooling), but any other suitable stimulus may be used. Other suitable stimuli that may be used include but are not limited to ultrasound; a mechanical stimulus; shear flow; a critical concentration of a species (e.g. a critical concentration of divalent cations); a magnetic field; an electric field; and electromagnetic radiation (light), including but not limited to infrared, UV, X-rays and gamma rays. Additionally or alternatively, the stabilities of the bilayers of non-polymeric amphipathic molecules may be controlled by including a molecule in one or more of the bilayers, such as a lipid or protein, that recognises a surface species on a target cell. The surface species may itself be a protein. The response to this recognition might be immediate destabilization of the bilayer, or it might be indirect. Accordingly, in one embodiment, the non-polymeric amphipathic molecules of said bilayer or bilayers comprise a molecule that recognises a surface species on a target cell, wherein the response to the recognition comprises destabilization of the bilayer or bilayers. The response may comprise immediate destabilization of the bilayer, or it may comprise indirect destabilization of the bilayer. The molecule may for instance be a lipid or a protein.

Usually, however, the external stimulus is a change in pH or a change in temperature.

In one embodiment, the external stimulus is a change in pH. The change in pH to which the bilayer or bilayers of non-polymeric amphipathic molecules are sensitive may be a decrease in pH from above 7.5 to below 7.5, or for instance a decrease in pH from above 7.0 to below 7.0, or for instance a decrease in pH from above 7.0 to below 6.5. More typically, said change in pH is a decrease in pH from above 7.0 to below 6.0, or for instance a decrease in pH from above 7.0 to below 5.5. In another embodiment, said change in pH is a decrease in pH from above 7.5 to below 7.0, or for instance a decrease in pH from above 7.5 to below 6.5, or for instance a decrease in pH from above 7.5 to below 6.0, or for instance a decrease in pH from above 7.5 to below 5.5. Thus, in some embodiments the non-polymeric amphipathic molecules of said bilayer or bilayers are selected such that the bilayer or bilayers rupture or leak upon said change in pH. By "rupture" herein is meant rupture irreversibly so that the entire contents of the droplet encapsulate are released into the environment. The term "leak" in this context means that some of the contents are released from the droplet encapsulate, for instance when the structure of the bilayer or bilayers of the droplet encapsulate become less stable and therefore leak their contents but the overall structure of the droplet encapsulate remains more or less intact.

In one embodiment of the droplet encapsulate of the invention, said bilayer or bilayers of non-polymeric amphipathic molecules are capable of rupturing or leaking upon exposure to a pH of less than 7.5. In another embodiment of the droplet encapsulate of the invention, said bilayer or bilayers of non-polymeric amphipathic molecules are capable of rupturing or leaking upon exposure to an acidic pH, i.e. a pH less than 7.0. Typically, in this embodiment, said acidic pH is a pH of 6.5 or below. More typically, said acidic pH is a pH of 6.0 or below, or for instance a pH of 5.5 or below.

This can be achieved by employing a pH-sensitive lipid in the bilayer or bilayers in question. The pH-sensitive lipid may for instance be a fatty acid having a $pK_a$ when incorporated in a bilayer at or around the pH at which it is desired that the bilayer or bilayers of non-polymeric amphipathic molecules should become unstable. At pH's that are greater than the $pK_a$ of the fatty acid, the fatty acid will be deprotonated and therefore strongly amphipathic, and will therefore be suitable for stabilising an internal or external bilayer of a multisome. At pH's that are lower than the $pK_a$, on the other hand, the fatty acid will be protonated and less amphipathic, thereby destabilising any bilayer in which it is present. As the skilled person will appreciate, the $pK_a$ of a fatty acid in a bilayer is shifted compared to the $pK_a$ of the free fatty acid in aqueous solution. Thus, each $pK_a$ referred to herein is the $pK_a$ of the fatty acid when it is present in a bilayer of non-polymeric amphipathic molecules in the droplet encapsulate. The skilled person can readily measure the $pK_a$ of a fatty acid in a bilayer using methods which are known in the art, for instance by using known spectroscopic methods, in particular known methods which employ NMR spectroscopy.

Thus, in one embodiment of the droplet encapsulate of the invention, the non-polymeric amphipathic molecules of the bilayer or bilayers comprise a pH-sensitive lipid.

Typically, the pH-sensitive lipid is a fatty acid. In one embodiment the pH-sensitive lipid is a fatty acid having a $pK_a$ equal to or less than about 8.5.

In another embodiment, the pH-sensitive lipid is a fatty acid having a $pK_a$ equal to or less than about 8.0. In yet another embodiment, the pH-sensitive lipid is a fatty acid having a $pK_a$ equal to or less than about 7.5.

The pH-sensitive lipid may for instance be a fatty acid having a $pK_a$ of from 6 to 8, for instance a fatty acid having a $pK_a$ of about 7.5. Suitable fatty acids include oleic acid, which itself has a $pK_a$ of about 7.5 when it is present in a bilayer.

In one embodiment of the droplet encapsulate of the invention, the non-polymeric amphipathic molecules of the bilayer or bilayers comprise a pH-sensitive lipid, as defined above, and a further lipid which is not sensitive to pH. Typically, the further lipid which is not sensitive to pH is a lipid which favours a non-bilayer state but which forms a stable bilayer in combination with the pH-sensitive lipid at neutral pH. Typically, the further lipid which is not sensitive to pH is a phospholipid. More typically, it is a glycerophospholipid. A suitable glycerophospholipid for use in this context would be 1,2-dioleoyl-sn-glycero-3-phosphoethanolamine (DOPE).

Thus, in one embodiment of the droplet encapsulate of the invention, the non-polymeric amphipathic molecules of the bilayer or bilayers comprise a pH-sensitive lipid, as defined above, and 1,2-dioleoyl-sn-glycero-3-phosphoethanolamine (DOPE). Thus, for instance, the non-polymeric amphipathic molecules in the droplet encapsulate of the invention may comprise a mixture of DOPE and oleic acid. In one embodiment of the droplet encapsulate of the invention, the non-polymeric amphipathic molecules of the bilayer or bilayers comprise DOPE and oleic acid in a molar ratio of from 1:1 to 3:1, preferably in a molar ratio of about 2:1.

In another embodiment, the bilayer or bilayers of non-polymeric amphipathic molecules in the droplet encapsulate of the invention are temperature-sensitive. Thus, the bilayer or bilayers of non-polymeric amphipathic molecules may in some embodiments be capable of rupturing or leaking upon exposure to an elevated temperature or upon exposure to a reduced temperature. In one embodiment, the bilayer or bilayers of non-polymeric amphipathic molecules are capable of rupturing or leaking upon exposure to an elevated temperature. In order to be useful for in vivo drug delivery the elevated temperature is typically around or above body temperature, i.e. around or above 37° C. Thus, in one embodiment of the droplet encapsulate of the invention, the bilayer or bilayers of non-polymeric amphipathic molecules are capable of rupturing or leaking upon exposure to a temperature equal to or greater than about 37° C. In another embodiment, the bilayer or bilayers of non-polymeric amphipathic molecules are capable of rupturing or leaking upon exposure to a temperature equal to or greater than about 40° C., or for instance equal to or greater than about 42° C. Such embodiments are useful in conjunction with local mild hyperthermia of up to 42° C., producing a corresponding local enhancement in drug release from multisomes in vivo.

Typically, in these embodiments, the bilayer or bilayers of non-polymeric amphipathic molecules comprise a temperature-sensitive lipid. Alternatively, the bilayer or bilayers of non-polymeric amphipathic molecules may comprise a temperature-sensitive lipid and a further lipid. Typically, the temperature-sensitive lipid is a phospholipid, more typically a glycerophospholipid. The further lipid is usually a phospholipid.

Typically, the temperature-sensitive lipid is a lipid that has a melting transition temperature $T_m$ at or around the temperature of interest at which it is desired that the layers of non-polymeric amphipathic molecules should become unstable. Liposomes made with such lipids are known to have a local maximum of permeability around $T_m$, attributable to the boundaries between the solid and fluid phases of the liposomal bilayer.

That said, the bursting temperature of the droplet encapsulate may be considerably different from, usually lower than, the transition temperature of the temperature-sensitive lipid. This is usually the case if a further lipid is present, as the presence of a further lipid can have the effect of broadening the melting transition of the temperature-sensitive lipid, and/or decreasing the peak transition temperature of the temperature-sensitive lipid. Second, the extent of the release of contents from temperature-sensitive liposomes has been shown to increase with their size, so for a given temperature-sensitive lipid the bursting temperature of the droplet encapsulate of the invention may decrease as the size of the droplet encapsulate increases.

Thus, typically, the temperature-sensitive lipid employed in the bilayer or bilayers of the droplet encapsulates of the invention is a lipid which has a melting transition temperature, $T_m$, which is equal to or greater than the temperature of interest at which it is desired that the layers of non-polymeric amphipathic molecules should become unstable.

Accordingly, the temperature-sensitive lipid may be a lipid having a melting transition temperature, $T_m$, which is equal to or greater than about 37° C. More typically, it is a lipid having a melting transition temperature, $T_m$, which is equal to or greater than about 40° C. Thus, it can be a lipid having a melting transition temperature, $T_m$, of from 37° C. to 90° C., or for instance from 40° C. to 70° C. In one embodiment, the temperature-sensitive lipid is a lipid which has a melting transition temperature, $T_m$, of from 40° C. to 60° C.

Typically, the temperature-sensitive lipid is a glycerophospholipid. It may for instance be 1,2-distearoyl-sn-glycero-3-phosphocholine (DSPC) or 1,2-dipalmitoyl-sn-glycero-3-phosphocholine (DPPC). If a further lipid is present in combination with the temperature-sensitive lipid, it is typically a glycerophospholipid, for instance a glycerophospholipid of formula (I) defined herein. The further lipid may for instance be 1,2-diphytanoyl-sn-glycero-3-phosphocholine (DPhPC).

Thus, in one embodiment, the bilayer or bilayers of non-polymeric amphipathic molecules in the droplet encapsulate of the invention comprise 1,2-distearoyl-sn-glycero-3-phosphocholine (DSPC) and 1,2-diphytanoyl-sn-glycero-3-phosphocholine (DPhPC). Typically, in this embodiment, the non-polymeric amphipathic molecules comprise 1,2-distearoyl-sn-glycero-3-phosphocholine (DSPC) and 1,2-diphytanoyl-sn-glycero-3-phosphocholine (DPhPC) in a molar ratio of from 1:1 to 5:1, preferably in a molar ratio of about 3:1.

In another embodiment, the non-polymeric amphipathic molecules comprise 1,2-dipalmitoyl-sn-glycero-3-phosphocholine (DPPC) and 1,2-diphytanoyl-sn-glycero-3-phosphocholine (DPhPC).

The droplet encapsulates of the invention are stable in aqueous and other hydrophilic environments.

Accordingly, the present invention provides a composition which comprises: (a) a droplet encapsulate of the invention as defined herein, and (b) a hydrophilic carrier.

Typically, the composition comprises a plurality of droplet encapsulates of the invention as defined herein and the hydrophilic carrier.

The hydrophilic carrier may be any suitable hydrophilic medium. Typically, it is aqueous. Thus, the hydrophilic carrier typically comprises water. The hydrophilic carrier may for instance be pure water, or an aqueous solution. Typically, it is an aqueous buffer solution. Hydrophilic materials other than water may however be employed, for instance hydrophilic ionic liquids. Thus in one embodiment the hydrophilic carrier comprises an ionic liquid. For certain applications the hydrophilic carrier is desirably pharmaceutically acceptable.

Thus, the invention further provides a pharmaceutical composition which comprises: (a) a droplet encapsulate of the invention as defined herein, and (b) a pharmaceutically acceptable hydrophilic carrier. Typically, in this aspect of the invention, the droplet encapsulate of the invention is one which further comprises an agent for delivery in vivo, such as a therapeutic agent, prodrug, diagnostic agent, or contrast agent, as described above. Alternatively, it may be one which comprises two or more agents in separate parts of the encapsulate, as defined above. For instance, the droplet encapsulate of the invention may be one which comprises a first agent and a second agent in separate parts of the encapsulate, as defined above, or one which comprises first, second and third agents in separate parts of the encapsulate, as defined above.

The invention further provides a droplet encapsulate of the invention as defined herein, or a composition of the invention as defined herein, for use in a method for treatment of the human or animal body by therapy. Typically, in this aspect, the droplet encapsulate of the invention, or the or each droplet encapsulate in the composition, is a droplet encapsulate of the invention as defined above which further comprises a therapeutic agent or prodrug. It may for instance be one which comprises two or more agents in separate parts of the encapsulate, as defined above. For instance, the droplet encapsulate of the invention may be one which comprises a first agent and a second agent in separate parts of the encapsulate, as defined above, or one which comprises first, second and third agents in separate parts of the encapsulate, as defined above.

The invention further provides a droplet encapsulate of the invention as defined herein, or a composition of the invention as defined herein, for use in a diagnostic method practised on the human or animal body. Typically, in this aspect, the droplet encapsulate of the invention, or the or each droplet encapsulate in the composition, is a droplet encapsulate of the invention as defined above which further comprises a diagnostic agent or a contrast agent. It may for instance be one which comprises two or more agents in separate parts of the encapsulate, as defined above. For instance, the droplet encapsulate of the invention may be one which comprises a first agent and a second agent in separate parts of the encapsulate, as defined above, or one which comprises first, second and third agents in separate parts of the encapsulate, as defined above.

Further applications of multisomes range from providing a novel platform for the fundamental study of membrane proteins, to acting as multi-compartment protocellular chassis for "bottom-up" synthetic biology. In particular, the droplet encapsulates of the invention can be used to prepare protocells or aggregates of protocells (prototissue).

Thus, the invention provides the use of a droplet encapsulate of the invention as defined herein, or a composition of the invention as defined herein, in synthetic biology.

Further provided is the use of a droplet encapsulate of the invention as defined herein, or a composition of the invention as defined herein, in a method of preparing a protocell.

Further provided is the use of a droplet encapsulate of the invention as defined herein, or a composition of the invention as defined herein, in a method of preparing prototissue.

A protocell can be prepared by removing or reducing the amount of the hydrophobic medium from a droplet encapsulate of the invention, for instance a droplet encapsulate containing only one aqueous droplet within the peripheral layer. The hydrophobic medium can be removed from around the aqueous droplet by allowing it to evaporate and/or by removing it mechanically, for instance with a micropipette. As more and more of the hydrophobic medium is removed, the peripheral layer of non-polymeric amphipathic molecules moves closer and closer to the outer layer of the aqueous droplet, and it eventually forms a bilayer with the non-polymeric amphipathic molecules of the outer layer of the aqueous droplet. Oil removal is not required for two monolayers to adhere to form a bilayer. However, oil removal will result in further adhesion of monolayers into a bilayer. Thus, removal or reducing the amount of hydrophobic medium can cause a bilayer to be formed around the surface of the aqueous droplet, to produce a cell-like structure which can itself be used as a protocell or can be used to produce a protocell. Removal of all of the oil will cause a bilayer to be formed completely around the surface of the aqueous droplet. The bilayer forms quickly after removing or reducing the amount of hydrophobic medium because in the absence of a certain amount of intervening hydrophobic medium the bilayer has a lower free energy than two monolayers and thus has a negative free energy of formation; it is therefore a spontaneous event. The bilayer can also be formed without removing or reducing the amount of the hydrophobic medium; as noted before, bilayer formation simply requires that the two monolayer-coated surfaces approach each other, which can happen spontaneously if the aqueous droplet is not neutrally buoyant in the oil drop; the removal of oil however will cause monolayers to adhere into a bilayer further.

Prototissue can be produced by an analogous method starting with a droplet encapsulate of the invention which comprises a chain or network of the aqueous droplets. In that case the aqueous droplets already have bilayers formed between them; however, parts of the outer layers of the chain or network will still be in monolayer form, exposed to the hydrophobic medium in the multisome. Reducing or removing the hydrophobic medium from around the chain or network will cause the peripheral monolayer to move closer and closer to the outer monolayer surfaces of the aqueous droplets in the chain or network, and eventually the peripheral monolayer will combine with the outer monolayers of the aqueous droplets to form a bilayers. Thus, removing or reducing the amount of hydrophobic medium can cause a bilayer to be formed around the surface of the chain or network, to produce a network of cell-like structures which can be used as the basis for producing prototissue. Removing all of the oil will cause a bilayer to be formed completely around the surface of the chain or network. As noted above, the bilayer can also be formed without removing or reducing the amount of hydrophobic medium, but the removal of oil can induce monolayers to adhere into a bilayer further.

Accordingly, the invention further provides a method of preparing a protocell, the method comprising: providing a droplet encapsulate of the invention as defined above, and allowing the outer layer of the aqueous droplet to come into contact with said peripheral layer of non-polymeric amphipathic molecules, or bringing the outer layer of the aqueous droplet into contact with said peripheral layer of non-polymeric amphipathic molecules, and thereby forming a bilayer of non-polymeric amphipathic molecules around at least part of the surface of the aqueous droplet.

As mentioned above, bilayer formation may be aided by removing some or all of the hydrophobic medium from the droplet encapsulate of the invention. Thus, in some embodiments, the method of preparing a protocell comprises: removing some or all of the hydrophobic medium from a droplet encapsulate of the invention as defined above, so that said peripheral layer of non-polymeric amphipathic molecules sticks to the outer layer of said aqueous droplet, thereby forming a bilayer of non-polymeric amphipathic molecules around at least part of the surface of the aqueous droplet.

Typically, in the method of the invention for preparing a protocell, the droplet encapsulate of the invention is one which contains only one aqueous droplet.

The invention further provides a protocell which is obtainable by the method of the invention as defined above for preparing a protocell.

Further provided is a protocell comprising a droplet encapsulate of the invention as defined herein, wherein said peripheral layer of non-polymeric amphipathic molecules contacts the outer layer of said aqueous droplet and thereby forms a bilayer of non-polymeric amphipathic molecules around part of the aqueous droplet. Typically, the droplet encapsulate of the invention is one which contains only one aqueous droplet.

The aqueous droplet in the droplet encapsulate of the invention can detach from the oil drop, when shear flow is applied externally (for instance to the external aqueous phase), to produce an oil drop and a separate giant unilamellar vesicle. The vesicle may for instance be used as a protocell.

Thus, the invention further provides a method of preparing a vesicle, which method comprises applying shear flow to a droplet encapsulate of the invention.

Further provided is a method of preparing a protocell, which method comprises applying shear flow to a droplet encapsulate of the invention.

The invention further provides a protocell which is obtainable by the method of the invention as defined above for preparing a protocell.

The invention further provides a method of preparing a prototissue, which method comprises: providing a droplet encapsulate of the invention as defined herein which comprises a plurality of said aqueous droplets, and allowing the outer layers of the aqueous droplets to come into contact with the peripheral layer of non-polymeric amphipathic molecules or bringing the outer layers of the aqueous droplets into contact with the peripheral layer of non-polymeric amphipathic molecules, and thereby forming a bilayer of non-polymeric amphipathic molecules around at least part of the surface of the plurality of aqueous droplets.

As mentioned above, bilayer formation may be aided by removing some or all of the hydrophobic medium from the droplet encapsulate of the invention. Thus, in one embodiment, the method of preparing a prototissue comprises: removing some or all of the hydrophobic medium from a droplet encapsulate of the invention as defined above which comprises a plurality of said aqueous droplets, so that the peripheral layer of non-polymeric amphipathic molecules sticks to the outer layers of said aqueous droplets, thereby forming a bilayer of non-polymeric amphipathic molecules around at least part of the surface of the plurality of aqueous droplets.

Typically, in the method of the invention for preparing a prototissue, the droplet encapsulate of the invention is one which comprises two or more aqueous droplets, or for instance more than two aqueous droplets, which are in contact with one another in a chain or network, wherein a part of the outer layer of each droplet in the chain or network contacts a part of the outer layer of another droplet in the chain or network, thereby forming bilayers of the non-polymeric amphipathic molecules at interfaces between the droplets in the chain or network.

Further provided is a prototissue which is obtainable by the method of the invention defined above for preparing a prototissue.

The invention also provides a prototissue comprising a droplet encapsulate of the invention as defined above, which droplet encapsulate comprises a plurality of said aqueous droplets, wherein the peripheral layer of non-polymeric amphipathic molecules contacts the outer layers of said aqueous droplets, thereby forming a bilayer of said non-polymeric amphipathic molecules around at least part of the surface of the plurality of aqueous droplets.

The invention also provides a prototissue comprising a plurality of protocells of the invention as defined above.

By using membrane proteins and multiple droplets linked by bilayers, multisomes can sense their environment, process information, and contingently deliver materials to the surroundings, as illustrated in FIG. 1A hereinbelow. Accordingly, the invention further provides the use of a droplet encapsulate of the invention as defined herein for trafficking a molecule between droplets in the encapsulate and/or for delivering a molecule from a droplet in the encapsulate to the external environment. More generally, the invention further provides the use of a droplet encapsulate of the invention as defined herein for exchanging materials between encapsulated droplets and the environment.

Multisomes may also be used as platforms for the fundamental study of membrane proteins: the droplet encapsulates of the invention represent a simple way to make a curved lipid bilayer, with various ways of controlling the bilayer curvature. Further, they allow two lipid bilayers to be placed in close apposition, through virtually any means of micro- and nano-manipulation, facilitating a wide range of experiments. These experiments include investigation and/or screening of membrane proteins, investigation and/or screening of analytes which interact with membrane proteins, and investigation and/or screening of curved bilayers in the droplet encapsulate. Indeed droplet encapsulates of the invention may be used to study any bilayer phenomena in general, typically involving a process occurring at or through the bilayer.

Accordingly, the invention further provides the use of a droplet encapsulate of the invention as defined herein in a method of investigating and/or screening a membrane protein. The droplet encapsulates of the invention are especially useful for studying membrane proteins that span two closely-apposed bilayers, as is explained further below. Thus, in one embodiment the membrane protein is one which spans two bilayers.

In another aspect the invention provides the use of a droplet encapsulate of the invention as defined herein in a method of investigating and/or screening an analyte which interacts with a membrane protein.

In another aspect the invention provides the use of a droplet encapsulate of the invention as defined herein in a method of investigating and/or screening a bilayer of non-polymeric amphipathic molecules.

The droplet encapsulates of the invention can also be used to study the properties of the membrane protein inserted into a bilayer therein. For example, the voltage dependence of the properties of the membrane protein may be determined. Techniques for studying membrane proteins in lipid bilayers are well known in the art. The function of a channel or pore may be determined by measuring, for example, an ionic current flowing across the lipid bilayer through a membrane protein. The function of a transporter may be determined by measuring the amount of a molecule translocated across the lipid bilayer, for example by mass spectrometry or ELISA or by using a substrate which is tagged fluorescently or radioactively.

As mentioned above, the droplet encapsulates of the invention are especially useful for studying membrane proteins that span two bilayers. For example, droplet encapsulates of the invention can be used to study pore-forming protein complexes that span two lipid bilayers, such as gap junctions and nuclear pores, at the single-molecule level by positioning two multisomes with single inner droplets such that their bilayers are apposed.

Accordingly, in another aspect, the invention provides the use of a first droplet encapsulate of the invention as defined above and a second droplet encapsulate of the invention as defined above, for investigating and/or screening a membrane protein complex which spans two bilayers of said non-polymeric amphipathic molecules,
wherein in each of said first and second droplet encapsulates, a said aqueous droplet is situated at the edge of the drop, wherein part of the outer layer of the aqueous droplet contacts said peripheral layer, thereby forming a bilayer of said non-polymeric amphipathic molecules at an interface between the aqueous droplet and the peripheral layer,
wherein said first and second droplet encapsulates are positioned such that the bilayer of the first droplet encapsulate and the bilayer of the second droplet encapsulate are apposed, and wherein a membrane protein spans said two apposed bilayers.

Networks of aqueous droplets joined by droplet interface bilayers can be constructed that exploit a variety of membrane pumps, channels and pores to act as light sensors, batteries, and electrical devices. This is described in Holden, M. A. et al., J. Am. Chem. Soc. 129, 8650-8655 (2007), and Maglia, G. et al. Nat. Nanotechnol. 4, 437-440 (2009), which relate to the construction of such droplet networks in a bulk oil phase. Such droplet networks can also be constructed within multisomes, using the methods described herein, to provide droplet encapsulates of the invention that function as sensors, batteries, or electrical devices.

Accordingly, the invention further provides the use of droplet encapsulate of the invention as defined herein as a sensor, battery, or electrical device. Further provided is a sensor, a battery, or an electrical device, comprising a droplet encapsulate of the invention as defined herein.

Multisomes that communicate with each other through a bulk hydrophilic (typically aqueous) phase containing the multisomes are also envisaged, wherein a first multisome "transmits" a signal by releasing species into the bulk solution, either by diffusion through pores in the external bilayers, or by pH- or temperature-induced bursting, and a second multisome then "receives" the signal. The second multisome can receive the signal either by diffusion of the species into the aqueous droplets of the second multisome through pores in the external bilayers, or by the use of a further species in the external lipid monolayer of the second multisome which is sensitive to the signal.

Multisomes that communicate with external chemical and biological materials are also envisaged, including for example multisomes which communicate with biological cells, tissue or organisms. In one embodiment, for instance, the droplet encapsulate of the invention is capable of communicating with a nerve ending, by releasing a neurotransmitter which the nerve ending is capable of detecting. The neurotransmitter could be released either by diffusion through pores in the external bilayers of the multisome, or by pH- or temperature-induced bursting. Once released by the multisome, the neurotransmitter is then detected by the nerve ending, and a signal is thereby transmitted from the multisome to the nerve.

The droplet encapsulates of the invention can be produced by the process of the invention for producing a droplet encapsulate, which droplet encapsulate comprises:
a drop of a hydrophobic medium;
a peripheral layer of non-polymeric amphipathic molecules around the surface of the drop; and
an aqueous droplet within the peripheral layer, the aqueous droplet comprising: (a) an aqueous medium and (b) an outer layer of non-polymeric amphipathic molecules around the surface of the aqueous medium;
which process comprises:
transferring an aqueous droplet, which aqueous droplet comprises (a) an aqueous medium and (b) an outer layer of non-polymeric amphipathic molecules around the surface of the aqueous medium, into a drop of a hydrophobic medium, wherein said a drop of a hydrophobic medium has a peripheral layer of non-polymeric amphipathic molecules around its surface.

Usually, the process of the invention comprises the following steps:
(i) introducing a drop of a hydrophobic medium into a hydrophilic carrier, in the presence of non-polymeric amphipathic molecules, thereby producing a drop of a hydrophobic medium and a peripheral layer of the non-polymeric amphipathic molecules around the surface of the drop;
(ii) introducing a droplet of an aqueous medium into a hydrophobic medium in the presence of non-polymeric amphipathic molecules, thereby producing an aqueous droplet within the hydrophobic medium, said aqueous droplet comprising: (a) said aqueous medium and (b) an outer layer of said non-polymeric amphipathic molecules around the surface of the aqueous medium; wherein steps (i) and (ii) can be performed in either order or at the same time; and
(iii) transferring the aqueous droplet produced in step (ii) into the drop of hydrophobic medium produced in step (i), thereby producing said droplet encapsulate.

The hydrophilic carrier employed in step (i) may be any suitable hydrophilic medium. Typically, it is aqueous. Thus, the hydrophilic carrier typically comprises water. The hydrophilic carrier may for instance be pure water, or an aqueous solution. Typically, it is an aqueous buffer solution. Hydrophilic materials other than water may however be employed, for instance hydrophilic ionic liquids. Thus in one embodiment the hydrophilic carrier comprises an ionic liquid. In preferred embodiments, the hydrophilic carrier is an aqueous medium, for instance water or an aqueous buffer solution.

The hydrophobic medium used in step (i) may be as defined above for the droplet encapsulates of the invention. The drop of hydrophobic medium is introduced into the hydrophilic carrier in the presence of non-polymeric amphipathic molecules. The drop of hydrophobic medium is typically introduced into the hydrophilic carrier using a pipette. Typically, the non-polymeric amphipathic molecules are present in the hydrophobic medium itself, i.e. they are present in the hydrophobic drop. Alternatively, they may be provided in the hydrophilic carrier, for instance they may be dissolved, or suspended as lipid vesicles, in the hydrophilic carrier. The non-polymeric amphipathic molecules may be as defined above for the droplet encapsulates of the invention. Preferably, if the non-polymeric amphipathic molecules are not present in the hydrophobic medium, then they are present in both the aqueous medium of the droplet and in the hydrophilic carrier used in step (i). This improves the stability of the multisome.

The diameter of the hydrophobic drop may be controlled by forming the drop on a loop having a similar diameter. Typically, the hydrophobic drop is formed on the loop within the hydrophilic carrier. Thus, the empty loop is first submerged in the hydrophilic carrier, and the drop of hydrophobic medium is introduced into the hydrophilic carrier and then onto the loop. Usually, the drop of hydrophobic medium is pipetted into the hydrophilic carrier and onto the loop.

Alternatively, if a smaller hydrophobic drop is desired, the diameter of the hydrophobic drop may be controlled by using a micropipette, i.e. by introducing the drop of hydrophobic medium into the hydrophilic carrier from a micropipette.

The diameter of the hydrophobic drop is typically from 500 µm to 2000 more typically from 500 µm to 1500 for instance about 800 Larger drops and drops of smaller diameter can however be used. Accordingly, the diameter of the hydrophobic drop may be equal to or less than about 2 mm, or for instance equal to or less than 1 mm.

The formation of the peripheral layer of non-polymeric amphipathic molecules around the surface of the drop is straightforward. It is achieved simply by providing the non-polymeric amphipathic molecules in the hydrophobic medium of the drop or in the hydrophilic carrier, as described above, whereupon the layer can form naturally if the drop is left in the hydrophilic carrier for a sufficient period of time. The non-polymeric amphipathic molecules spontaneously form a layer, typically monomolecular, at the interface between the hydrophilic carrier and the hydrophobic drop, which becomes the peripheral layer of the droplet encapsulate of the invention.

The hydrophobic medium used in step (i) may also comprise any further agent, such as any therapeutic agent, drug, prodrug, diagnostic agent or other which it is desired to include in the hydrophobic medium of the resulting droplet encapsulate.

Step (ii) relates to the production of an aqueous droplet to be included into the multisome, and in step (ii) a droplet of an aqueous medium is introduced into a hydrophobic medium in the presence of non-polymeric amphipathic molecules. Of course, if more than one aqueous droplet to be included into the multisome, then more than one droplet may be prepared at this stage in accordance with step (ii), and then each of the resulting droplets for the multisome may be transferred into the hydrophobic drop in accordance with step (iii).

The hydrophobic medium used in step (ii) is typically the same hydrophobic medium which is used to produce the hydrophobic drop of step (i), and it may be any hydrophobic medium as defined above for the droplet encapsulates of the invention. The non-polymeric amphipathic molecules are usually present in the hydrophobic medium. Alternatively, however, they may be present in the aqueous medium of the droplet, for instance dissolved in the aqueous medium or suspended as lipid vesicles. Preferably, if the non-polymeric amphipathic molecules are not present in the hydrophobic medium, then they are present in both the aqueous medium of the droplet and in the hydrophilic carrier used in step (i). This improves the stability of the multisome. The non-polymeric amphipathic molecules used in step (ii) may be any of those discussed above for the droplet encapsulates of the invention.

The aqueous medium employed in step (ii) may be pure water. Alternatively, it may be an aqueous solution. The aqueous solution may be chosen for the purpose or use of the droplet in question within the multisome. One important property is pH and this can be varied over a wide range. The aqueous medium may therefore be an aqueous buffer solution. Any suitable buffer can be employed, depending on the desired pH. The buffer solution may for instance comprise Tris HCl, with KCl, and EDTA. If the aqueous droplet is to contain an agent, such as a therapeutic agent, drug, prodrug, diagnostic agent, activator, deactivator or sensor molecule, that agent is typically present in the aqueous medium which is used to form the droplet at this stage. Similarly, if the aqueous droplet is to communicate with other droplets in the multisome, or with the external environment, then a suitable membrane protein will typically be present in the aqueous medium at this stage. The protein may be any of the membrane proteins discussed hereinbefore for the droplet encapsulates of the invention.

The droplet of the aqueous medium may be introduced into the hydrophobic medium in step (ii) by using a micropipette, for instance a pipette with an electrophoresis gel-loading tip. A tip of the micropipette is typically filled with the aqueous medium, and then immersed in the hydrophobic medium. Just enough of the aqueous medium may then be expelled to expose a small pendant droplet, and the droplet may then be separated from the tip using any convenient method, for instance by pressing the tip against a wall of a vessel containing the hydrophobic medium. The volume of the aqueous droplet is usually equal to or less than 80 nL, but may for instance be equal to or less than 20 nL.

The formation of the outer layer of said non-polymeric amphipathic molecules around the surface of the aqueous medium is straightforward. It is achieved simply by providing the non-polymeric amphipathic molecules in the hydrophobic medium or in the aqueous medium of the droplet as described above, whereupon the outer layer can form naturally if the droplet is left in the hydrophobic medium for a sufficient period of time. The non-polymeric amphipathic molecules spontaneously form a layer, typically monomolecular, at the interface between the droplet and the hydrophobic medium.

The step of transferring the aqueous droplet into the drop of hydrophobic medium, to produce said droplet encapsulate of the invention, may be performed by any suitable method; the droplets are robust and easily manipulated. The step is usually performed using a pipette. However, such a step may also be carried out in a microfluidic device, as part of an automated procedure (see below).

If the droplet encapsulate is to contain more than one aqueous droplet, then more than one droplet may be transferred into the hydrophobic drop in this way, either by transferring an intact DIB network, chain or plurality of aqueous droplets into the hydrophobic drop, or by transferring unconnected droplets that may then form bilayers in situ. As mentioned above, the droplets are robust and easily manipulated.

Typically step (iii) is not performed until a period of time has elapsed sufficient to allow (a) formation of the outer layer of the non-polymeric amphipathic molecules around the surface of the droplet or droplets of aqueous medium and (b) formation of the peripheral layer of the non-polymeric amphipathic molecules around the surface of the drop of hydrophobic medium. This period of time needed to form stable monolayers may be referred to as the incubation time. The incubation time varies depending on the hydrophobic medium used and the concentration of the non-polymeric amphipathic molecules.

In one embodiment, step (iii) is not performed until at least 5 minutes after completion of steps (i) and (ii). In other embodiments, step (iii) is not performed until at least 10 minutes after completion of steps (i) and (ii), or for instance until at least 25 minutes after completion of steps (i) and (ii). In experiments using only DPhPC, the waiting time was ~10 min; using the DOPE/OA mixture, ~25 min; using the DSPC/DPhPC mixture, ~10 min.

The process of the invention for producing a droplet encapsulate of the invention may further comprise recovering said droplet encapsulate from the hydrophilic carrier. The droplet encapsulate may be recovered using any suitable technique, for instance by using a pipette to remove the droplet encapsulate from the hydrophilic carrier.

The process may then further comprise re-introducing the recovered droplet encapsulate into a further hydrophilic carrier. The further hydrophilic carrier may for instance be a pharmaceutically acceptable composition, water or an aqueous solution, an ionic liquid, or for instance a viscous or rigid hydrophilic carrier material.

Alternatively, the process of the invention for producing a droplet encapsulate of the invention may further comprise exchanging the hydrophilic carrier with a further hydrophilic carrier. Thus, for instance, when the hydrophilic carrier is an aqueous solution, the process may further comprise exchanging said aqueous solution by serial dilution with a new aqueous phase.

The invention further provides a droplet encapsulate which is obtainable by a process of the invention as defined above for producing a droplet encapsulate.

The droplet encapsulates of the invention can also be produced using microfluidic techniques, which may for instance employ consecutive shearing or flow-focusing microfluidic devices. Such techniques are particularly suitable for producing droplet encapsulates having small volumes and diameters (e.g. diameters of around 100 μm). Microfluidic techniques are therefore desirable for producing droplet encapsulates for administration in vivo, for instance in drug delivery applications.

Thus, in a further aspect, the invention provides a process for producing a droplet encapsulate, which process comprises:
 (i) introducing a droplet of aqueous medium from a first channel of a microfluidic device, which first channel contains said aqueous medium, into a second channel of the microfluidic device, which second channel contains a hydrophobic medium,
  wherein the aqueous medium in the first channel, or the hydrophobic medium in the second channel, or both, further comprise non-polymeric amphipathic molecules,
  thereby producing in the second channel an aqueous droplet within the hydrophobic medium, said aqueous droplet comprising: (a) said aqueous medium and (b) an outer layer of said non-polymeric amphipathic molecules around the surface of the aqueous medium; and
 (ii) introducing a drop of said hydrophobic medium from the second channel, which drop of hydrophobic medium comprises the aqueous droplet, into a third channel of the microfluidic device, wherein the third channel contains a hydrophilic carrier,
  wherein the hydrophobic medium in the second channel, or the hydrophilic carrier in the third channel or both, further comprise non-polymeric amphipathic molecules,
  thereby producing in the third channel a droplet encapsulate within the hydrophilic carrier, the droplet encapsulate comprising:
   the drop of said hydrophobic medium;
   a peripheral layer of non-polymeric amphipathic molecules around the surface of the drop; and
   said aqueous droplet within said peripheral layer.

The process may for instance be a consecutive shearing process (Okushima, S. et al., Langmuir 20, 9905-9908 (2004)) or a flow-focusing process (Chu, L. Y. et al., Angew. Chem. Int. Edit. 46, 8970-8974 (2007); Seo, M. et al., Soft Matter 3, 986-992 (2007)).

In one embodiment the process is a consecutive shearing process. Typically, in this embodiment, the first channel forms a substantially T-shaped junction with the second channel and the second channel forms a substantially T-shaped junction with the third channel. This arrangement encourages the production of aqueous droplets at the junction between the first and second channels, as well as the production of drops of said hydrophobic medium at the end of the second channel. Typically, the first and second channels are made of a hydrophobic material. This encourages the aqueous medium in these channels to form droplets and to remain in droplet form. Typically, the third channel is made of a hydrophilic material. This encourages the drop of said hydrophobic medium (which itself contains the aqueous droplet or droplets) to remain in the form of a drop in the third channel.

In another embodiment, the process is a flowfocusing process. Typically, in this embodiment, the end of the first channel from which the droplet of aqueous medium is produced protrudes into the second channel, and the end of the second channel from which the drop of said hydrophobic medium is produced protrudes into the third channel. Usually the aqueous medium flows through said first channel, said hydrophobic medium flows through said second channel, and said carrier medium flows through said third channel, in a continuous process.

The process may further comprise the recovery of said droplet encapsulate within said hydrophilic carrier from the microfluidic device.

The process may further comprise recovering the droplet encapsulate from the hydrophilic carrier. The droplet encapsulate may be recovered using any suitable technique, for instance by using a pipette to remove the droplet encapsulate from the hydrophilic carrier or by using an automated procedure in a microfluidic device. A microfluidic device may for instance be equipped with one or more traps for multisomes, allowing the external aqueous phase to be exchanged while keeping multisomes in place. Alternatively, a microfluidic device could use one external aqueous phase in the production of the multisomes, and then output the multisomes into a different external aqueous phase.

The process may then further comprise re-introducing the recovered droplet encapsulate into a further hydrophilic carrier. The further hydrophilic carrier may for instance be a pharmaceutically acceptable composition, water or an aqueous solution, an ionic liquid, or for instance a viscous or rigid hydrophilic carrier material.

Alternatively, the process of the invention for producing a droplet encapsulate of the invention may further comprise exchanging the hydrophilic carrier with a further hydrophilic carrier. Thus, for instance, when the hydrophilic carrier is an aqueous solution, the process may further comprise exchanging said aqueous solution by serial dilution with a new aqueous phase, or by using an automated procedure in a microfluidic device.

The invention further provides a droplet encapsulate which is obtainable by a process of the invention as defined above for producing a droplet encapsulate.

The present invention is further illustrated in the Examples which follow:

EXAMPLES

General Methods
Lipids and Oils

All lipids were purchased as powders from Avanti Polar Lipids and dissolved in pentane (DPhPC, DOPE) or chloroform (DSPC) at 10 mg ml$^{-1}$. Portions of these stock solutions were evaporated by using a nitrogen stream followed by at least 30 min under vacuum. The residues were re-solubilised at various concentrations in various oil mixtures. For experiments using only DPhPC, the lipid concentration was 0.1-0.2 mg ml$^{-1}$, and the oil was a 9:1 (v/v) mixture of silicone oil (Silicone Oil AR 20) and hexadecane (both from Sigma-Aldrich). The pH sensitivity experiments used a 2:1 (mol/mol) mixture of DOPE and OA (Sigma-Aldrich) at 10 mg ml$^{-1}$ total concentration, in a 19:1 (v/v) mixture of silicone oil and hexadecane. The temperature sensitivity experiments used a 3:1 (mol/mol) mixture of DSPC and DPhPC at 1 mg ml$^{-1}$ total concentration, in a 9:1 (v/v) mixture of silicone oil and hexadecane.

αHL Pores

Wild-type (WT) staphylococcal α-hemolysin (αHL) monomers were prepared by in vitro transcription-translation (IVTT), and heptamerised by incubation with rabbit red blood cell membranes. The heptamers were then purified by sodium dodecyl sulphate polyacrylamide gel electrophoresis (SDS-PAGE) to a final concentration of ~1 ng µl$^{-1}$ (Maglia, G. et al. Method. Enzymol. 475, 591-623, 2010). The protein was diluted 10- to 100-fold for the electrical recording experiments. The procedure used to prepare the αHL used in the fluorescence experiments has been described (Maglia, G. et al. Nano Lett. 9, 3831-3836, 2009). Briefly, a culture was grown from a single colony of the Wood 46 strain of *Staphylococcus aureus*. Spontaneously oligomerized heptamers of αHL were purified by cation exchange chromatography and gel electrophoresis, and stored at ~2 mg ml$^{-1}$ in 20 mM sodium phosphate buffer with 150 mM NaCl and 0.3% (w/v) SDS at pH 8.0. This protein solution was added to the aqueous droplets at a 50-fold dilution.

Buffers

The buffer used was 25 mM Tris HCl, pH 8.0, with KCl, EDTA and lipid concentrations as given in the text, except for the pH sensitivity experiments, where the buffer was 10 mM Tris.HCl, 10 mM succinic acid, 50 mM KCl, 50 µM EDTA at pH 8.0 or pH 3.0.

Example 1: Encapsulation

Multisomes were made in three steps. First, droplets of buffer of diameter ~300 µm were pipetted into oil containing dissolved lipids; typically the oil was a 9:1 (vol/vol) mixture of silicone oil and hexadecane, and the lipid was 1,2-diphytanoyl-sn-glycero-3-phosphocholine (DPhPC). Second, a droplet of the same oil solution of diameter ~800 µm was placed in a bulk buffer. Finally, after ~5 min a number of the aqueous droplets were transferred with a pipette into the oil droplet. Within ~1 min of encapsulation, the inner droplets adhered to each other, and to the surface of the oil droplet (FIG. 1C-E). These structures were stable for at least 24 h. For simplicity, the term "multisome" is used herein irrespective of the number of encapsulated droplets.

It was desirable to wait several minutes (the incubation time) before encapsulation. If transferred too soon, the aqueous droplets tended to fuse with each other and with the external aqueous phase. The incubation time may be required for well-packed lipid monolayers to form around the aqueous and oil droplets. These monolayers can then adhere to form lipid bilayers, either between two encapsulated droplets (an internal bilayer), or between an inner droplet and the external aqueous solution (an external bilayer).

In most of the foreseen applications, multisomes should be approximately neutrally buoyant in water, and silicone oil used was chosen accordingly for its density of 1.01 g·cm$^{-3}$. Equally important, however, was the minimum incubation time required to form stable multisomes with a given oil: whereas this was <5 min for the silicone oil and hexadecane mixture containing 0.2 mg ml$^{-1}$ DPhPC, multisomes made with 1-bromododecane (density 1.04 g cm$^3$) were not stable even after longer incubation times and at higher lipid concentrations.

Encapsulation—Methods

To study multisomes for prolonged periods, it was necessary to fix their positions while avoiding any interaction with the walls of the container that might disrupt the structure. For example, if the oil drop of a multisome contacts the air-bulk aqueous interface before it is entirely coated with a lipid monolayer, the drop will spread at that interface. Similarly, if the multisome contacts a container wall before monolayer formation, the oil drop can adhere to that surface, which can obstruct the formation of an external bilayer. This was achieved by suspending each multisome from a small loop of silver wire or plastic, of diameter ~0.8-1.5 mm, submerged in the bulk aqueous buffer. Silver loops were made by wrapping 100 µm diameter silver wire around a cylindrical template. Plastic loops consisted of cross-sections cut from pipette tips. Each loop was then attached to a silver wire fixed to the container wall. Multisomes could be dislodged from silver loops by mechanical disturbance, whereas plastic loops held multisomes very reliably because of their strong adhesion to the oil droplet.

A solution of lipids in oil was dispensed onto a loop to make an oil droplet of volume ~0.5-2 µl suspended in buffer. Micromachined acrylic wells were filled with the same oil solution, and aqueous droplets of volume ~0.5-70 nl were made in these wells using a 2 µl pipette with an electrophoresis gel-loading tip. The tip was filled with ~200 nl of the aqueous solution, then immersed in the oil solution. Just enough of the solution was expelled to expose a small pendant drop, and this drop was separated from the tip by pressing the pipette tip against the bottom of the well. After the waiting time, a pipette was used to transfer one or more of the aqueous droplets to the oil droplet in bulk aqueous solution. In experiments using only DPhPC, the waiting time was ~10 min; using the DOPE/OA mixture, ~25 min; using the DSPC/DPhPC mixture, ~10 min. Multisomes with several inner droplets could be formed either by transferring an intact DIB network, or by transferring unconnected droplets, which then formed bilayers in situ.

Free Energy Landscape

Following encapsulation but prior to bilayer formation, the oil and inner droplets in a multisome minimize their surface energies by adopting spherical geometries. After bilayer formation, multisomes have the geometries shown in FIGS. 2B-2D. These geometries represent a metastable compromise between the favourable adhesion of apposing monolayers to form bilayers, and unfavourable distortions that expose a greater monolayer or bilayer surface area. These states are only kinetically stable, as fusion of the inner droplets with the bulk aqueous phase would further decrease the free energy of the system. The surface tensions of a monolayer and bilayer, $\gamma_m$ and $\gamma_b$, respectively, are measures of the energetic cost of creating a unit area of each kind of interface. By considering the range of possible geometries of a multisome and calculating the energetic cost or benefit of each geometry relative to the state before bilayer formation, we may predict the most favourable geometry. Here we outline this calculation for a multisome with a single inner droplet.

First, to explore all possible geometries, it is necessary to parameterize the structure of a multisome. Assuming that each of the two monolayers and the bilayer minimize their own surface areas, it follows that the geometry of the multisome is composed of spherical caps. The geometry of the multisome can then be defined by the three contact angles illustrated in FIG. 2A. Imposing volume conservation for the oil and inner droplets, one of these angles is constrained and the other two remain free variables. The choice of which angle to constrain is arbitrary.

The free energy of formation of a multisome with a certain geometry is simply given by the changes in monolayer and bilayer surface areas relative to the spherical states, weighted by the surface tension of each interface. The free energy of formation of a multisome with contact angles $(\theta_1, \theta_2, \theta_3)$ is:

$$\Delta F = 2\pi\gamma_m \left[ r_1^2(1+\cos\theta_1) + r_2^2(1+\cos\theta_2) + \frac{\gamma_b}{\gamma_m}r_3^2(1+\cos\theta_3) - 2(R_1^2 + R_2^2) \right],$$

where $R_1$ and $R_2$ are the radii of the oil and inner droplets, respectively, before bilayer formation; the $r_i$ are the radii of curvature of the three spherical caps corresponding to the contact angles $\theta_i$, and can be evaluated from the $\theta_i$, $R_1$ and $R_2$.

Choosing $\theta_2$ and $\theta_3$ as the free variables, we can evaluate $\Delta F$ at each possible combination of $\theta_2$ and $\theta_3$ to produce a free energy landscape (FIG. 2B), using the following parameter values: $R_1$=400 µm, $R_2$=200 µm, $\gamma_m$=5 mN m$^{-1}$ (Yue, B. Y. et al., J. Chem. Soc. Farad. T. 1 72, 2685-2693 (1976); Morisaku, T., et al. Anal. Sci. 20, 1605-1608 (2004)) and $\gamma_b/\gamma_m$=0.68. The value of $\gamma_b/\gamma_m$ was obtained from measurements of DIB contact angles. The minimum of the landscape represents the local equilibrium geometry, which is illustrated in FIG. 2A. For the conditions used to calculate the landscape, the equilibrium contact angles are: $(\theta_1, \theta_2, \theta_3)$= (33°, 173°, 77°).

The absolute value of either $\gamma_m$ or m is required only to calculate the absolute free energy of formation. The equilibrium geometry of the multisome can be calculated given only the ratio of droplet volumes and the ratio $\gamma_b/\gamma_m$. Conversely, given a particular desired equilibrium geometry for a multisome, a similar analysis to that presented here could impose design constraints on the relative droplet volumes and surface tensions.

Example 2: Electrical Measurements

Figure 3A:
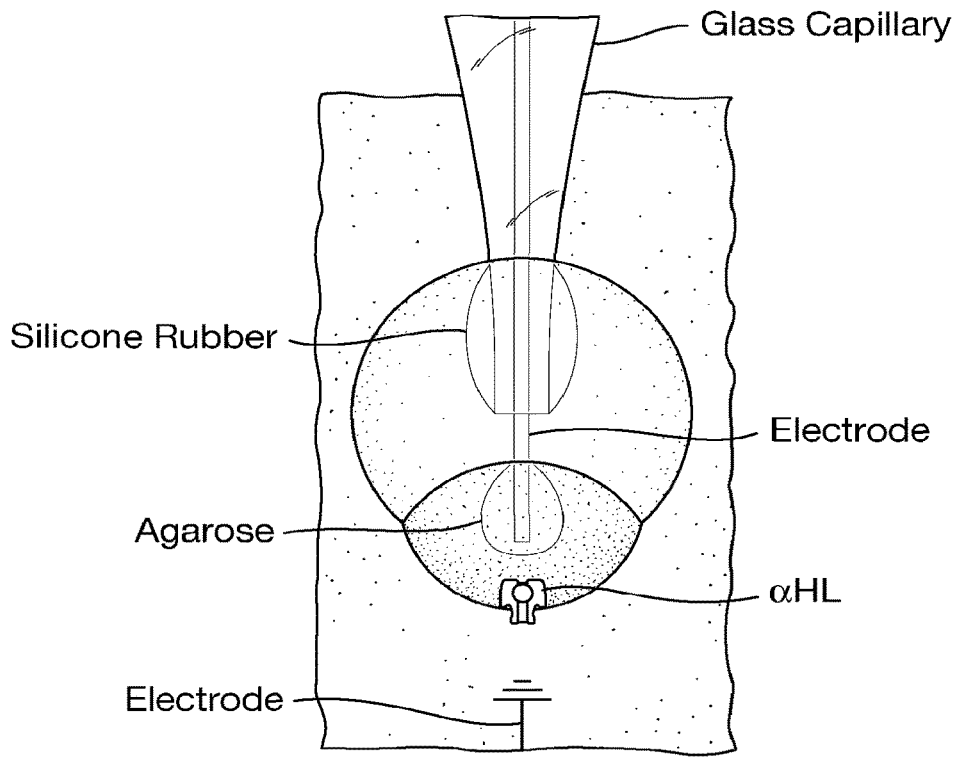
FIGS. 3A-3C relate to the measurement of ionic currents through staphylococcal α-hemolysin (αHL) pores. Thus.

By analogy with systems of DIBs in bulk oil (Holden, M. A. et al. J. Am. Chem. Soc. 129, 8650-8655 (2007)), the incorporation of membrane pumps, channels and pores into the bilayers of a multisome would allow precise control over the exchange of material, and electrical communication, between the various inner droplets and the external solution. To determine whether the external bilayers of multisomes can support the insertion of membrane proteins, electrical measurements were performed across the external bilayer of a multisome with a single inner droplet. To achieve this, a glass-insulated Ag/AgCl electrode was made that was electrically exposed only at its tip (see Methods, below). Immediately after an aqueous droplet was transferred into the oil droplet, the electrode tip was inserted into the inner droplet. Through micromanipulation of the electrode, the inner droplet was then brought to the surface of the oil droplet to allow bilayer formation (FIG. 3A).

Figure 3B:
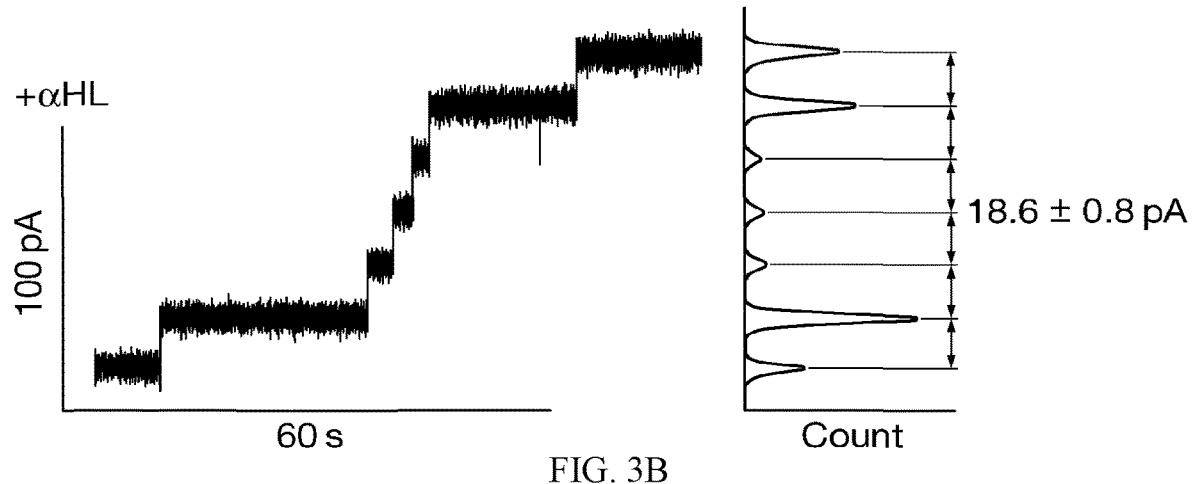

When wild-type (WT) staphylococcal α-hemolysin (αHL) was included in the inner droplet, stepwise increases in ionic current were observed within 1 min of bilayer formation, as recorded with the inserted electrode and a plain Ag/AgCl electrode in the external aqueous solution. A sample of such a current trace is shown in FIG. 3B. The amplitude of the steps was 18.6±0.8 pA (mean±s.d., n=16), consistent with the expected current of ~18.6 pA for the αHL pore under the given conditions (+50 mV, 500 mM KCl) (Stoddart, D. et al., Proc. Natl. Acad. Sci. USA 106, 7702-7707 (2009)). The current steps therefore corresponded to consecutive insertions of αHL pores into the external bilayer.

Figure 3C:
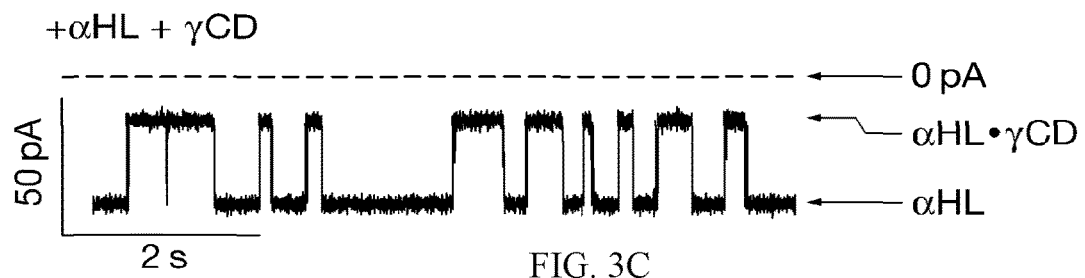

To confirm that the inserting pore was αHL, the experiment was repeated with a lower concentration of protein to reduce the probability of multiple insertions. After a few minutes, the current stepped from zero to a steady level, corresponding to the insertion of a single αHL pore into the external bilayer. Immediately afterwards, γ-cyclodextrin (γCD, ~10 μM) was added to the external aqueous solution, which caused reversible blockades of the current through the pore (FIG. 3C) with a blocking amplitude of 63.7±2.0% (mean±s.d., n=673) at ~50 mV in 1 M KCl. A least-squares linear fit to a 10 logarithmic histogram of the dwell times gives a dissociation rate of 4.0±0.6 $s^{-1}$ (mean±s.d.). A previous study employing DIBs found a blocking amplitude of ~60% and a dissociation rate of 2.0 $s^{-1}$ in pH 7.0 buffer (Holden, M. A. et al., J. Am. Chem. Soc. 129, 8650-8655 (2007).). The higher dissociation rate seen here in pH 8.0 buffer is consistent with the finding that the rate of dissociation of β-cyclodextrin from αHL increases with pH (Gu, L. Q. et al., Biophys. J. 79, 1967-1975 (2000)).

The electrical recording platform developed here might be used to study pore-forming protein complexes that span two lipid bilayers, such as gap junctions (Nakagawa, S. et al., Curr. Opin. Struc. Biol. 20, 423-430 (2010)) and nuclear pores (Strambio-De-Castillia, C. et al., Nat. Rev. Mol. Cell Bio. 11, 490-501 (2010)), at the single-molecule level by positioning two multisomes with single inner droplets such that their bilayers are apposed.

Electrical Measurements—Methods

Currents measured across DIBs and multisomes made with pure silicone oil showed occasional bursts of current leakage, which were suppressed by mixing the oil with a small proportion of hexadecane.

Currents were measured by using Ag/AgCl electrodes with a patch-clamp amplifier (Axopatch 200B, Axon Instruments) and 16-bit digitiser (1322A, Molecular Devices). Data were acquired at 10 kHz with a 2 kHz low-pass Bessel filter, and for analysis were further filtered with a 400 Hz low-pass Bessel filter.

Ag/AgCl electrodes were prepared by treating 25 or 100 μm diameter silver wire (Scientific Wire Company and Sigma Aldrich, respectively) with 25% sodium hypochlorite solution for at least 30 min.

Glass-sheathed electrodes were made by threading 25 μm-diameter silver wire through a glass capillary with internal and external diameters of 142 μm and 559 μm, respectively (Drummond). The capillary was then pulled (PC-10, Narishige) with the wire inside it, such that it separated into two pieces. The wire inside one of these pieces was soldered to an electrode pin at the larger opening of the capillary. Tweezers were used to trim ~50 μm of glass from the pulled end of the capillary, exposing the end of the wire. This end was then treated with sodium hypochlorite solution as above. A region near the pulled end of the capillary was coated with silicone rubber (3140 RTV Coating, Dow Corning) to prevent current leakage between the inner droplet and the external aqueous solution (FIG. 3A).

Example 3: Communication by Diffusion

Having established that αHL pores can insert into multisomal external bilayers, we explored whether the inner droplets of a multisome could use these pores to communicate passively with each other and with the external aqueous solution; that is, without driving the ion flux with an externally applied voltage.

Figure 4A:
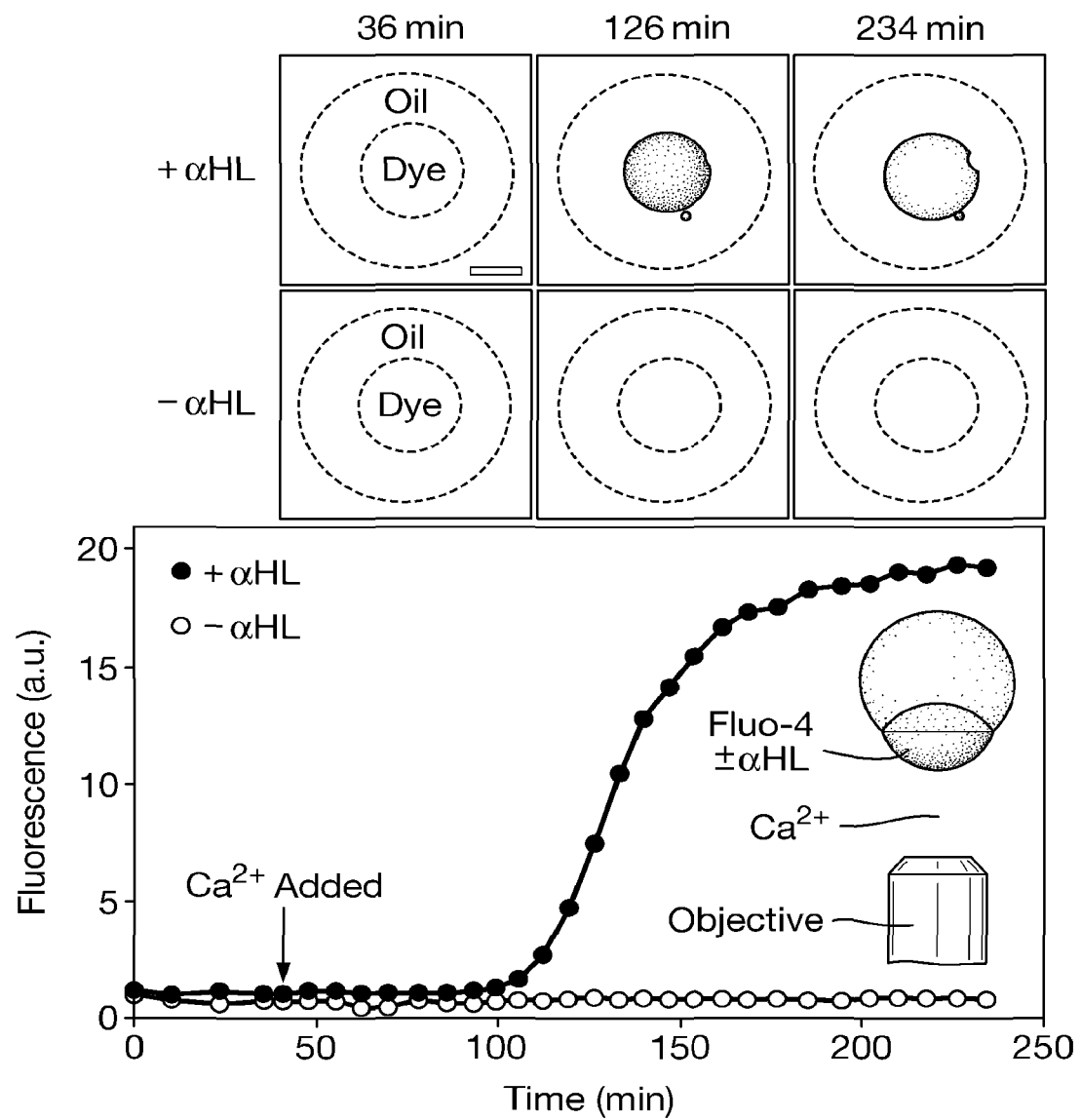
FIGS. 4A-4B relate to communication by diffusion through αHL pores. Thus.

First we tested whether an encapsulated droplet could communicate with the external aqueous solution. A multisome was made with a single inner droplet containing αHL pores and fluo-4 (a $Ca^{2+}$-sensitive dye) conjugated to 10,000 MW dextran, and monitored by fluorescence microscopy. The addition of $Ca^{2+}$ to the external solution caused the initially dark inner droplet to become fluorescent over ~1.5 h (FIG. 4A), whereas a multisome without αHL showed no fluorescence increase (n=6). We concluded that the fluorescence increase in the multisome containing αHL was caused by the diffusion of $Ca^{2+}$ ions from the external aqueous solution into the inner droplet, through αHL pores in the external bilayer. From electrical measurements across a DIB with the same concentration of αHL as that used in the multisome, the number of αHL pores inserted into the multisomal bilayer is expected to be several thousand.

Figure 4B:
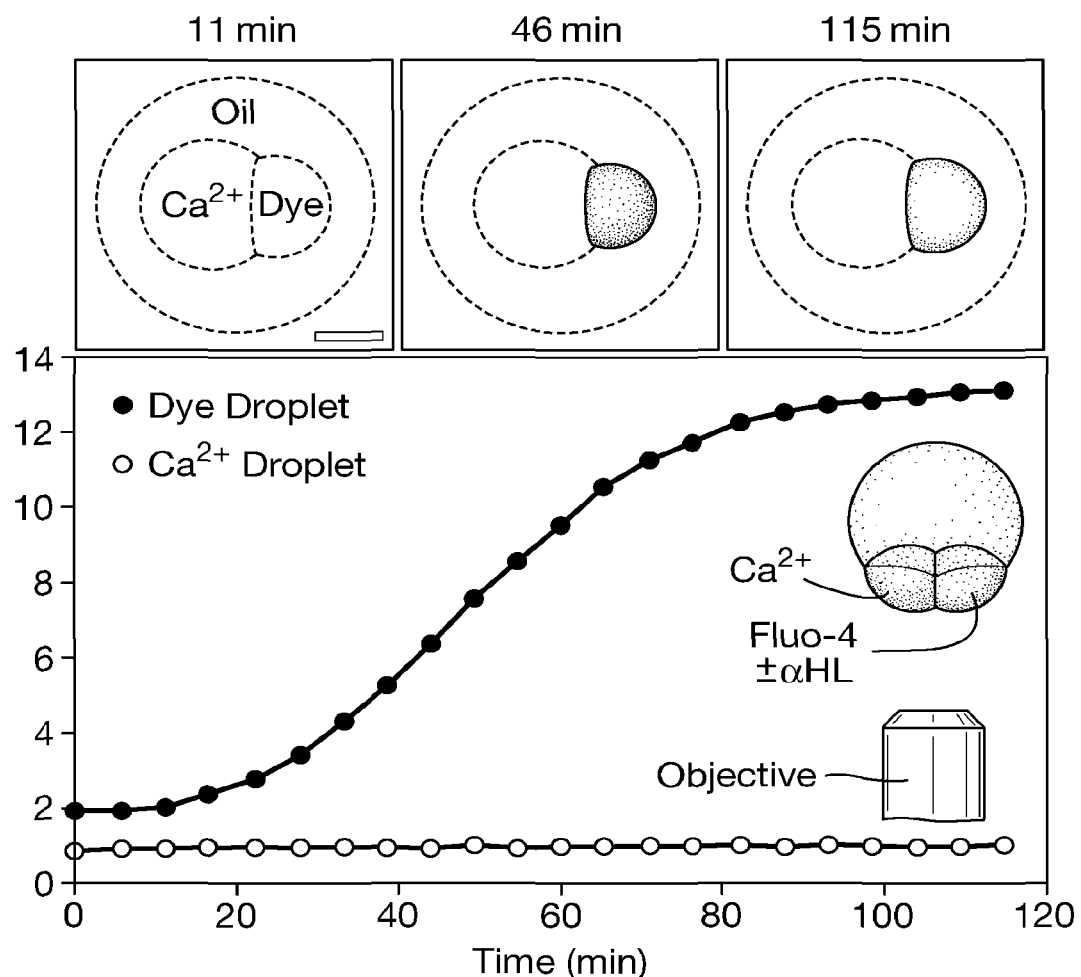

We then tested whether two inner droplets in a multisome could communicate with each other in a similar way, by including dextran-conjugated fluo-4 and αHL in one droplet and $Ca^{2+}$ in the other. The droplet containing fluo-4 increased in fluorescence over ~1 h (FIG. 4B), indicating the diffusion of $Ca^{2+}$ ions between the inner droplets through αHL pores in the internal bilayer. Together, these results demonstrate communication by passive diffusion between a multisome and the external solution, and within the inner droplets of a multisome.

The fluorescence measurements showed a time lag between the start of $Ca^{2+}$ flux and a fluorescence increase. This is due to competitive binding of $Ca^{2+}$ by EDTA, included in the inner droplets to chelate the small amount of contaminating $Ca^{2+}$ present in the buffer salt, which would otherwise have produced background fluorescence. $Ca^{2+}$ binds to fluo-4 and EDTA at similar rates ($k_{on}$~$10^7$-$10^8 M^{-1} s^{-1}$), but dissociates from fluo-4 much more rapidly than from EDTA, with $k_{off}$~400 $s^{-1}$ and <1 $s^{-1}$, respectively (Naraghi, M., Cell Calcium 22, 255-268 (1997); Johnson, J. D. et al., Biophys. J. 76, 1514-1522 (1999)). On a timescale of minutes, therefore, the EDTA acts as a sink for almost all the $Ca^{2+}$ in the droplet, and only once the EDTA has been saturated can a significant proportion of the fluo-4 molecules bind $Ca^{2+}$ ions.

Methods—Fluorescence Measurements

The potassium salt of fluo-4 conjugated to a 10,000 MW dextran (Invitrogen) was dissolved in pure water, and added to droplets at final dye concentration of 25 μM. Dye-containing droplets also contained 50 μM EDTA disodium salt. $Ca^{2+}$-containing droplets contained 100 mM $CaCl_2$.

Fluorescence microscopy was performed with a Nikon Eclipse TE2000-S inverted microscope with a Nikon CFI DL 10× objective, using a mercury arc lamp for illumination and the appropriate filter cube. Photographs were taken with a Hamamatsu C9100 EMCCD camera, with an exposure of 400 ms and gain of 179. Fluorescence intensities were measured using ImageJ software (Abramoff, M. D., Magelhaes, P. J. & Ram, S. J. Image processing with ImageJ. 11, 36-42 (2004)).

Example 4: Multisomes for Drug Delivery

The ability of a single multisome to keep several chemical species in separate compartments, and allow them to combine in a controlled fashion, enables novel means of drug delivery. The delivery of more than one pharmacological species to a cell using conventional liposomes requires that these species be encapsulated either together, allowing potentially undesirable reactions between them; or separately, in which case each cell will receive a poorly controlled proportion of each species. By contrast, the delivery of several drugs encapsulated in different compartments of a single multisome (including in the oil phase) would allow precise control over dosage proportions. This may be beneficial for the delivery of drugs with independent mechanisms of action; their uptake by cells in fixed proportions could be expected to increase their overall efficacy, and decrease the probability of resistance developing to any one of the drugs.

Beyond the simultaneous delivery of independent drugs, multisomal delivery would be particularly suited to prodrugs, inactive forms of drugs that can be activated by other species (Rautio, J. et al. Nat. Rev. Drug Discov. 7, 255-270 (2008)). In this case, each multisome would contain the prodrug in one inner droplet, and the activator in another inner droplet. Jointly releasing the droplet contents upon some external stimulus (such as a change in pH or temperature) would allow the prodrug and activator to combine, producing the active species in situ. This would allow the administration of drugs that are, for example, too unstable or insoluble to be delivered in the active state. For instance miproxifene phosphate, the inactive phosphate ester of the anticancer agent miproxifene, has 1,000-fold greater aqueous solubility than miproxifene, and is converted to the active species by alkaline phosphatases (Rautio, J. et al. Nat. Rev. Drug Discov. 7, 255-270 (2008)). Conversely, multisomes could be used to deliver "soft drugs" (active drugs that are deactivated by another species; Bodor, N. et al., Med. Res. Rev. 20, 58-101 (2000)). The inclusion of the active drug and its deactivator in separate droplets of the same multisome would give precise control over the lifetime of the active drug.

There are presently two broad approaches to the delivery of prodrugs. One makes use of activators that are already present in vivo (Rautio, J. et al. Nat. Rev. Drug Discov. 7, 255-270 (2008)), and therefore has a limited choice of activators. In the other approach, as in antibody-, gene- and virus-directed enzyme prodrug therapies (ADEPT, GDEPT and VDEPT, respectively), an exogenous activator is supplied to target cells prior to systemic administration of the prodrug (Niculescu-Duvaz, I. I. et al., Adv. Drug Deliver. Rev. 26, 151-172 (1997)). Although these approaches can make use of a wider range of activators, they face considerable obstacles. In ADEPT, the activator is coupled to an antibody targeted to the surface of a particular cell type. This antibody coupling can be costly to develop and introduces immunogenic complications (Xu, G. et al., Clin. Cancer Res. 7, 3314-3324 (2001)); further, the active drug must be capable of penetrating into the cytosol from the extracellular space. Although GDEPT and VDEPT avoid these problems by delivering genetic material for a prodrug-activating enzyme into the target cells, these approaches are limited to protein activators that can be expressed at high levels (Xu, G. et al., Clin. Cancer Res. 7, 3314-3324 (2001)).

The restrictions that apply to existing prodrug delivery systems may be circumvented by delivery with multisomes, bearing a prodrug and activator in separate compartments. A central problem for all drug delivery vehicles is triggering the release of entrapped drugs at the appropriate sites. Here we demonstrate the application to multisomes of two established mechanisms of triggered release, the first based on a decrease in pH and the second on a rise in temperature.

pH Sensitivity

Liposomes can be endocytosed by cells both with and without the use of specific targeting molecules (Torchilin, V. P. Nat. Rev. Drug Discov. 4, 145-160 (2005)). The discharge of liposomal contents into the cytosol can be achieved by engineering the liposomes to destabilize at acidic pH, so that they fuse with the endosomal membrane before the endosome progresses to a lysosome, where the contents may be sequestered or broken down (Chu, C. J. et al., Pharm. Res. 7, 824-834 (1990)). Miniaturized multisomes that are endocytosed and made to destabilize at acidic pH might also achieve intracellular drug delivery, by simultaneously releasing the prodrug and activator within the endosome. For the active drug to gain access to the cytosol, it must be made permeant to the endosomal membrane; conversely, the prodrug and activator must be impermeant to the multisomal membrane in order to prevent premature prodrug leakage. Specific examples include:

separately-encapsulated HMR 1826 and human beta-glucuronidase. The latter converts the former to doxorubicin. While HMR 1826 is not permeant to the cell membrane, doxorubicin is.

separately-encapsulated miproxifene phosphate and an alkaline phosphatase activator. The latter converts the former to miproxifene. Miproxifene is 1,000 times less water-soluble than miproxifene phosphate, and is therefore likely to be more membrane-permeant.

Alternatively, the active drug may gain access to the cytosol from the endosome or lysosome through efflux, for instance through recycling pathways.

One strategy for making pH-sensitive liposomes uses a mixture of two lipids (Drummond, D. C. et al., Prog. Lipid Res. 39, 409-460 (2000)). One, such as 1,2-dioleoyl-sn-glycero-3-phosphoethanolamine (DOPE), favours a non-bilayer state; another, such as oleic acid (OA), stabilizes the bilayer state at pH values above its $pK_a$ (~7.5 when incorporated in a bilayer (Hamilton, J. A. & Cistola, D. P. Proc. Natl Acad. Sci. USA 83, 82-86 (1986)), (Small, D. M., Cabral, D. J., Cistola, D. P., Parks, J. S. & Hamilton, J. A. Hepatology 4, 77S-79S (1984))), but not at lower pH values, when a significant proportion of OA is protonated. Here we apply this strategy to lend pH sensitivity to multisomes.

Figure 5A:
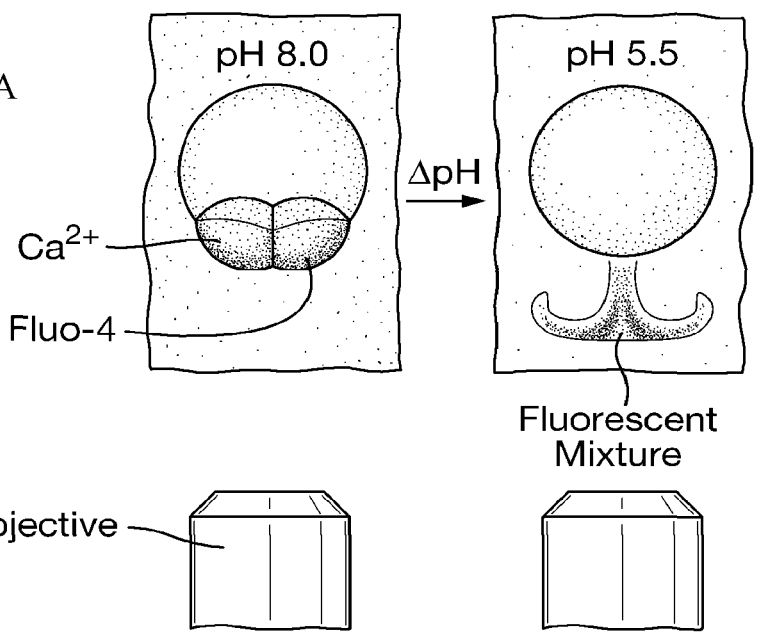
FIGS. 5A-5B relate to pH-dependent delivery. Thus.

Multisomes made with a mixture of DOPE and OA were found to be stable for at least a day in an external aqueous solution at pH 8.0 (n=7). On decreasing the pH of this solution from 8.0 to ~5.5 by replacing approximately half of it with an identical buffer at pH 3.0, the external bilayers suddenly ruptured, allowing the contents of the inner droplets to mix with each other and with the external solution (FIG. 5A). The droplets always burst within <2 min of each other, and usually within <1 min (n=8). Multisomes did not burst if the pH 8.0 buffer was exchanged with buffer of the same pH, showing that the bursting was not due to mechanical disturbance.

Figure 5B:
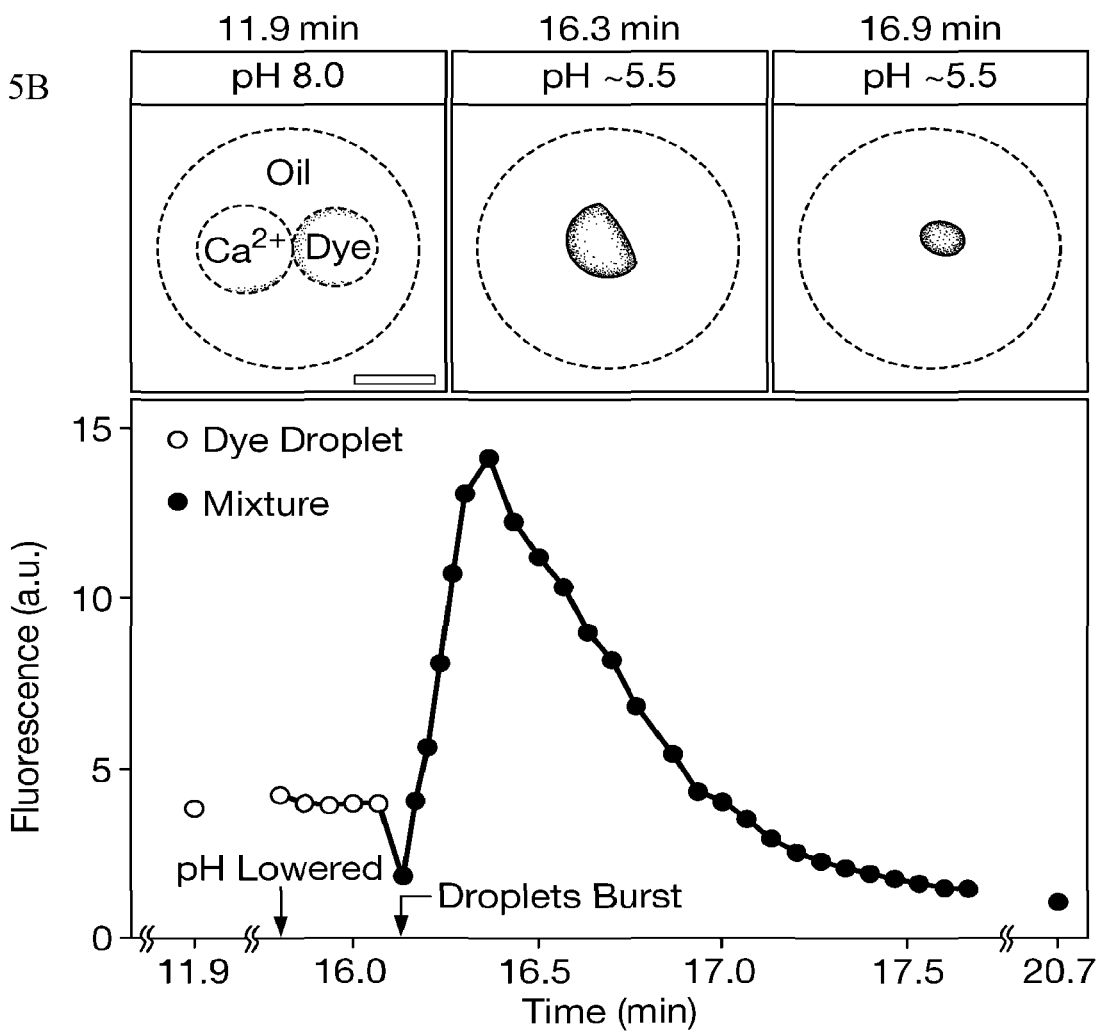

To test whether the contents of the droplets mixed with each other before diffusing away into the external solution, multisomes with two inner droplets were made in which one inner droplet contained dextran-conjugated fluo-4, and the other contained $Ca^{2+}$. These multisomes were monitored with fluorescence microscopy. Soon after lowering the pH of the external solution, both inner droplets burst simultaneously, releasing the $Ca^{2+}$ and fluo-4 into the external solution; the fluorescence intensity correspondingly decreased as the fluo-4 became diluted (FIG. 5B). Within seconds, the clouds of fluo-4 and $Ca^{2+}$ now in the external solution began to mix, and their intersecting volume showed a sharp increase in fluorescence intensity. Finally, this bright mixture became diluted, once again decreasing the fluorescence intensity.

pH Sensitivity—Methods

Dye-containing droplets contained 25 µM dextran-conjugated fluo-4 and 50 µM EDTA. $Ca^{2+}$-containing droplets contained 10 mM $CaCl_2$. Encapsulated droplets were allowed to equilibrate for ~15 min after formation, then approximately half the volume of the external aqueous solution was replaced with the same volume of the same pH 8.0 buffer. This was then repeated, but with the same volume of pH 3.0 buffer.

Temperature Sensitivity

We also implemented a mechanism for temperature-triggered release from multisomes. Liposomes made with a lipid with a melting transition temperature $T_m$ have a local maximum of permeability around $T_m$, attributable to the boundaries between the solid and fluid phases of the liposomal bilayer (Mills, J. K. et al., BBA-Biomembranes 1716, 77-96 (2005)). Delivery mechanisms using this phenomenon are being developed for use in conjunction with local mild hyperthermia of up to 42° C., producing a corresponding local enhancement in drug release (Needham, D. et al. Adv. Drug Deliver. Rev. 53, 285-305 (2001)).

Attempts to form multisomes with 1,2-dipalmitoyl-sn-glycero-3-phosphocholine (DPPC) (Tm=41° C.), popularly used for temperature-sensitive liposomes, did not yield stable bilayers when performed over a range of lipid concentrations and incubation times. The instability of giant DPPC liposomes has been noted elsewhere (Akashi, K. et al., Biophys. J. 71, 3242-3250 (1996); Korlach, J. et al., Proc. Natl. Acad. Sci. USA 96, 8461-8466 (1999)). However, multisomes made with a 1:1 (mol/mol) mixture of DPPC and DPhPC were stable, with ~90% surviving for at least 12 h (n=8). When subjected to a temperature gradient, the external bilayers of multisomes made with this lipid mixture with a single inner droplet ruptured suddenly at 32.6±1.6° C. (n=11), releasing the contents of the inner droplets into the external aqueous solution. The bursting temperature did not show a significant trend as the molar proportion of DPhPC was varied from ~15-75%, and significantly lower proportions of DPhPC failed to stabilise the bilayers.

That the bursting temperature is considerably lower than the transition temperature of DPPC is likely due to two factors. First, the addition of DPhPC to DPPC is known to significantly broaden the melting transition, and to decrease the peak transition temperature (Lindsey, H. et al., Biochim. Biophys. Acta 555, 147-167 (1979)). Second, the extent of the release of contents from temperature-sensitive liposomes has been shown to increase with their size (Ueno, M. et al., B. Chem. Soc. Jpn 64, 1588-1593 (1991)). The large area of the bilayers in our model multisomes compared to liposomes could therefore generate heightened temperature sensitivity. Together with the early onset of the melting transition caused by the addition of DPhPC, this increased sensitivity could account for the dramatic disruption of the bilayer observed well below the $T_m$ of pure DPPC.

Following the hypothesis that lipids similar to DPPC suffer a similar broadening of the melting transition upon the admixture of DPhPC, DPPC was replaced by 1,2-distearoyl-sn-glycero-3-phosphocholine (DSPC) (Tm ~55° C.) in order to raise the bursting temperature of multisomes to within a range appropriate for clinical mild hyperthermia. Multisomes made with a 3:1 (mol/mol) mixture of DSPC and DPhPC with a single inner droplet were found to be stable at room temperature for at least a day (n=11).

Figure 6A:
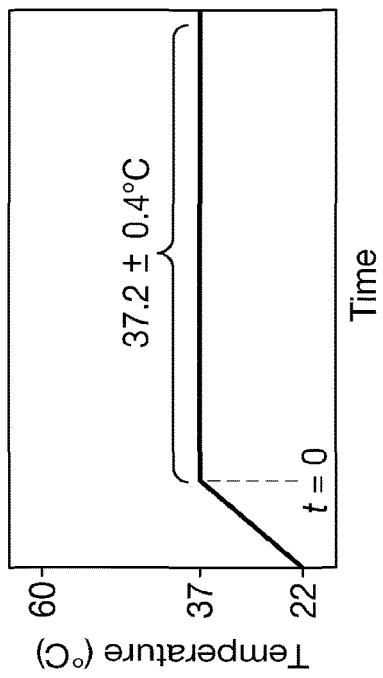
FIGS. 6A-6B relate to temperature-dependent delivery. Thus.

Multisomes made with this lipid mixture were subjected to a temperature ramp of ~1° C. min$^{-1}$, and the temperature at which each multisome burst was noted (FIG. 6A). Excluding ~3% of multisomes which burst at ~30° C., the bursting temperature was 43.6±3.5° C. (mean±s.d., n=93). When multisomes with two inner droplets were heated in the same way, in 70% of cases the two inner droplets of each multisome burst within 0.1° C. of each other, at 42.9±3.5° C. (mean±s.d., n=10).

Figure 6B:
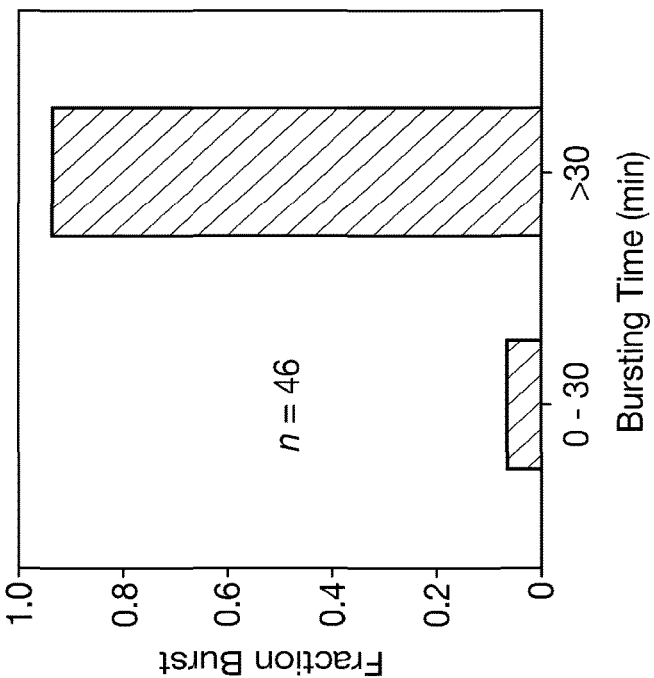

The multisomes were capable of retaining their contents at body temperature before being subjected to hyperthermia; when multisomes with a single inner droplet were held at 37.2±0.4° C., 93% survived for at least 30 min (n=46) (FIG. 6B).

Temperature Sensitivity—Methods

A container made to hold 12 multisomes on plastic loops was placed on a heating block, and the temperature of the bulk aqueous solution was measured with a thermocouple thermometer. The bulk solution was continuously stirred with a motor to ensure temperature homogeneity. The heating block thermostat was controlled using real-time feedback from temperature measurements to achieve the ramped and constant temperature regimes described in the text.

CONCLUSIONS

It has been shown in the present Examples that multisomes are stable in aqueous solution. Encapsulated droplets can exchange chemical species with each other and with the environment through membrane proteins incorporated in bilayers. Further, multisomes can respond to external stimuli such as pH and temperature by co-releasing the contents of the encapsulated droplets. These functionalities significantly expand the applicability of droplet network devices, for example as vehicles for combinatorial drug delivery.

The multisomes studied here were ~800 µm in diameter (FIG. 1C-E). This scale was convenient for the initial manipulation and study of single multisomes. However, some applications requiring multisomes to interact with living cells may require them to be no larger than a few microns, and ideally <200 nm, for their use in drug delivery (Devine, D. V., Biochim. Biophys. Acta 1191, 43-51 (1994)). The effect of increased curvature on the multisomal monolayers and bilayers is likely to become significant for multisomes smaller than ~1 µm in diameter (Lichtenberg, D. et al. Biochemistry (Mosc.) 20, 3462-3467 (1981)).

The high-throughput manufacture of miniaturized multisomes could be achieved by using existing microfluidic techniques, which employ consecutive shearing (Okushima, S. et al., Langmuir 20, 9905-9908 (2004)) or flow-focusing (Chu, L. Y. et al., Angew. Chem. Int. Edit. 46, 8970-8974 (2007); Seo, M. et al., Soft Matter 3, 986-992 (2007)) to encapsulate aqueous droplets in ~100 µm diameter oil droplets, in bulk aqueous solution. These structures have typically been stabilized by surfactants or block copolymers. A recent study (Shum, H. C. et al., Angew. Chem. Int. Edit. 50, 1648-1651 (2011)) used flow-focusing microfluidics to create groups of aqueous droplets joined by bilayers of block copolymers.

The invention claimed is:

1. A droplet encapsulate comprising:
   a drop of a hydrophobic medium which comprises an oil;
   a peripheral layer of non-polymeric amphipathic molecules around the surface of the drop; and
   an aqueous droplet, or a plurality of aqueous droplets, within the peripheral layer,
   wherein the or each aqueous droplet comprises: (a) an aqueous medium and (b) an outer layer of non-polymeric amphipathic molecules around the surface of the aqueous medium,
   wherein the droplet encapsulate comprises a bilayer of said non-polymeric amphipathic molecules, and wherein:

(i) an aqueous droplet is situated at the edge of the drop, wherein part of the outer layer of the aqueous droplet contacts said peripheral layer, thereby forming said bilayer of said non-polymeric amphipathic molecules at an interface between the aqueous droplet and the peripheral layer; or (ii) part of the outer layer of a first of said aqueous droplets contacts part of the outer layer of a second of said aqueous droplets, thereby forming said bilayer of the non-polymeric amphipathic molecules at an interface between said first and second droplets.

2. A droplet encapsulate according to claim 1, wherein:
an aqueous droplet is situated at the edge of the drop, wherein part of the outer layer of the aqueous droplet contacts said peripheral layer, thereby forming said bilayer of said non-polymeric amphipathic molecules at an interface between the aqueous droplet and the peripheral layer.

3. A droplet encapsulate according to claim 2, wherein said bilayer further a membrane protein.

4. A droplet encapsulate according to claim 1 comprising a plurality of said aqueous droplets within the peripheral layer, each aqueous droplet comprising: (a) a said aqueous medium, and (b) a said outer layer of non-polymeric amphipathic molecules around the surface of the aqueous medium.

5. A droplet encapsulate according to claim 4, wherein part of the outer layer of a first of said aqueous droplets contacts part of the outer layer of a second of said aqueous droplets, thereby forming a bilayer of the non-polymeric amphipathic molecules at an interface between said first and second droplets.

6. A droplet encapsulate according to claim 5, wherein said bilayer at the interface between said first and second droplets further comprises a membrane protein.

7. A droplet encapsulate according to claim 4, wherein at least one of said aqueous droplets is situated at the edge of the drop, wherein part of the outer layer of the aqueous droplet contacts the peripheral layer, thereby forming a bilayer of said non-polymeric amphipathic molecules at an interface between the aqueous droplet and the peripheral layer.

8. A droplet encapsulate according to claim 7, wherein said bilayer at the interface between said aqueous droplet and the peripheral layer further comprises a membrane protein.

9. A droplet encapsulate according to claim 4, wherein said plurality of aqueous droplets comprises more than two aqueous droplets which are in contact with one another in a chain or network, wherein a part of the outer layer of each droplet in the chain or network contacts a part of the outer layer of another droplet in the chain or network, thereby forming bilayers of the non-polymeric amphipathic molecules at interfaces between the droplets in the chain or network.

10. A droplet encapsulate according to claim 9, wherein each of said bilayers at the interfaces between droplets in the chain or network further comprises a membrane protein.

11. A droplet encapsulate according to claim 9, wherein at least one of the aqueous droplets in the chain or network is situated at the edge of the drop,
wherein part of the outer layer of the aqueous droplet situated at the edge of the drop contacts the peripheral layer, thereby forming a bilayer of said non-polymeric amphipathic molecules at an interface between said aqueous droplet and the peripheral layer.

12. A droplet encapsulate according to claim 11, wherein the bilayer at the interface between the aqueous droplet situated at the edge of the drop and the peripheral layer further comprises a membrane protein.

13. A droplet encapsulate according to claim 3, wherein the membrane protein is selected from a pump protein, a channel protein, a pore protein, a receptor protein, a transporter protein, a cell-recognition protein or a cell-to-cell interaction protein.

14. A droplet encapsulate according to claim 1, wherein the oil comprises silicone oil, a hydrocarbon, or a fluorocarbon, or a mixture of two or more thereof.

15. A composition comprising: a droplet encapsulate as defined in claim 1, or a plurality of said droplet encapsulates, and a hydrophilic carrier.

16. A protocell comprising a droplet encapsulate as defined in claim 1, wherein said peripheral layer of non-polymeric amphipathic molecules contacts the outer layer of said aqueous droplet and thereby forms a bilayer of non-polymeric amphipathic molecules around part of the aqueous droplet.

17. A prototissue comprising a droplet encapsulate as defined in claim 4, which droplet encapsulate comprises a plurality of said aqueous droplets, wherein the peripheral layer of non-polymeric amphipathic molecules contacts the outer layers of said aqueous droplets, thereby forming a bilayer of said non-polymeric amphipathic molecules around at least part of the surface of the plurality of aqueous droplets.

18. A sensor, battery, or electrical device comprising a droplet encapsulate as defined in claim 1.

19. A process for producing a droplet encapsulate, which droplet encapsulate comprises:
a drop of a hydrophobic medium which comprises an oil;
a peripheral layer of non-polymeric amphipathic molecules around the surface of the drop; and
an aqueous droplet, or a plurality of aqueous droplets, within the peripheral layer, wherein the or each aqueous droplet comprises: (a) an aqueous medium and (b) an outer layer of non-polymeric amphipathic molecules around the surface of the aqueous medium,
wherein the droplet encapsulate comprises a bilayer of said non-polymeric amphipathic molecules, and wherein:
an aqueous droplet is situated at the edge of the drop, wherein part of the outer layer of the aqueous droplet contacts said peripheral layer, thereby forming said bilayer of said non-polymeric amphipathic molecules at an interface between the aqueous droplet and the peripheral layer; or
(ii) part of the outer layer of a first of said aqueous droplets contacts part of the outer layer of a second of said aqueous droplets, thereby forming said bilayer of the non-polymeric amphipathic molecules at an interface between said first and second droplets;
which process comprises:
transferring an aqueous droplet, which aqueous droplet comprises (a) an aqueous medium and (b) an outer layer of non-polymeric amphipathic molecules around the surface of the aqueous medium,
into a drop of a hydrophobic medium, which drop of said hydrophobic medium has a peripheral layer of non-polymeric amphipathic molecules around its surface.

20. A process for producing a droplet encapsulate, which process comprises:
(i) introducing a droplet of aqueous medium from a first channel of a microfluidic device, which first channel contains said aqueous medium, into a second channel of the microfluidic device, which second channel contains a hydrophobic medium which comprises an oil,
    wherein the aqueous medium in first channel, or the hydrophobic medium in the second channel, or both, further comprise non-polymeric amphipathic molecules,
    thereby producing in the second channel an aqueous droplet within the hydrophobic medium, said aqueous droplet comprising: (a) said aqueous medium and (b) an outer layer of said non-polymeric amphipathic molecules around the surface of the aqueous medium; and
(ii) introducing a drop of said hydrophobic medium from the second channel, which drop of hydrophobic medium comprises aqueous droplet, or a plurality of said aqueous droplets, into a third channel of the microfluidic device, wherein the third channel contains a hydrophilic carrier,
    wherein the hydrophobic medium in the second channel, or the hydrophilic carrier in the third channel or both, further comprise non-polymeric amphipathic molecules, thereby producing in the third channel a droplet encapsulate within the hydrophilic carrier, the droplet encapsulate comprising:
the drop of said hydrophobic medium;
a peripheral layer of non-polymeric amphipathic molecules around the surface of the drop; and
said aqueous droplet, or said plurality of said aqueous droplets, within said peripheral layer,
wherein the droplet encapsulate comprises a bilayer of said non-polymeric amphipathic molecules, and wherein:
an aqueous droplet is situated at the edge of the drop, wherein part of the outer layer of the aqueous droplet contacts said peripheral layer, thereby forming said bilayer of said non-polymeric amphipathic molecules at an interface between the aqueous droplet and the peripheral layer; or
(ii) part of the outer layer of a first of said aqueous droplets contacts part of the outer layer of a second of said aqueous droplets, thereby forming said bilayer of the non-polymeric amphipathic molecules at an interface between said first and second droplets.

* * * * *

UNITED STATES PATENT AND TRADEMARK OFFICE
CERTIFICATE OF CORRECTION

PATENT NO. : 11,998,642 B2
APPLICATION NO. : 17/853000
DATED : June 4, 2024
INVENTOR(S) : John Hagan Pryce Bayley, Andrew Heron and Gabriel Villar It is certified that error appears in the above-identified patent and that said Letters Patent is hereby corrected as shown below:

In the Claims

In Claim 19, Column 56, Line 45, delete "an aqueous droplet" and insert -- (i) an aqueous droplet --.

In Claim 20, Column 58, Line 11, delete "an aqueous droplet" and insert -- (i) an aqueous droplet --.

Signed and Sealed this
Twenty-third Day of July, 2024

Katherine Kelly Vidal
*Director of the United States Patent and Trademark Office*